(12) United States Patent
Ahlman

(10) Patent No.: US 7,490,377 B2
(45) Date of Patent: Feb. 17, 2009

(54) PATIENT SINGLE SURFACE SYSTEM

(75) Inventor: Scott M. Ahlman, Oregon, WI (US)

(73) Assignee: Ahlman IP, Inc., Oregon, WI (US)

( * ) Notice: Subject to any disclaimer, the term of this patent is extended or adjusted under 35 U.S.C. 154(b) by 151 days.

(21) Appl. No.: 11/566,040

(22) Filed: Dec. 1, 2006

(65) Prior Publication Data

US 2007/0124858 A1    Jun. 7, 2007

Related U.S. Application Data

(60) Provisional application No. 60/742,222, filed on Dec. 5, 2005.

(51) Int. Cl.
*A61G 7/10*        (2006.01)

(52) U.S. Cl. .............. 5/81.1 R; 5/83.1; 5/613; 5/620

(58) Field of Classification Search ............... 5/81.1 R, 5/83.1–89.1, 620, 612, 613, 617
See application file for complete search history.

(56) References Cited

U.S. PATENT DOCUMENTS

| | | | |
|---|---|---|---|
| 2,512,160 A | 6/1950 | Koenigkramer | |
| 2,610,330 A | 9/1952 | Sutton | |
| 2,696,963 A | 12/1954 | Shepherd | |
| 2,905,952 A | 12/1959 | Reichert | |
| 3,298,042 A * | 1/1967 | Danielson | 5/83.1 |
| 3,304,116 A | 2/1967 | Stryker | |
| 3,694,830 A * | 10/1972 | Koller | 5/610 |
| 3,709,372 A | 1/1973 | Alexander | |
| 3,815,164 A | 6/1974 | Smith | |
| 3,902,204 A | 9/1975 | Lee | |
| 3,917,076 A | 11/1975 | Campbell | |
| 4,016,612 A | 4/1977 | Barile | |
| 4,019,772 A | 4/1977 | Lee | |
| 4,262,872 A | 4/1981 | Kodet | |
| 4,273,374 A | 6/1981 | Portman | |
| 4,432,359 A * | 2/1984 | James | 5/87.1 |
| 4,489,454 A | 12/1984 | Thompson | |
| 4,658,450 A | 4/1987 | Thompson | |
| 4,720,881 A | 1/1988 | Meyers | |
| 4,768,241 A | 9/1988 | Beney | |
| 4,939,801 A | 7/1990 | Schaal et al. | |
| 5,014,968 A | 5/1991 | Lammers et al. | |
| 5,016,307 A | 5/1991 | Rebar | |
| 5,083,331 A * | 1/1992 | Schnelle et al. | 5/600 |
| 5,111,541 A | 5/1992 | Wagner | |

(Continued)

FOREIGN PATENT DOCUMENTS

EP        1 449 506       8/2004

(Continued)

*Primary Examiner*—Michael Trettel
(74) *Attorney, Agent, or Firm*—McHale & Slavin, P.A.

(57) ABSTRACT

This invention is directed towards a patient single surface system, PS3, which is a next generation system solution for patient accommodation, diagnosis, treatment, transfer and transport. PS3 provides a single surface for the patient to remain on from the trauma site through diagnosis, treatment and convalescence. Needs addressed by the PS3 system include improved patient treatment through reduction in time to treatment, reduced or eliminated unnecessary patient movement and injury, as well as improved comfort throughout treatment and convalescence. In addition, the PS3 system solves significant economic considerations.

26 Claims, 76 Drawing Sheets

U.S. PATENT DOCUMENTS

| | | |
|---|---|---|
| 5,117,521 A | 6/1992 | Foster et al. |
| 5,187,821 A | 2/1993 | Nieminen et al. |
| 5,285,539 A | 2/1994 | Anderson et al. |
| 5,319,817 A | 6/1994 | Hay et al. |
| 5,407,163 A | 4/1995 | Kramer et al. |
| 5,461,740 A | 10/1995 | Pearson |
| 5,475,884 A | 12/1995 | Kirmse et al. |
| 5,487,195 A | 1/1996 | Ray |
| 5,588,166 A | 12/1996 | Burnett |
| 5,611,638 A | 3/1997 | Dorr et al. |
| 5,651,150 A | 7/1997 | Kanitzer et al. |
| 5,687,942 A | 11/1997 | Johnson |
| 5,699,988 A | 12/1997 | Boettger et al. |
| 5,934,282 A | 8/1999 | Young, III et al. |
| 5,987,670 A | 11/1999 | Sims et al. |
| 6,073,285 A | 6/2000 | Ambach et al. |
| 6,098,216 A | 8/2000 | Williamson |
| 6,101,644 A | 8/2000 | Gagneur et al. |
| 6,178,575 B1 | 1/2001 | Harade |
| 6,374,438 B1 | 4/2002 | Fox et al. |
| 6,375,133 B1 | 4/2002 | Morrow |
| 6,499,163 B1 | 12/2002 | Stensby |
| 6,546,577 B1 | 4/2003 | Chinn |
| 6,619,599 B2 | 9/2003 | Elliott et al. |
| 6,640,364 B1 | 11/2003 | Josephson et al. |
| 6,782,571 B1 | 8/2004 | Josephson et al. |
| 6,854,140 B2 * | 2/2005 | Bartels et al. ............... 5/601 |
| 2001/0044957 A1 | 11/2001 | Hodgetts |
| 2002/0042952 A1 | 4/2002 | Smeed |
| 2002/0162926 A1 | 11/2002 | Nguyen |
| 2002/0174485 A1 | 11/2002 | Bartels |
| 2003/0101513 A1 | 6/2003 | Wong |
| 2003/0213064 A1 | 11/2003 | Johnson |
| 2004/0111800 A1 | 6/2004 | Bartels et al. |
| 2005/0102748 A1 | 5/2005 | Johnson |
| 2005/0246833 A1 | 11/2005 | Barth et al. |

FOREIGN PATENT DOCUMENTS

| | | |
|---|---|---|
| FR | 2 789 302 | 8/2000 |
| GB | 2 039 731 | 8/1980 |
| WO | WO 89 02260 | 3/1989 |
| WO | WO 90 03158 | 4/1990 |
| WO | WO 94 09738 | 5/1994 |

* cited by examiner

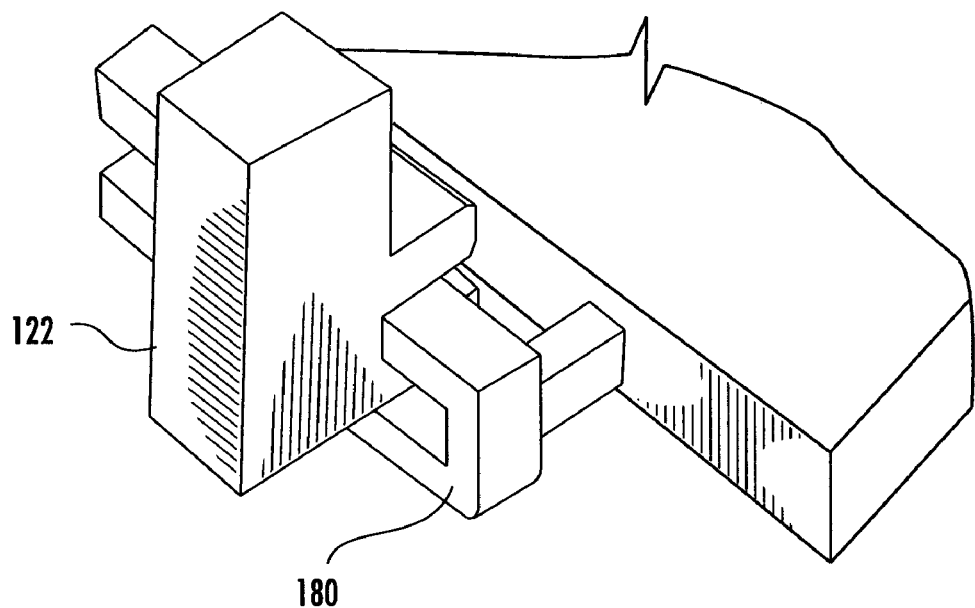
FIG. 79
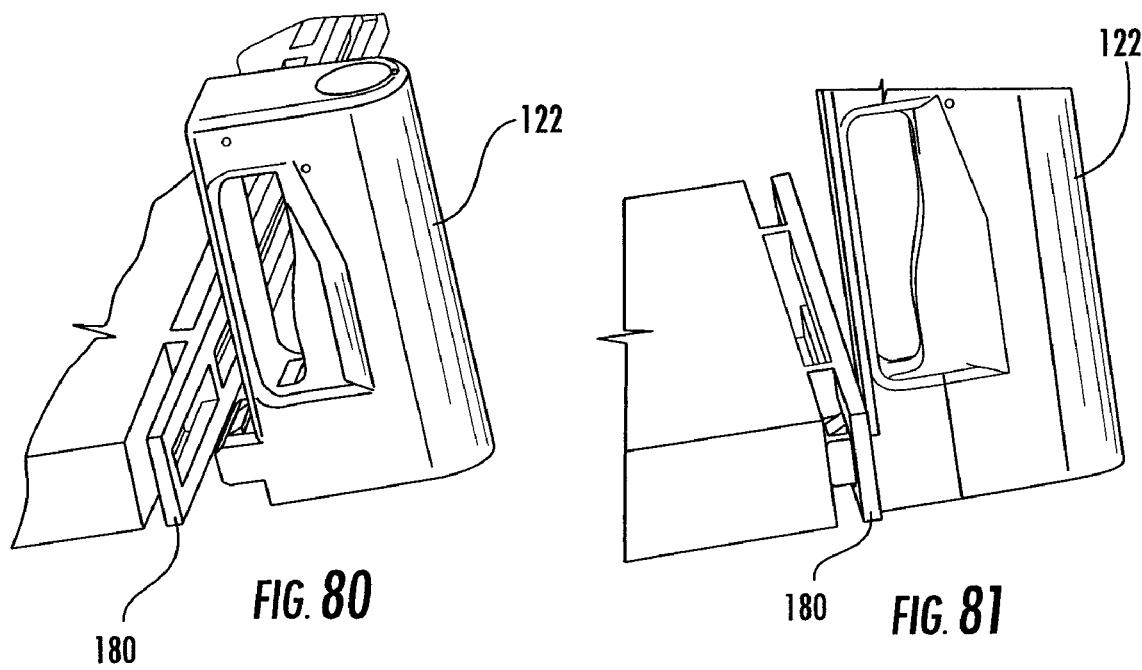
FIG. 80
FIG. 81

PATIENT SINGLE SURFACE SYSTEM

REFERENCE TO RELATED APPLICATIONS

This application claims the benefit under 35 U.S.C. §119 (e) of Provisional Application No. 60/742,222, filed on Dec. 5, 2005, and entitled Patient Single Surface System, the contents of which are herein incorporated by reference.

FIELD OF THE INVENTION

This invention generally relates to a single surface system for patient accommodation, diagnosis, treatment and transfer. The invention particularly relates to a contoured thin single surface platform or bed surface and a unique single surface platform to cantilever frame interface which functions in concert with unique, auxiliary components and systems designed to interface with the single surface platform patient accommodation, diagnosis, treatment and transfer systems, for enabling the patient to remain on a single surface from the trauma site through, diagnosis, treatment and convalescence, while simultaneously adapting and accommodating auxiliary features and modules.

BACKGROUND OF THE INVENTION

Patients in a medical care facility often require movement from one location to another within the facility. This frequent movement is often necessitated by the layout or configuration of the facility. A typical medical care facility is organized into several specialty centers. These centers may include, for example, an emergency room, the patient's room, a radiology center, operating rooms and a recovery center. Each of these centers typically has a bed (single surface platform) or procedure area onto which the patient must be transferred upon their arrival into the center. For example, if a patient is brought into the emergency room they usually arrive in an ambulance. Upon arrival the patient must be transferred from the ambulance gurney to a bed in the emergency room. If the physician in the emergency room requires an x-ray for his diagnosis, the patient must be transferred from the bed in the emergency room onto a transport gurney. The gurney is then transported to the radiology center and the patient is placed onto the x-ray table. After the x-ray procedure is complete, the patient is transferred onto another gurney and transported back to the emergency room where the patient is then transferred back into a bed. Thus, prior to being admitted into the medical care facility, the patient has already required five transfer events (from the ambulance gurney to the emergency room bed, from the bed onto a gurney, from the gurney to the x-ray table, from the x-ray table back to a gurney, and from the gurney back to bed) and three transport events (from the ambulance to the emergency room bed, from the bed to the radiology center and from the radiology center back to the emergency room bed). If the patient is then admitted into the medical care facility there are two more transfer events and another transport event.

Patient transfer is typically performed when transferring the patient from a bed to a transport device such as a gurney. Often times the patient is not conscious or cannot physically assist in the transfer and so the hospital personnel must perform the transfer. The current patient transfer method with a bed sheet or thin plastic sheet requires between four and six personnel for incapacitated patients depending on patient size and personnel available. Current transfer methods are entirely a manual process, which requires significant lifting, pushing and pulling onto a transferring device (e.g. a roller-board or a back board), lifting the patient from the bed and placing the patient on a gurney. Patient handling is the leading cause of hospital staff injury. While it is not clear if patient surface transfer is the leading cause, it does appear to cause approximately 4000 reported incidents of injury/year according to US Bureau of Labor Statistics data, ranging in a direct cost of between $28 and $112 Million/year-depending on injury severity. Furthermore, this process can lead to injury to the patient caused by either improper manipulation or dropping. Since studies show that the average weight of the population is increasing, this transfer process will continue to become more difficult and injury-prone in the future. The disclosed PS3 single surface design allows a single person to easily transfer a patient, along with the auxiliary equipment for the patient, such as intravenous fluids and medications, which remain connected throughout the transfer of the patient.

There is additionally a need to improve patient movement through a medical care facility and reduce the time prior to starting of the treatment. This is exemplified by the need for reduction in the time required to provide treatment for stroke victims once they have arrived in the hospital. Data has demonstrated that the current manual, multi-person transfer of patients to imaging equipment were a key bottleneck in the diagnosis and treatment of stroke patients. Analysis of the data indicated that 20 to 40 minutes alone could be lost prior to the start of treatment for a stroke victim due to the standard transfer procedures from bed to radiologic device tables. Furthermore, a need exists to minimize disturbance/movement of patients, especially spinal injury victims, where the possibility of harming the patient during transfer is a very real possibility.

With regard to hospital staff injuries during patient transfers, it is well documented that immobilized acute care patients currently require multiple, injury-prone, manual, multi-person transfers from one surface to another throughout the care process from the incoming ambulance gurney to a hospital gurney and within the hospital for triage, imaging, surgery and various testing. This care process can vary from a short period (hours) to a couple of days.

In recognition of these needs to provide improvements in the areas of efficiency, cost and continuity of patient care, the instant inventor has provided herein a Patient Single Surface System (PS3) which provides a stable, cantilever frame design to support a resting and supporting surface (e.g. a bed) which provides a single surface platform on which the patient remains at all times, even during transfer from one surface to another (i.e. transfer to triage beds, imaging tables, diagnostic tables, gurneys, etc.). The PS3 cantilever design and contoured single support surface for transfer requires only a single person, regardless of patient weight, to position the unit above the surface for transfer, and subsequently lower them mechanically with the cantilever frame. Lifting, pulling, and or pushing of the patient is not required. Further, additional personnel are not required to move the patient, even for completely incapacitated patients.

PRIOR ART

Numerous prior art references exist which disclose a variety of disparate features generally related to transport mechanisms per se, and/or transport mechanisms compatible with medical equipment such as imaging devices. These references include: (A1) US Patent Pub. 2005/0246833, published Nov. 10, 2005 to Barth et al.; (A2) US Patent Pub. 2004/0111800, published Jun. 17, 2004 to Bartels et al.; (A3) US Patent Pub. 2003/0101513, published Jun. 5, 2003 to Wong; (A4) US Patent Pub. 2002/0042952, published Apr. 18, 2002 to Smeed; (A5) EP Patent 1 449 506 A1, published on Aug. 25, 2004 to Medical Iberica, S. A.; (A6) U.S. Pat. No. 6,782, 571, issued Aug. 31, 2004 to Josephson et al.; (A7) U.S. Pat. No. 6,640,364, issued Nov. 4, 2003 to Josephson et al.; (A8) U.S. Pat. No. 6,374,438, issued Apr. 23, 2002 to Fox et al.; (A9) U.S. Pat. No. 6,178,575, issued Jan. 30, 2001 to Harada; (A10) U.S. Pat. No. 6,098,216, issued Aug. 8, 2000 to Williamson et al.; (A11) U.S. Pat. No. 5,475,884, issued Dec. 19, 1995 to Kirmse et al.; (A12) U.S. Pat. No. 5,319,817, issued Jun. 14, 1994 to Hay et al.; (A13) U.S. Pat. No. 5,285,539, issued Feb. 15, 1994 to Anderson et al.; (A14) U.S. Pat. No. 4,939,801, issued Jul. 10, 1990 to Schaal et al.; (A15) U.S. Pat. No. 4,658,450, issued Apr. 21, 1987 to Thompson; (A16) U.S. Pat. No. 4,019,772, issued Apr. 26, 1977 to Lee; (A17) U.S. Pat. No. 3,815,164, issued Jun. 11, 1974 to Smith; (A18) U.S. Pat. No. 3,304,116, issued Feb. 14, 1967 to Stryker; and (A19) U.S. Pat. No. 2,905,952, issued Sep. 29, 1959 to Reichert et al.

Reference A1 to Barth et al. discloses various embodiments of a patient removal system for evacuating a patient during an emergency. The patient removal systems may be used to transport the patient while the patient is on a mattress, or the patient removal systems may be used to transport the patient without the mattress. The patient removal systems permit caregivers to transport patients out of danger or harm without requiring patient support devices to be transported along with the patients.

Reference A2 to Bartels et al. discloses a gurney for transporting a patient. The gurney has a chassis with a support component for a supporting board for a patient. The board is fastened to prevent lateral motion and can be removed to provide medical treatment or to provide an examination device. The support component allows at least two different boards to be alternately supported and fastened with a positive fit at their head ends. The boards are different from one another at their head ends on the underside in shape and/or in width.

Reference A3 to Wong discloses a hospital bed adapted for use with an open geometry imaging system, such as a C-arm imager. The hospital bed includes a mobile base, a frame, a bed top, and a patient support. At least one portion of the bed top and patient support are substantially radiotransparent. The radiotransparent portions are capable of axial displacement along the lengthwise axis of the bed, thereby allowing the use of an imager on a patient in the bed without interference from the base. The axial displacement is preferably indexed to at least one predetermined stop position. One or more independent lateral sections can be selectively moved away from the radiotransparent portion, allowing for a reduction in the overall width of the bed. A patient transport system is also provided, in which the bed top and attached patient support can be used as a portable support, such as a stretcher, and may be secured to the base for subsequent transport and/or imaging when appropriate.

Reference A4 to Smeed discloses an invention formed from a platform (100) having a support surface (110), a pair of legs (150, 150) connected to the support surface (110), and footings (152) and securing mechanism (160 or 180) on the legs (150, 150) for attaching the invention to a litter that preferably satisfies NATO requirements. Preferably, the invention attaches to the poles used to carry a patient on a litter such that the invention provides space for the patient's legs to pass under if necessary. A further embodiment of the invention adds at least one accessory clip, which preferably includes at least one attachment for a piece of medical equipment such as medical monitors, ventilators, and infusion pumps.

Reference A5 to Medical Iberica, S. A. discloses a gurney which has a base platform with two levels joined by an oblique central transition segment. The lower segment housing includes a power source and a means for raising the mattress, while another articulated means for raising the gurney includes on each side a pair of tubes that rise from the two levels of base platform. The base platform is jointed to curved tubes which are joined to the frame of the mattress. The frame also incorporates a control for turning the mattress towards its drainage area.

Reference A6 to Josephson et al. discloses a patient transport system for transporting a patient from a magnetic resonance imaging system to a second imaging system and includes an elongated member and first and second coupling mechanisms. The elongated member has an upper surface configured to support a patient. The first coupling mechanism is coupled to the elongated member and is configured to removably couple the elongated member to the magnetic resonance imaging system. The second coupling mechanism is coupled to the elongated member and is configured to removably couple the elongated member to a second imaging system.

Reference A7 to Josephson et al. discloses a pedestal for use with a patient transport system for multiple imaging systems can include a support member configured to support a patient or object of interest, an elongated planar member coupled to the support member and configured to removably couple and slidably engage an elongated cradle member, and a docking assembly coupled to the elongated planar member configured to engage the receipt of and the removal of the elongated cradle member supportable by the elongated planar member.

Reference A8 to Fox et al. discloses a mobile patient stretcher particularly adapted for additional use as a pain clinic treatment table designed to accommodate a C-arm of a fluoroscopic or like imaging apparatus. The stretcher litter top or patient support surface is radiolucent and includes selectively removable lateral side rail sections so that the litter top can be selectively converted into an hourglass shape without side rails as required for treatment procedures and/or C-arm access and imaging. Alternatively, with the lateral side rail sections in place, the stretcher includes a full-width patient support surface, and also includes a radiolucent fowler back rest, selectively deployable side rails, and a hydraulically or otherwise controlled conventional wheeled stretcher base that is adapted to place the patient support surface in a raised, lowered, Trendelenburg, or reverse Trendelenburg orientation. The stretcher can be used as a fully functional stretcher to transport a patient to and from a procedure area and a recovery area, provides a comfortable resting place with a fowler back rest for a patient, and is also usable as a treatment table during fluoroscopic or other imaging procedures.

Reference A9 to Harada discloses a stretch mounting unit which includes a unit body detachably mounted on a stretcher. A drive device is attached to the unit body for providing an output with a center shaft for receiving the output of the drive device. A coupling that couples the drive device and the center shaft for transmitting the output of the drive device to the center shaft includes a roller pressed on the center shaft to produce torque. A carrier swingably disposed on the center shaft, a pair of wheels rotatably mounted on the carrier and rotated by the torque of the roller, and a friction clutch provided rotatably on the center shaft and associated with the carrier for swinging the carrier until one of the pair of wheels touches the ground.

Reference A10 to Williamson et al. discloses a convertible patient transport apparatus including a frame assembly adapted for supporting a patient. A plurality of bent pivot legs are attached to the frame assembly and mounted on respective wheels for rolling movement of the transport apparatus over a supporting surface. Each of the pivot legs includes a vertical upper portion, an intermediate portion formed at an angle to the upper portion, and a vertical lower portion formed with the intermediate portion. An actuator pivots the legs between an open position, wherein the distance between the lower portions of laterally adjacent legs is increased, and a closed position, wherein the distance between the lower portions of laterally adjacent legs is reduced. In the open position, the width of the transport apparatus is expanded to move the frame assembly over a bed of the patient. In the closed position, the width of the transport apparatus is narrowed.

Reference A11 to Kirmse et al. discloses a patient support apparatus that comprises a first support plate which can be transferred from an undercarriage onto a table frame of a medical apparatus. The table frame is provided with a second support plate which receives the first support plate directly, but enables an examination subject to be directly received on the second support plate without requiring the assembly of the first support plate.

Reference A12 to Hay et al. discloses a patient lift apparatus with a U-shaped base that folds to enable convenient reduced width storage of the unit when not in use. Accordingly, the U-shaped base of the unit has a hinge with a vertical axis in each leg of the "U". These hinges are located midway of each of the vertical legs. Typically, these hinges provide for a pivotal movement of the casters at the ends of each leg of the "U" from a caster extended position for patient lifting and transport to a caster folded position parallel to and spaced apart from the base of the "U". A releasable lock mechanism is provided to each leg for locking the hinge in either the caster extended position or the caster folded position. The lock includes an outer moving sleeve with a spring biased inner key connected to the spring biased sleeve. The key moves with the sleeve and fits into and out of paired apertures in the hinge. One aperture of the hinge is for maintaining the hinge in the caster folded position; the other aperture of the hinge is for maintaining the hinge in the caster extended position. In operation, an attendant moves the sleeve to unlock the hinge. Thereafter, and while the rest of the lift apparatus is supported at its respective casters, the outer leg member of the "U" is moved between the caster folded position and the caster extended position for patient transport.

Reference A13 to Anderson et al. discloses a flexible bathing fluid permeable mesh sheet attached to a rectangular frame. A flexible and collapsible bathing fluid impermeable sheet is attached to the frame below the mesh sheet and spaced apart therefrom for forming an open fluid receptacle. The mesh sheet is attached to the frame with straps which may be adjusted for allowing the patient to be placed substantially coplanar with the frame and away from the fluid collected in the impermeable sheet or lowered toward the impermeable sheet to provide an immersion bath.

Reference A14 to Schaal et al. discloses an improved patient transporting and turning gurney for receiving and lifting a patient from a hospital bed, for transporting and depositing the patient on a hospital operating table, and for lifting and turning a patient for surgery. Preferably, the gurney has a U-shaped base, this base of sufficiently small dimension to fit under a hospital bed and of sufficiently large dimension to straddle the sides of a conventional operating table pedestal. The gurney further includes an overlying stretcher support, preferably U-shaped, for supporting a rotatable stretcher frame. A longitudinally extending rotating stretcher frame is mounted for rotation about its longitudinal axis on the stretcher support. Extending from the U-shaped base to the overlying stretcher support, there is provided a lifting device for moving the stretcher support upwardly and downwardly relative to the base. A system of patient attachment to the stretcher frame is disclosed in which two tensile supported sheet members can be detachably supported from the frame.

Reference A15 to Thompson discloses a multi-position bed such as is used in hospitals and for persons who by reason of physical disability of age are unable to turn or move themselves in bed. As shown in FIG. 4 the bed comprises a base frame 1 supported on casters and having a pair of pivoted angled lifting arms 2. One of the pair of lifting arms is pivoted in turn to an interlink pivoted to a pivot bracket 4. The other lifting arm 2 is pivoted directly to a second pivot. The pivot brackets 4 and 5 act as the pivot supports for the center section 6 of a mattress platform which also comprises two side sections 7. The side sections 7 are not hinged directly to the center section but simply have interengaging features in the form of side frame registers 11. When the bed is used as a turning bed the interengaging features 11 disengage. The side sections 7 are carried by pairs of links 8 and 9 which join the pivot brackets 4 to the side sections 7 at points underneath the side sections. These side sections are also connected by side frame pivot arms 13 to an end pivot frame 12, at each end of the bed, the pivot frame 12 being rigidly connected to the center bed section 6. The movement of the bottom links 8 is restricted, in a downward direction, by bottom link stops 10. The links 8, 9 may be disconnected and the side sections 7 connected rigidly to the center section 6 so that the mattress platform can be caused to tilt bodily in a lateral sense.

Reference A16 to Lee discloses a hospital patient transfer system by a transfer trolley with a wheeled undercarriage. A lift ram is movable up and down with respect to the undercarriage and can also tilt about a horizontal pivot on the undercarriage. The lift ram supports an upper frame so that it can be raised, lowered or tilted in response to varying positions of the ram. The upper frame has parallel end pieces spaced from each other by a distance such that a hospital bed, operation table or trolley can be received between them. The end pieces of the upper frame are provided with lift members which can be raised or lowered with respect to the end pieces. A flat rectangular patient-supporting element can removably be inserted in opposed tracks in the end pieces so that it may be positioned below a stretcher supported by the lift members when they are in a raised position. The lift members can then be lowered to enable the weight of the patient to be taken by the patient supporting element.

Reference A17 to Smith discloses A patient lifting and transporting vehicle having a U-shaped base frame with four wheels, two telescopic tubes extending upward from the base frame, a rectangular upper frame provided with a removable strong transfer sheet for supporting a patient, said upper frame being fixed on the upper ends of the telescoping tubes, and operating mechanism comprising a lifting arm assembly hinged at its lower end to the base frame and at its upper end to a follower block slidable in one tubular side of the upper frame, said tubular side containing a drive screw engaging the follower block and crank-operated bevel gears for rotating the drive screw. When the upper frame is in its lowest position the lifting arm assembly lies at an angle of about 45° from the horizontal; as the lifting arm is moved, by the drive screw and follower block, toward a vertical position the upper frame is raised correspondingly to a highest position when the arm is vertical. Springs under compression in the telescoping tubes counter-balance part of the weight of the loaded upper frame. The location of the telescoping tubes on one side of the base frame and spaced from its ends enables the upper frame to be moved over a bed or operating table or into the range of an X-ray machine.

Reference A18 to Stryker discloses a wheeled carriage for supporting a patient and, more particularly, to a type of carriage having a vertically adjustable support frame upon which a stretcher can be removably placed for the purpose of safely supporting and transporting a patient disposed thereon in a horizontal or tilted position.

Reference A19 to Reichert et al. discloses new and useful improvements in hospital equipment and, more particularly, to a patient stretcher adapted for transporting patients from the hospital bed to a surgical operating room, X-ray room, or the like.

Additionally, references are known which relate to devices which are height-adjustable and/or capable of multiple positioning. These references include: (B1) U.S. Pat. No. 6,499,163, issued Dec. 31, 2002 to Stensby; (B2) FR Patent 2 789 302, published on Aug. 11, 2000 to Antar; (B3) U.S. Pat. No. 5,934,282, issued Aug. 10, 1999 to Young III et al.; (B4) U.S. Pat. No. 5,461,740, issued Oct. 31, 1995 to Pearson; (B5) PCT Publication No. WO 94/09738, published May 11, 1994 to Blanco GMBH & Co.; (B6) U.S. Pat. No. 5,187,821, issued Feb. 23, 1993 to Nieminen et al; (B7) PCT Publication No. WO 90/03158, published Apr. 5, 1990 to Oy AFOR; (B8) PCT Publication No. WO 89/02260, published Mar. 23, 1989 to Siegener Feinmechanik GMBH; and (B9) GB Patent Application 2 039 731, published Aug. 20, 1980, to Rogers.

Reference B1 to Stensby discloses an apparatus convertible to a chair or table comprises a support structure; first and second pairs of wheels rotatably supporting the support structure; and a platform supported by the support structure. The platform includes a seat support and a back support. The platform is positionable between a chair configuration and a table configuration. The first pair of wheels have inboard and outboard positions. The first pair of wheels are in the inboard position when the platform is in the table configuration. The first pair of wheels are in the outboard position when the platform is in the chair configuration.

Reference B2 to Antar discloses a modular gurney for transporting patients, the gurney has two or more rigid frame members (1, 2) each formed of two hollow tube sections connected by a honeycomb panel between a double skin (17, 17'). The gurney has a stainless steel plate (6,6').

Reference B3 to Young III et al. discloses a spine board for use in supporting a patient during emergency medical treatment comprising a pair of board joined together by a hinge. The hinge is provided with a latch which allows the board to be rigidly locked in a flat condition so as to provide rigid support for a patient receiving CPR or other treatment.

Reference B4 to Pearson discloses a multi-positional bed comprised at one end thereof with a pair of pillars. One of the pillars is disposed at or near each side of the bed and at the opposite end a single pillar is disposed substantially on the longitudinal center line of the bed. The bed has a user-supporting frame, and respective mounting devices for mounting the frame to each of the pillars. Each mounting device is arranged to move lengthwise with respect to the respective pillar independently of the movement of the other mounting devices.

Reference B5 to Blanco GMBH & Co. discloses a patient-transport trolley with a chassis (12) and a support frame (16) designed for a patient to lie on, the support frame (16) being held by a height-adjustable arm mounted on the chassis (12). In order to simplify the design, the invention calls for the trolley to include an arm with an elevating mechanism (14) with a parallelogram-type action, one end of the elevating mechanism (14) being held in a lower bearing block (28) on the chassis (12) while the other end is held by an upper mounting block (42) on the support frame (16).

Reference B6 to Nieminen et al. discloses a hospital bed comprising a body (4) provided with wheels, a transfer underlay frame (24) for a patient, a lying or resting frame (17), which can be lifted and lowered down, lifting means (30) for the lying frame, and bearer means (15, 20) for a transfer underlay frame; the bearer means comprise two U-shaped bearer rods (15) disposed side by side and turnable in the body, the upper and the lower arms (15b, 15c) of which are interconnected through articulated joints (18, 22) by a transverse support (16, 21) so as to secure a parallel turn of the arms aside. A bearer beam (20) is secured to the upper transverse support (21) and wheels (19) to the lower support (16). The invention allows a sideways transfer of a patient on a transfer underlay supported by straps (26, 28) secured to a bearer beam, without changing the direction. Wheels (19) provided in the bearer rods (15) move simultaneously to the same direction which ensures that the bed (2) is properly supported during all stages of the transfer.

Reference B7 to Oy AFOR discloses a treatment table (1) manufactured for the needs of physical care and rehabilitation in which the height of the treatment table and the position of the treatment level (20) are adjusted simultaneously by means of a single power device (5). The adjusting apparatus of the treatment table (1) comprises a power device (5), which is joined in a pivoting manner to the lower frame (2), lifting arms (7, 8), which are joined in a pivoting manner by their lower end to the lower frame (2) and the power device (5) and by their upper end to be upper frame (6) by means of pivoting fastening members (13), an extension arm (9), which is locked to be parallel with the lifting arm (8) when the position of the treatment level (20) and the height are adjusted simultaneously, and which said extension arm (9) pivots in relation to the lifting arm (8) when the treatment level (20) is moved in the vertical direction without the position of the treatment level (20) being changed.

Reference B8 to Sie-gener Feinmechanik GMBH discloses a couch with main components (1) a central part (5) arranged on a chassis (2) with running wheels and capable of being vertically lifted and lowered by a driving motor, and a plate for seating (6) hingedly linked to a head-rest (7) and to a leg-rest (8) that can be pivoted by means of a further driving motor up to a seating and to a lying position. In the area of an opening (10) of the seating plate (6) of the central part are arranged sanitary devices with a water supply for washing the body. A collection container (12) can be placed in an overflow tub (11) arranged underneath the seating plate (6) for receiving the excrements of a bedridden person and the washing water evacuated through the opening (10) in the seating plate (6). A mattress (13) of elastic material fitted to the form of the body and having an opening (14) that corresponds to the opening (10) of the seating plate (6) is removably secured on the couch (1).

Reference B9 to Rogers discloses an apparatus 1, FIG. 1, e.g. a nursing or orthopaedic bed, for supporting a patient comprises a rigid undercarriage 2 carrying a rigid frame 7 turnable, e.g. pivotable, about a horizontal axis. A further rigid frame 3 is slidably and/or removably supported on the frame 7 and can be releasably locked thereto by first locking means 100, FIG. 4. The frame 7 carries patient-supporting frames 4, 5 which are rotatable about a longitudinal axis of the apparatus through at least 180° and which can be releasably locked in one or more predetermined positions by second locking means 50.

Additionally, references are known which teach various support systems. These references include: (C1) U.S. Pat. No. 6,546,577, issued Apr. 15, 2003 to Chinn; (C2) U.S. Pat. No. 6,619,599, issued Sep. 16, 2003 to Elliott et al.; (C3) U.S. Pat. No. 6,375,133, issued Apr. 23, 2002 to Morrow; (C4) US Patent Pub. 2002/0162926, published Nov. 7, 2002 to Nguyen; (C5) U.S. Pat. No. 6,073,285, issued Jun. 13, 2000 to Ambach et al.; (C6) U.S. Pat. No. 5,987,670, issued Nov. 23, 1999 to Sims et al.; (C7) U.S. Pat. No. 5,611,638, issued Mar. 18, 1997 to Dörr et al.: (C8) U.S. Pat. No. 5,651,150, issued Jul. 29, 1997 to Kanitzer et al.; (C9) U.S. Pat. No. 5,687,942, issued Nov. 18, 1997 to Johnson; (C10) U.S. Pat. No. 5,699,988, issued Dec. 23, 1997 to Boettger et al.; (C11) U.S. Pat. No. 5,588,166, issued Dec. 31, 1996 to Burnett; (C12) U.S. Pat. No. 5,407,163, issued Apr. 18, 1995 to Kramer et al.; (C13) U.S. Pat. No. 5,117,521, issued Jun. 2, 1992 to Foster et al.; (C14) U.S. Pat. No. 5,016,307, issued May 21, 1991 to Rebar; (C15) U.S. Pat. No. 4,720,881, issued Jan. 26, 1988 to Meyers; (C16) U.S. Pat. No. 4,768,241, issued Sep. 6, 1988 to Beney; (C17) U.S. Pat. No. 4,489,454, issued Dec. 25, 1984 to Thompson; (C18) U.S. Pat. No. 4,262,872, issued Apr. 21, 1981 to Kodet; (C19) U.S. Pat. No. 4,273,374, issued Jun. 16, 1981 to Portman; (C20) U.S. Pat. No. 4,016,612, issued Apr. 12, 1977 to Barile, Sr.; (C21) U.S. Pat. No. 3,709,372, issued Jan. 9, 1973 to Alexander; and (C22) U.S. Pat. No. 2,696,963, issued Dec. 14, 1954 to Shepherd.

Reference C1 to Chinn discloses a mobile medical emergency and surgical table that comprises a frame assembly, a pair of mechanically advantaged undercarriage assemblies having wheels, a plurality of stretcher yoke assemblies, a plurality of preferably uniformly dimensioned and interchangeable storage cassettes, an electrical subsystem, and a plurality of optional mounts for the attachment of medical and surgical equipment.

Reference C2 to Elliott et al. discloses an intravenous (IV) support system including a moveable base and an upright IV pole. The base comprises a lower wheeled plate, an upper plate having a through hole, and an upright elongate tube fastened to the upper and lower plates. The tube is aligned with the through hole of the upper plate to form a passage for the IV pole. A bolt transversely extends through the wall of the tube to form a transverse supporting surface for the IV pole. The IV pole comprises, at a lower end thereof, a pin extending from a flange so that the IV pole may be fitted in a through bore of and supported by a mounting adapter mounted to a patient support frame. The system allows the IV pole to be easily transferable among numerous stand-alone bases and patient support frames, and steadily retained by the bases and mounting adapters mounted to the patient support frames without positive locking mechanisms.

Reference C3 to Morrow discloses an intravenous (IV) support assembly including a mounting adapter and an upright IV pole. The mounting adapter is mountable to a single rail of a patient support frame, and includes an insertion member and a locking mechanism. The IV pole is supported by the mounting adapter, and includes a hollow lower end for receiving the insertion member of the mounting adapter. The IV pole is secured to the insertion member by the locking mechanism of the insertion member. A variety of different mounting adapters each configured for a different rail configuration are available for supporting a common IV pole, so the IV pole is transferable between mounting adapters mounted to different rails.

Reference C4 to Nguyen discloses an apparatus for supporting medical fluids for delivery to a patient during surgery, in particular for fluids for intravenous delivery to the patient. The apparatus comprises a clamp for removably securing the apparatus to an object, such as a surgical table or bed, to allow the object to support the apparatus, the object being immovable relative to the patient to which the fluids are to be delivered. An arm is provided extending from the clamp. A support is connected to the arm remote from the clamp, the support being adapted to retain a receptacle containing medical fluids. In one embodiment, the arm is movable longitudinally with respect to the clamp, thereby allowing the position of the support with respect to the clamp to be adjusted. In a second embodiment, the arm is rotatable about the clamp such that the fluid receptacle support may be moved within a plane containing the longitudinal axis of the arm.

Reference C5 to Ambach et al. discloses a mobile support unit such as an IV stand or the like coupled to a mobile hospital bed, gurney or wheelchair by a latch mechanism which provides hands free operation thereby avoiding the need for a nurse or care provider to manually manipulate the latch to secure the units together for tandem transport. Further, the latch mechanism according to this invention includes a clutch which prevents relative movement of the IV stand or support unit with respect to the hospital bed during transport up to a specific adjustable torque level thereby avoiding the problem of the IV stand or support unit swinging freely relative to the bed during movement. Further, the clutch permits movement of the IV stand or support unit through an arc relative to the bed when a specified force is applied as required by the nurse or care provider to reposition the stand or support unit relative to the bed and provide increased access to the patient or the like. The IV stand includes a relatively heavy base which provides a low center of gravity for the unit and offers a very stabile mobile IV stand which resists tilting or tipping during transport.

Reference C6 to Sims et al. discloses a system for securing a wheeled pole, such as an IV pole, to an adjustable height mobile bed to form a movable assembly. The system includes a linkage element with first and second mounting blocks effective to secure the linkage element to an intermediate frame portion of the bed. An elastomeric member is extendable from the linkage element for engagement with a plurality of engagement members disposed on opposite sides of a channel formed in the linkage element. The elastomeric member effectively secures the IV pole in the channel for transport of the IV pole/bed assembly.

Reference C7 to Dörr et al. discloses a connecting device with at least two connecting elements fastened to the patient support and insertable into pin receivers of the column and carriage. Each connecting element has two latching elements each movable between a latching position and an unlatching position, and during relative movement between the transport carriage and the support column resulting in the transfer of the patient support from the column to the transport carriage, or the reverse, each connecting element becomes received at the same time in a column pin receiver and a carriage pin receiver. Each receiver has a detent recess for receiving one of the latching elements of a received connecting element in its latching position and a control surface associated with the other latch element of the received connecting element which control surface upon the reception of the connecting element transfers this latching element to its unlatched position. Each of the latching elements has associated with it a sensor for detecting the latching position of the latching element.

Reference C8 to Kanitzer et al. discloses a structure providing a patient support surface which is transferable between a stationary support column and a wheeled transport carriage with the transport carriage, the support column and the support surface providing structure having connecting parts which cooperate to securely hold the structure to the transfer carriage or to the support column when the structure is mounted on the transfer carriage or the support column, the connecting parts during transfer of the structure from the transfer carriage to a support column, or vice versa, being automatically moved between latched and unlatched conditions to allow the transfer to occur and having security features preventing the patient support surface providing structure from being inadvertently unfastened from both the support column and the transport carriage during a transfer procedure.

Reference C9 to Johnson discloses a support system for detachably mounting an article to a tubular support structure. The system includes a bracket plate having a key-way with side walls diverging from a front face of the bracket plate to a rear face thereof. The key-way extends entirely through the bracket plate between the front and rear faces and includes an entry mouth opening at an edge of the bracket plate. A support plate is adapted to be attached to the rear face of the bracket plate to close the key-way at the rear face. A mounting device mounts the bracket plate and attached support plate to one of the tubular members, with the key-way facing away from and extending longitudinally of the one tubular member. An elongated supporting key is adapted to be attached to the other of the tubular members lengthwise thereof. The supporting key is positionable into the entry mouth of the key-way and has side walls converging from a front face of the key to a rear face thereof for mating proximity to the diverging side walls of the key-way.

Reference C10 to Boettger et al. discloses a coupler clamping assembly (10) for releasably connecting a mobile support stand (52) with a patient transport device such as a gurney (54), in order to allow patient transfer with the support stand while eliminating the need for extra transport personnel. The clamp (10) preferably includes a pair of opposed, laterally spaced apart jaws (20, 22) interconnected by a central bight section (24). A connector assembly including a pair of oppositely extending elongated connection elements (14, 16) is supported on the body for relative pivotal movement, and the connection elements are received for rotation in a tubular section (66) conventionally provided as a part of the gurney (54). A clamping screw (18) is threaded for receipt in a threaded opening through one of the jaws (20) and cooperates with the opposed jaw (22) for securely clamping the upright standard (60) of the pole unit (52) within the clamping assembly (10). An arm assembly is also provided for permitting releasable interconnection between a mobile support stand and any type of patient transfer device. The arm may be fixed to the stand or transfer device, and includes an attachment clamp or coupling for releasably interconnecting the stand and transfer device.

Reference C11 to Burnett discloses a medical attachment device that is hung upon and rigidly attached to an upright and horizontally disposed part of a patient transport vehicle and that also grasps an upright pole of a wheeled patient care apparatus for maintaining the vehicle and the apparatus in fixed spatial relationship while both are being moved by a single medical attendant.

Reference C12 to Kramer et al. discloses a pole support for an IV pole mounted adjacent a patient support and having two pole supports separated by a pair of tracks providing guided paths between the two pole supports. The IV pole has a pole locking block at one end with pins that engage the tracks for slidingly moving the IV pole along the track between the two pole supports. The pins on the pole locking blocks further engage first slots and notches in the two pole supports for supporting the IV pole in a generally vertical position; and the pins engage second slots and notches in the two pole supports for supporting the IV pole in a generally horizontal position.

Reference C13 to Foster et al. discloses a care cart and a hospital bed having mating bases to permit the care cart to nest with the hospital bed. The combination of cart and bed can be rolled from place to place to transport the patient and the cart can be removed from the bed while maintaining the life support systems connected to the patient while the patient is transferred to another patient support.

Reference C14 to Rebar discloses a patient transportation apparatus comprising a stretcher and a collapsible pole for use in supporting IV sets and the like. The pole portion of the apparatus is adjustable in height with respect to the plane of the stretcher while being capable of being collapsed to a position below or equiplanar with the horizontal surface of the stretcher. The pole is located so that in all positions it does not extend beyond the perimeter of the horizontal surface. In another embodiment a lower support means is also provided for supporting gravity dependent drainage bags and the like.

Reference C15 to Meyers discloses an anesthesia accessories unit which is adapted to be placed and supported on an end portion of a patient's bed structure normally a hospital operating room table. The anesthesia accessories unit includes a primary tray assembly having the following items supported thereon or forming a portion thereof (1) a support hole assembly adapted to receive various syringe structures and other items therein in a neat and orderly fashion; (2) a headrest assembly adapted to receive a patient's head thereon in proper relationship to the drugs and medicine needed; (3) an instrument holder compartment adapted to receive instruments therein; (4) a drape frame assembly adapted to be erected over the patient's head and receive a surgical drape or cover member thereon in an elevated position relative to the patient's head; (5) a needle remover assembly allowing the anesthesia provider to remove covers and needle members with the use of only one hand; (6) an intravenous tubing holder assembly adapted to receive and anchor an intravenous tubing assembly; (7) an attachment assembly adapted to receive and hold various items such as tape, scissors, etc.; (8) a tube tree assembly adapted to receive air supply tubes and the like thereon to hold in an elevated condition; and (9) a transducer pole assembly adapted to attach a transducer member thereto which then is automatically moved with raising and lowering of the operating table structure. The intravenous tubing holder assembly includes a first tube holder adapted to receive an intravenous tubing therein and a stop cock holder operable to hold a stop cock therein so as to be readily operable by one hand of the anesthesia provider.

Reference C16 to Beney discloses a self contained, mobile intensive care bed structure adapted to carry a plurality of devices for monitoring and/or providing treatment to a patient in the bed structure and including built in direct current lines and outlets, communication lines and outlets, a pneumatic oxygen air and vacuum lines and outlets, and a direct current source, with the bed structure being operable in a stationary mode from fixed sources of d-c power, a-c power, oxygen, air and/or vacuum.

Reference C17 to Thompson discloses an apparatus for carrying a hemodynamic pressure transducer in a hospital bed so that the transducer is maintained in a constant relationship with the level of the heart of a patient in said bed, which comprises a first, vertical member for mounting said apparatus on said hospital bed, where said first vertical member is adapted to fit into a bracket provided on a hospital bed, and is further adapted to hold an intravenous feeding pole, so that said apparatus may hold an intravenous feeding pole as well as said hemodynamic pressure transducer; hinge means attached to and projecting horizontally from said first vertical member; a second member engaging said hinge means and disposed to project in a direction perpendicular to the axis of said first member; and a third, vertical member to which said transducer is adjustably but securely affixed. The bracket may be an intravenous feeding pole bracket provided on said bed. The first member may be mounted on a portion of said bed which is so selected that the relationship between the height of the transducer and the height of the patient's heart remains constant when the level of the bed is raised or lowered.

Reference C18 to Kodet discloses a pole attached to a hospital stretcher or the like for supporting an intravenous solution container. This pole has an improved collapsible construction attaching it to the stretcher so such pole does not interfere with any stretcher operation.

Reference C19 to Portman discloses a device for anchoring an upright pole or other supporting means used to support an intravenous bottle holder, particularly for use in an emergency vehicle, such as an ambulance. The anchoring device is particularly useful to secure the upper extremity of a pole to the vehicle inside roof surface, and in one embodiment of the device, a locking feature is provided with the anchoring device to prevent accidental disengagement of the pole and holder. The pole is typically mounted upon a platform, such as a cot used in emergency transport of patients, and with use of the invention, inconvenient and undesirable swaying of the pole and rotation of the holder is prevented, thereby minimizing a safety hazard to ambulance attendants and the patient.

Reference C20 to Barile discloses a bed frame especially suitable for a hospital bed construction. The bed rails are provided by one or more extruded metal channel members connected into a familiar rectangular frame. Extruded metal corner brackets are riveted to the corners of the frame. The corner brackets have integral extensions and formations which serve a variety of functions such as for supporting safety side rails and for the bed headboard and footboard members, standards for supporting patient treating equipment, among others. The bracket serves a dual function of strengthening and/or retaining the channel members in the rectangular frame formation and providing means for attaching a variety of different devices to the bed frame.

Reference C21 to Alexander discloses an apparatus for supporting intravenous supply bottles including an upright standard and a cross bar extending substantially horizontally across the top of the standard. An elongated cantilever spring secured to the standard extends to opposite sides of the standard beneath the cross bar. Reaches of the spring are adapted to press into tight frictional contact with upwardly facing ends of supply bottles depending from catches in the cross bar. A mounting for the standard permits vertical adjustment of the standard relative to a bed or other body support.

Reference C22 to Shepherd discloses a portable transfusion apparatus carrier, and more particularly to a carrier construction, which is removably attachable to a hospital bed or stretcher.

Lastly, references are known which disclose various devices for transport and/or transfer having exchangeable parts. These references include: (D1) US Patent Pub. 2005/0102748, published May 19, 2005 to Johnson; (D2) US Patent Pub. 2003/0213064, published Nov. 20, 2003 to Johnson; (D3) US Patent Pub. 2002/0174485, published Nov. 28, 2002 to Bartels; (D4) US Patent Pub. 2001/0044957, published Nov. 29, 2001 to Hodgetts; (D5) U.S. Pat. No. 6,101,644, issued Aug. 15, 2000 to Gagneur et al.; (D6) U.S. Pat. No. 5,487,195, issued Jan. 30, 1996 to Ray; (D7) U.S. Pat. No. 5,111,541, issued May 12, 1992 to Wagner; (D8) U.S. Pat. No. 5,014,968, issued May 14, 1991 to Lammers et al.; (D9) U.S. Pat. No. 3,902,204, issued Sep. 2, 1975 to Lee; (D10) U.S. Pat. No. 3,917,076, issued Nov. 4, 1975 to Campbell; (D11) U.S. Pat. No. 2,610,330, issued Sep. 16, 1952 to Sutton; and (D12) U.S. Pat. No. 2,512,160, issued Jun. 20, 1950 to Koenigkramer.

Reference D1 to Johnson discloses a transfer and transport device and method for moving a patient from a bed to another location within a medical facility. The transport device includes an integral transfer mechanism for transferring a patient from a hospital bed to the device and back.

Reference D2 to Johnson discloses a transfer and transport device and method for moving a patient from a bed to another location within a medical facility. The transport device includes an integral transfer mechanism for transferring a patient from a hospital bed to the device and back.

Reference D3 to Bartels discloses a patient support mechanism having a patient gurney for the delivery and removal of a patient, the patient gurney having a removable bed board, and having a stationary patient bed provided for the acceptance of the bed board or having a stationary supporting part provided therefor at an imaging medical system such as, for example, a CT installation, an angiography device or a NMR installation. The patient gurney has carriages that are transversely displaceable toward both sides for accepting the bed board and for shifting the bed board from the patient gurney onto the patient bed or onto the supporting part and vice versa. A patient gurney having two double T-shaped supports that are centrally connected to one another by a longitudinal support.

Reference D4 to Hodgetts discloses a patient transport system for transporting a patient from a bed to a stretcher or vice versa, using a bed sheet and a conveyor attached to the bed or the stretcher. A first end of the sheet is removably attached to the conveyor and a second end of the sheet is free. The sheet is adapted to be positioned onto the patient supporting member of the bed or stretcher. The conveyor includes a roller received by bearings. The roller can be removably received by the bearings. The roller can also include a telescopic arrangement so that its length can be adjusted. A pawl and ratchet assembly can be provided on the conveyor to prevent unwinding of the conveyor. The sheet is removably attached to the roller by adhesive tape or a clip arrangement. A flexible belt attaches the clip to the conveyor and is removably secured to the roller. The clip includes a body member having a recess with a plug received therein.

Reference D5 to Gagneur et al. discloses a transport cart/patient table system for transferring an exchangeable slab of the patient table, which slab can be moved by means of a lifting arrangement, between the table and the transport cart, whereby the transport cart is moved under the patient table for the transfer of the exchangeable slab, has a first guide arranged on the transport cart and a second guide arranged on the patient table, which can be brought to engage one another as the cart is moved under the table. The guides engage in such a way to allow the transport cart to be pivotable and to be displaced longitudinally, while the engaged guides serve to guide the transport cart.

Reference D6 to Ray discloses an apparatus for lifting and transporting a prone patient comprising a mobile base frame that may extend under the patient's bed, a vertical support structure mounted along one side of the base frame, a pair of cooperating patient supporting plates connected to the support structure, the first supporting plate is horizontally oriented and may be lowered onto the bed and slid partially under a prone patient who has been rolled slightly to the side away from the support structure, after rolling the patient in the opposite direction towards the support structure and upon the first supporting plate, the second supporting plate is pivoted downwardly onto the bed into alignment with the first supporting plate, and the patient is rolled away from the support structure onto the second supporting plate. A sling may assist positioning the patient relative to the supporting plates.

Reference D7 to Wagner discloses a gurney, or hospital cart, that is characterized as being made predominantly of materials that are non-metallic, non magnetic, and of low electrical conductivity. Such a feature is of particular importance in those health care facilities wherein modern non-invasive body scanning equipment is in use, such equipment as provides imaging based on NMR, MRI, and the like, especially wherein large-scale superconducting magnets are in use.

Reference D8 to Lammers et al. discloses a patient table having round surface edges for coupling between a trolley and a patient table for the transfer of a table top from the trolley to the patient table. When the patient table is lifted by a table lifting mechanism, the table top is decoupled from the trolley after which the trolley can be decoupled from the patient table so as to be removed. The lifting construction of the patient table enables a large stroke to be made in a vertical direction without giving rise to longitudinal displacement of the table includes top. The patient table a hydraulic displacement mechanism for a longitudinal displacement of the table top; this mechanism can also be operated by hand in the case of emergencies.

Reference D9 to Lee discloses a hospital transfer trolley comprising a main frame from which two parallel end pieces extend at right angles so that a bed, trolley or the like can be received between the end pieces. A pair of horizontal lift members are carried by the end pieces and can be raised or lowered with respect to the end pieces. A couch including a mattress and a mattress support is movable between a horizontal patient-supporting position in which it is between the end pieces and an upright inoperative position on the main frame. The mattress support is engageable with the lift members when the couch is in its patient supporting position to enable the couch to be raised and lowered.

Reference D10 to Campbell discloses trolleys and in particular a trolley for handling patients on a stretcher where in certain instances it is essential that the patient be moved as little as possible. Accordingly the important features of the trolley are a base frame on wheels, a stretcher support spaced from and above the base frame and means for raising, lowering and tilting the stretcher support relative to the base.

Reference D11 to Sutton discloses improvements in wheeled tables for transferring invalids.

Reference D12 to Koenigkramer discloses a physicians' carriage or litter for professional use in the treatment or diagnosis of human ailments.

While the prior art discloses several individual features ultimately incorporated in the instantly disclosed PS3, the references nevertheless fail to disclose or suggest the combination of features as taught and claimed herein. For example, referring to Reference D10 (U.S. Pat. No. 3,917,076) which discloses a cantilever frame, the reference fails to teach or suggest a bed-to-frame interface construction and function, wherein a fail-safe mechanism is included for prevention of unwanted folding of the bed during transport, which is a critical component of the PS3 design. This anti-folding fail-safe mechanism renders the PS3 unique over the prior art cited. Additionally, auxiliary components such as the wing and frame construction, and the adjustable IV pole holder have not heretofore been disclosed in the prior art.

SUMMARY OF THE INVENTION

The Patient Single Surface System is a system solution which represents the next generation in patient accommodation, diagnosis, treatment, transfer and transport. PS3 provides a single surface for the patient to remain on from the trauma site through diagnosis, treatment and convalescence. PS3 addresses the long-felt needs of providing improved patient treatment through reduction in time to treatment; reduced or eliminated unnecessary patient movement and injury as well as improved comfort throughout treatment and convalescence.

In addition, PS3 addresses significant economic considerations. Economic considerations include elimination of costly hospital staff injuries during patient transfers, up to six to one (6:1) reduction in hospital staff required for patient transfers, increased patient throughput and improved long term patient outcome/reduced healthcare costs for patients benefiting from reduced time to treatment and/or unnecessary disturbance elimination, and improved long-term hospital staff retention.

PS3 is comprised of four major systems: (1) a single surface support (or patient single surface, (2) a single surface to frame interface, (3) auxiliary accommodation features and modules and (4) a cantilever transfer and transport frame. PS3 novelty lies in multiple features within each of the major systems.

The PS3 patient single surface platform, a contoured thin, rigid bed-type surface for transfer requires only a single person, regardless of patient weight, to position the unit above the surface for transfer, and then lower them mechanically with the cantilever frame. No lifting/pulling/pushing of the patient is required. No additional personnel are required, even for completely incapacitated patients. This is quite contrary to the historic and current patient transfer method with a bed sheet or thin plastic sheet, which requires between four and six personnel for incapacitated patients depending on patient size and personnel available. With rare exceptions, current methods are entirely a manual process, which requires significant lifting, pushing and pulling. In addition, PS3 single surface design and unique auxiliary equipment accommodation allows for the patient to remain connected and auxiliaries unmoved throughout a transfer (unless removal is required in an MRI or similar equipment). Numerous design features of the PS3 frame to single surface platform interface, the thin frameless segmented single surface platform and the modular auxiliaries are novel, which add significant usability, minimize complexity and greatly increase its range of application over prior designs. In addition, the PS3 single surface platform is unique in its ability to provide superior comfort/accommodation for patient rest during critical treatment periods.

PS3 provides a single surface for the patient to remain on from the trauma site through all diagnosis, all treatment and convalescence. PS3 accommodates the widest range of application with the least modification to interfacing equipment when compared to existing devices/prior art due to its inherent design and modularity.

Accordingly, it is an objective of the instant invention to provide a frameless single surface system (PS3) for patient accommodation, diagnosis, treatment and transfer, which eliminates the current practice requiring multiple manual patient transfers.

It is a further objective of the instant invention to provide a patient transfer system which incorporates efficient, safe, passive and secure single surface to frame interface, mated to a cantilever frame, which includes self-aligning features and an ability to withdraw horizontally once mated to another surface.

It is an additional objective to provide the PS3 with a segmented support surface (PS3 bed) containing a segment interlock functionality for maintaining rigidity of the frameless PS3 single surface platform, when desired, wherein segment articulation of the frameless single surface is not permitted to occur without proper mating surface support and engagement of the positive mating means, e.g. T-Pin engagement.

It is a further objective of the instant invention to provide means for efficient width adjustment, e.g. in the form of readily attachable segmented components or "wings" which interlock with lateral edges of the PS3 single surface platform thereby enabling scalability in the PS3 single surface platform width, with no loss in PS3 single surface platform functionality, or alternatively, in the form of multiple fixed width options.

It is another objective of the instant invention to provide a cantilever transport/transfer frame which allows greater and more stable range of height adjustment, and provides support arms which enable both Trendelenburg and reverse Trendelenburg tilt.

It is still a further objective of the instant invention to provide a cantilever transport/transfer frame which enables full articulation of the PS3 single surface platform segments while supported thereon.

It is yet an additional objective of the instant invention to provide a cantilever transport/transfer frame which enables reversible cantilever via centrally located support columns, and which provide arms and/or columns with rotatable and translatable functionality.

It is still an additional objective of the instant invention to provide a PS3 single surface platform articulation enabling interface effective for inclusion with standard gurneys.

Yet an additional objective of the instant invention is the provision of a PS3 single surface platform to mating surface interlocking design.

An additional objective of the instant invention is to provide components of the PS3 system with a matable, full length, receiving surface to enable universal and infinitely adjustable engagement of PS3 auxiliaries and wings thereto.

Still a further objective of the instant invention is to provide the PS3 system with quick-locking and single-handedly removable auxiliaries and width adjustment components.

A further objective of the instant invention is to provide a PS3 auxiliary block with a stepped holed design to accommodate multiple pole/interface sizes, and additionally providing a Poke Yoke design to insure proper insertion orientation for locking.

Still another objective of the instant invention is to provide an auxiliary block having a 2 stage release handle to allow for release of auxiliaries, while preventing accidental release from the Single Surface.

Yet another objective of the instant invention is to provide the PS3 system with a separate articulation inter-lock module which is installable/removable while the frameless single surface is suspended in the PS3 frame.

It is an additional objective of the instant invention to provide the PS3 single surface with a multiple layer non-continuous air mattress which is rapidly adaptable to improve patient comfort.

Other objects and advantages of this invention will become apparent from the following description wherein, by way of illustration and example, certain embodiments of this invention are set forth.

BRIEF DESCRIPTION OF THE FIGURES

FIG. 79 is an perspective view of the "external" self-catch auxiliary block and an alternative single surface platform rail;

FIG. 80 shows an perspective view of an "internal" engagement self-catch auxiliary block aligning to mate to an alternative single surface platform rail design with a slot or appropriately sized through hole;

FIG. 81 is an perspective view of the "internal" engagement self-catch auxiliary block of FIG. 80 mated to an alternative standard rail design with a slot or appropriately sized through hole;

DETAILED DESCRIPTION OF THE INVENTION

Figure 1:
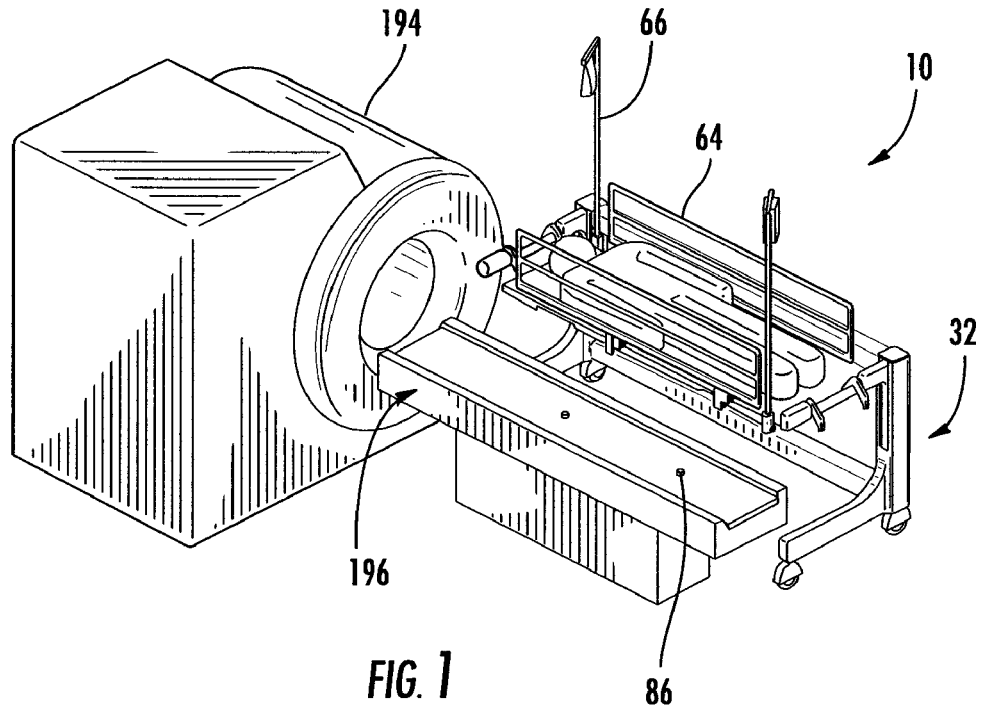
FIG. 1 is a perspective view of the PS3 system depicting the initial step of alignment of PS3 as the patient is transported to a MRI lab and initially positioned next to a MRI bed.

The Patient Single Surface System (PS3) provides an all encompassing, systematized approach to patient transport and care, representing a paradigm shift from current systems and methods.

PS3 has been designed to provide a fully modular and scalable system based upon the provision of a single surface upon which a patient may remain beginning at a trauma site and extending throughout the steps of diagnosis, treatment and convalescence.

The origins of the PS3 concept emanated from a study of stroke victim care in which studies indicated that up to 16 patient transfers were required for treatment, which corresponded to a loss of 20-40 minutes required for these manual transfers. The deficiencies of current patient care systems thus necessitate frequent movements which detract from efficient care and often tax the abilities of all involved, including the patient, caregivers (such as doctors, nurses, orderlies, attendants and paramedics), and the institutions for whom they serve, including hospitals, emergency medical services and health insurance providers.

Implementation of the PS3 system will provide myriad benefits, such as reduced time to treatment for all immobilized patients (e.g. stroke or acute coronary syndrome patients, where time lost translates into irreversible loss of function); elimination of unnecessary disturbance of acute care victims, such as those suffering spinal injuries; and improved patient comfort during diagnosis, treatment and convalescence.

Implementation of PS3 will also serve to enhance economics related to patient care by eliminating patient transfer associated hospital staff injuries during patient transfer (which is estimated to have a direct cost in the range of $28-$128 million annually), eliminating patient injuries during surface transfers, reducing staff requirements for patient transfers by as much as 6 to 1, improving long-term outcome and reducing healthcare costs for patients benefiting from reduced time to treatment, improving long-term hospital staff retention and improving patient throughput.

The PS3 has been designed to provide a wide range of application across a broad spectrum of patient treatment from trauma through convalescence, in a scalable and modular format. PS3's design requires little modification to existing interfacing equipment, while providing a multiplicity of safety interlocks using simple and readily adapted mechanisms.

The heart of the PS3 system is the frameless single surface platform which may be formed in 2-3 segments to provide articulation of a backrest portion and, optionally, a knee gatch. Although some loss of functionality may occur, it is nevertheless contemplated to provide full or partial framing, as need may dictate, for particular applications. The single surface platform or bed is designed to be lightweight, thin and modular, and may incorporate a wing system to provide for scalability in width, as required. In a preferred embodiment, a self-aligning self-locking quick release wing construction is provided to rapidly adapt the PS3 single surface platform to width requirements dictated by either patient comfort requirements, equipment space requirements or the like. In a particularly preferred embodiment, the wing attachments are additionally provided with a tension lever to insure tight fit to a single surface, while simultaneously acting as a fail-safe mechanism to prevent inadvertent disengagement. When desirable, and in order to reduce the number of loose parts, it is contemplated to fabricate the wings in a multiple segment hinged embodiment.

In an alternative embodiment, as opposed to scalable wings, a multiple width integrated solution may be provided, wherein a particular width PS3 single surface platform is initially chosen based upon anticipated needs. This embodiment serves to eliminate a proliferation of loose parts, e.g. wings, however it may necessitate a transfer of the patient to an alternatively sized PS3 single surface platform, as may be required.

The PS3 single surface platform is designed to facilitate compatibility with MRI and X-ray imagery equipment, as well as providing an easily adaptable platform for usage by emergency medical services personnel.

In a particular embodiment, the PS3 single surface platform can be provided with an inflatable air mattress for enhanced patient comfort. This mattress may be provided with multiple layers including a foam or gel overlying an impervious layer or an alternative self-healing layer analogous to a basketball self-healing membrane overlying a plurality of air chambers. The air mattress provides a means for rapid adaptation to various conditions experienced as the patient progresses from trauma through diagnosis, treatment and convalescence. Inflated on-demand by a small compressor in the frame, separate stand or auxiliary tray on PS3. This multi-layer air mattress is an alternative to continuous air systems which require constant power supply, constant connection to the fan system, are noisy and more maintenance intensive due to the constant run nature.

The second major component of the PS3 system is the single surface to transfer frame interface, which provides rapid transfer, is self-aligning, secure, of passive design and is designed to provide both Trendelenburg and reverse Trendelenburg positioning. In an illustrative, albeit non-limiting embodiment, the frame to single surface platform interface is further provided with one or more tabs which are designed to rotate or translate to a position above the single surface platform-to-frame interface to provide additional security. Contrary to prior art devices, the instant invention permits horizontal withdrawal of the frame to single surface interface, without requiring that the components drop below the mating surface for disengagement.

The third major component of the PS3 system is encompassed in the provision and accommodation of auxiliary components. Auxiliary components such as guard rails, IV pole holders, and the like are attachable to the PS3 support surface anywhere along the periphery of the support surface, utilizing the same self-locking features as the auxiliary blocks and wings, and need not be attached and reattached during patient movement from one area of treatment to another. The auxiliaries are designed so as not to extend below the PS3 or wing surface, thereby ensuring that the auxiliaries can be removed while the PS3 is mated to another surface.

In a preferred, albeit non-limiting embodiment, provision of a unique auxiliary block having a self-locking and quick release design enables enhanced ability for attachment of auxiliary devices. The system's modular design permits quick self-aligning attachment of all auxiliary components to a variety of modular components such as the PS3 surface support platform and/or the wings. By use of the scalable wings, along with an auxiliary block which incorporates a unique two-step locking mechanism, secure assemblage of specifically needed surface structure and auxiliary implementation can be readily achieved.

APPLICATION EXAMPLE

In an illustrative example, a patient will initially be assessed by EMS personnel and placed upon a PS3 patient surface platform or "PS3 bed". Auxiliary components such as an IV bag carrying fluids to the patient may be attached thereto. Self-lock, quick release transfer hooks may also be applied to the PS3 single surface platform along with the adjustable width self-storing handles and the single surface platform may be affixed to a wheeled carrier for transfer to the hospital emergency room. Once within the ER, a backrest and mid-section self-locking wing might be installed to enhance patient comfort. Additionally, guard rails may be secured along the peripheries of the PS3 single surface platform to provide enhanced patient security, while still enabling articulation for patient treatment and comfort.

Once within the hospital, the transfer frame can be positioned for engagement with the PS3 single surface platform. Utilizing the self-aligning features inherent in the single surface platform-to-frame interface, safe and secure transfer may be easily accomplished, thereby enabling removal of the wheeled carrier. Upon positioning of the PS3 single surface platform upon the transfer frame, the patient may be easily moved throughout the hospital for necessary tests and the like. This transport may be carried out in a horizontal mode or, by vertically orienting the support structure of the transfer frame, in the Trendelenburg or reverse Trendelenburg position, as desired.

In an illustrative embodiment, as will be further described below, the patient, while resting on the PS3 single support surface which is interfaced with the transfer frame, is first transported to the vicinity of an MRI device. The patient is then transferred directly to the MRI device, while always remaining on the PS3 single support surface.

The only modification required of the MRI device is the installation of an appropriate number of "T-pins" (usually two) to couple to the PS3 single surface platform. The entire patient support surface is positioned above the MRI scan bed, and once nominally positioned, any guard-rails or auxiliaries may be dismounted and stored on a separate rack or mounted to T-slots, or the like matable receiving surface, built into the MRI transfer frame. The quick-release Mid/Lower leg wings and guard-rails can then be removed, as well as the quick-release backrest wings and associated guard-rails. At this point the PS3 single surface support is lowered onto the MRI bed and self-positioning openings guide the T-pins into place as the patient support surface is lowered thereon. When fully supported upon the MRI bed, the PS3 transfer frame may be removed. Subsequently, the PS3 support surface is locked to the MRI bed by activation of the single handle which translates the locking mechanism, simultaneously interlocking about the T-pins, and releasing the locking elements which had prevented articulation of the backrest and knee gatch joints, which had maintained the PS3 support surface rigid. If necessary, auxiliaries may remain fixedly engaged to the MRI bed, while still enabling insertion of the patient within the MRI device.

Alternatively, when space within the MRI or CT scanner becomes problematic, the PS3 single surface platform may fully replace the imaging bed of the scanning device. In such an embodiment, the MRI or CT scanner will engage the PS3 in a side-drive configuration, wherein the matable receiving surface, e.g. the T-slot, is directly engaged by mating means made integral with the MRI/CT scanner. This allows elimination of the extra thickness caused by stacking of the PS3 and MRI/CT scan bed, and allows for removal of the articulation inter-lock module (which allows for improved imaging) and does away with the need for the T-pins.

With reference to the PS3 single surface support platform or "PS3 bed", the design is configured to initially provide a rigid backboard facility. Means are provided to maintain the segmented surface in a rigid configuration, e.g. by the use of spring loaded locking tubes, which are biased to a home position which insures positive engagement of adjacent segments, thereby precluding relative articulation therebetween, e.g. about the back rest or knee gatch articulation points.

An articulation inter-lock module is provided which is positionable within the confines of the PS3 single surface platform, in a manner such that translation of the articulation interlock module securement means can only be accomplished subsequent to insertion of the T-pins within the T-pin reception means, at which point the articulation inter-lock blocks securely grasp the T-pins and simultaneously disengage the means providing rigidity of the segments to a second position, whereby articulation of the segments is enabled. Thus, when mounted to an underlying surface which permits of articulation, the knee gatch and backrest may be adjusted for most efficient treatment and patient comfort.

An additional feature of the PS3 system is illustrated in the PS3 auxiliary block mounting mechanism. This mechanism is designed to securely mount within a matable receiving surface, which is ubiquitous to various members of the PS3 system. In a preferred, albeit non-limiting embodiment, the matable receiving surface is depicted as a T-slot. The T-slot may be provided in the sides of the PS3 single support surface, the transfer frame, the scalable wing system, and the various manifestations of guide-rails. By utilizing a combination of male/female coupling configurations, the component mounting system provides a self-locking and self-aligning attachment system which is infinitely adjustable within the mounting surface. Spring biasing means, or the like, provide for easy and quick release of mounted components, while, in a preferred embodiment, providing a supplemental locking element which provides for a secure fit and fail-safe attachment, thereby preventing inadvertent disengagement. Unique to the auxiliary mounting block, is a locking element incorporating a two-stage quick release feature. As illustrated below, this locking element provides for self-locking of the auxiliary block to a mounting surface and also self-locking of an auxiliary feature, e.g. an intravenous support pole (IV pole) within the auxiliary block. Application of force to the release mechanism to a first release point enables release of the IV pole, without any release of the auxiliary block form the mounting surface. Continued application of pressure to a second release point is effective for disengagement of the auxiliary block from the associated matable receiving surface.

In an alternative embodiment, a modification of the PS3 support surface is provided which enables articulation and actuation of both the knee gatch and backrest incline while the PS3 support surface is engaged with the PS3 Frame, in addition to Trendelenburg and Reverse Trendelenburg within the PS3 Frame. This modification, in addition to allowing backrest incline and knee gatch articulation while in the PS3 frame, further permits improved access to both sides of the PS3 single surface platform when in "Bed/Gurney" mode (at rest or transport) and support of PS3 Single Surface when suspended in the PS3 Frame, which allows for easier installation/removal of the Articulation Interlock Module. This support embodiment heavily reduces the chance of binding and force required to install/remove the Articulation Interlock Module.

Two major approaches for this embodiment are contemplated, a first embodiment wherein a full width version with full low profile frame is provided which stays attached to the frame at the main single surface platform to frame interface hooks. This embodiment utilizes conventional gurney backrest incline actuation which is usually pneumatic shocks which stay within the frame height. The knee gatch is also actuated by typical gurney means within the frame height. This embodiment would require one transfer to narrow width version of PS3 if need for MRI/CT scan. It is noted that the T-pins and keyhole lock modules would still be used to lock PS3 into another surface, but the interlock for backrest and knee gatch articulation would not be necessary. In a second embodiment a two column mid cross-bar version is provided, wherein one version has "head" end and leg end "specified" and a more complicated version which is not specific with regard to the head end versus the leg end of the single surface platform with respect to frame. In this embodiment, the frame cross bar may be moved laterally to a middle position, irrespective of the backrest/knee gatch articulation within the frame, thereby improving side access within the frame.

In order to fully explain the various features, of PS3, its auxiliary components and alternative embodiments, reference will now be made, in detail, to the accompanying figures, wherein like elements are uniformly numbered throughout.

With regard to diagnostic interfaces, the MRI is thought to be the most difficult, primarily due to its package constraints and very narrow patient platform. The MRI also adds a challenge through the requirement that any interface equipment is of nonferrous material, which the PS3 design facilitates.

Figure 3:
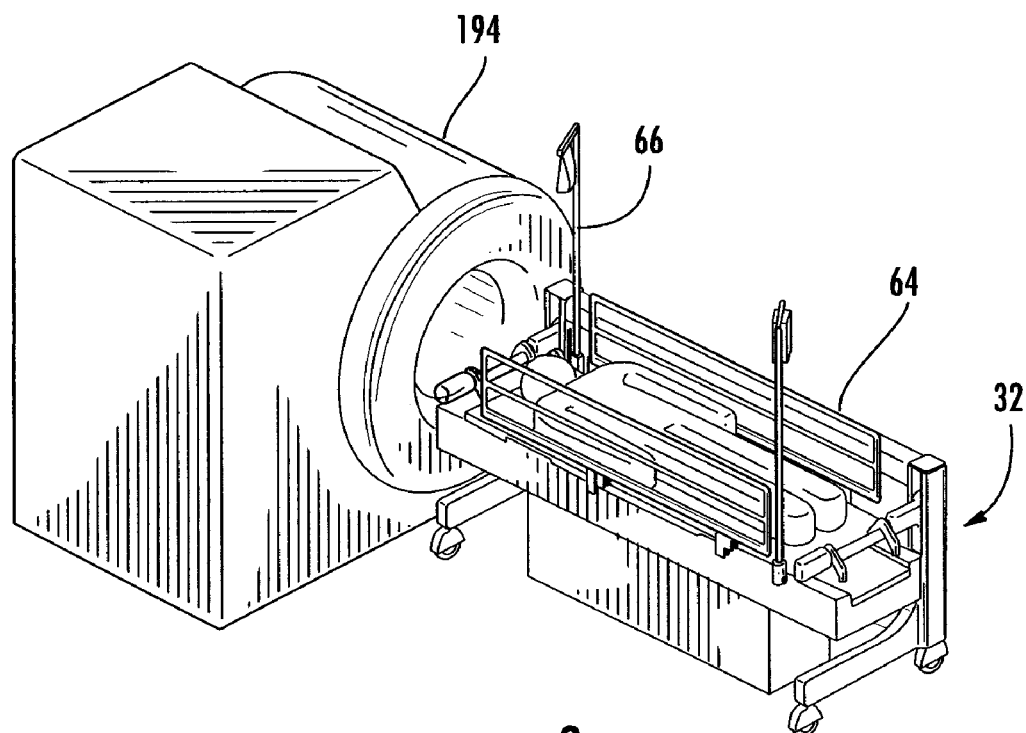
FIG. 3 is a perspective view of the PS3 system depicting the step of lowering the PS3 single surface platform into position with cantilevered arms to a safe distance just above (~1 inch) the MRI bed.
Figure 4:
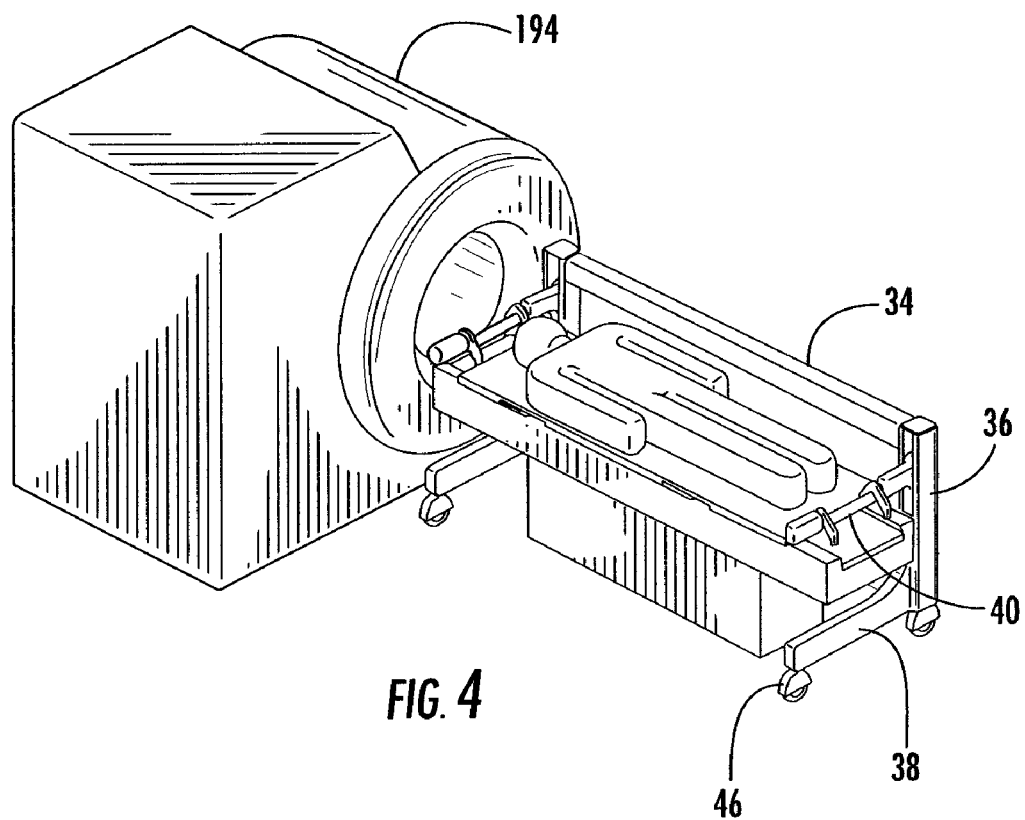
FIG. 4 is a perspective view of the PS3 system depicting the next step wherein the quick release guardrails, the quick release auxiliary blocks and poles are removed.
Figure 5:
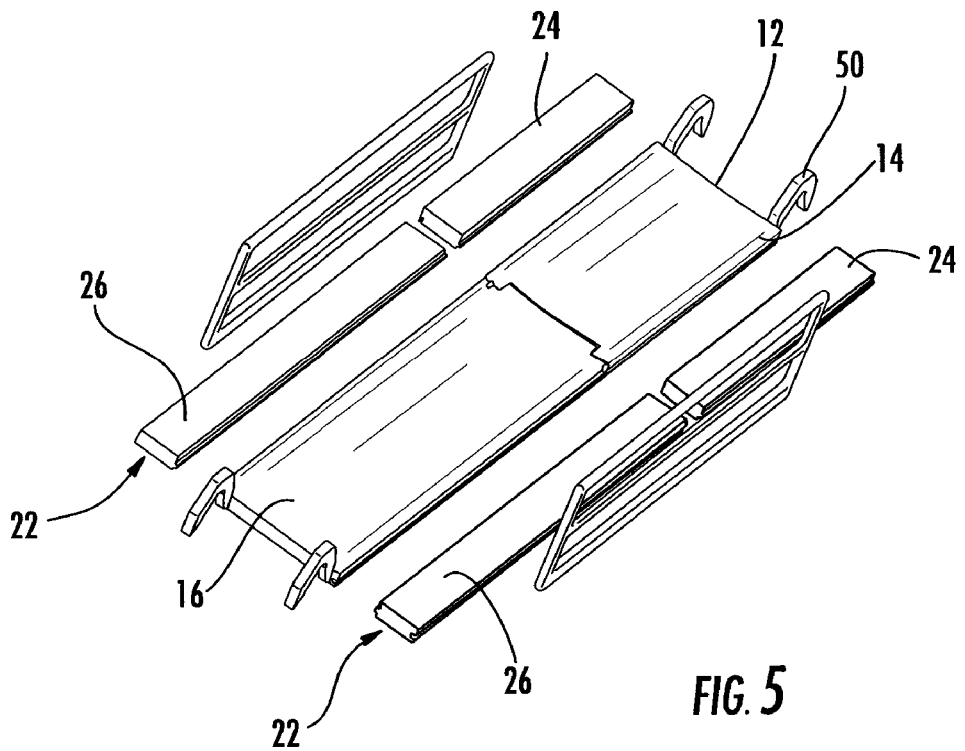
FIG. 5 is an exploded view of PS3 single surface platform, wings and guardrails.
Figure 6:
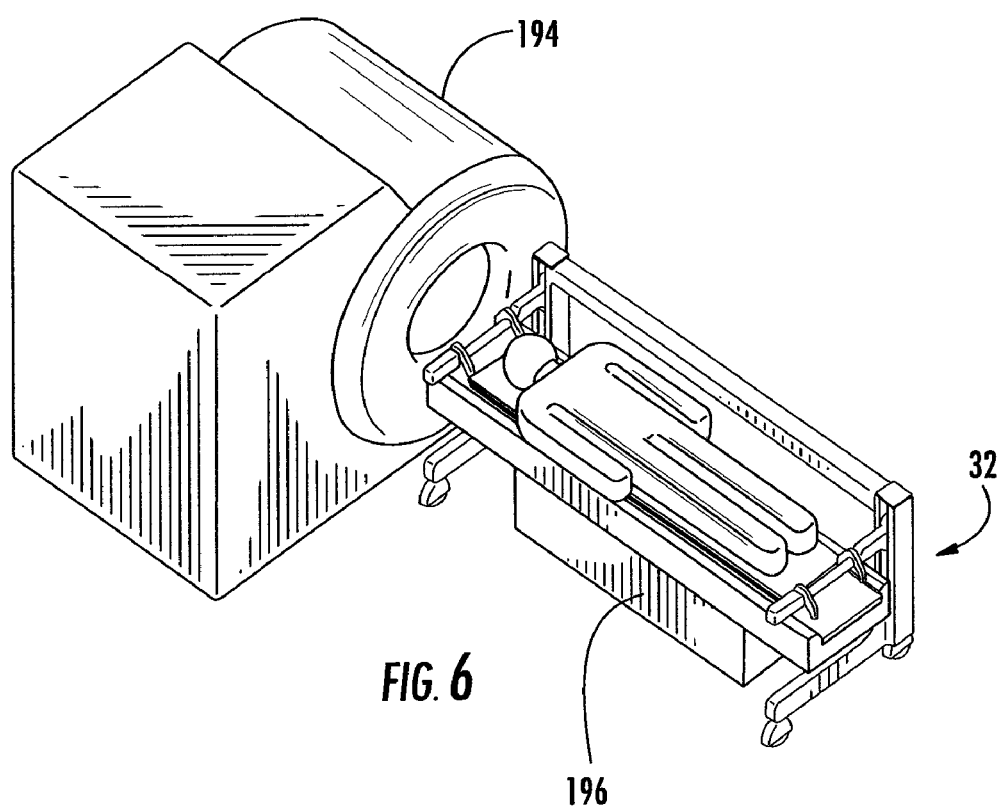
FIG. 6 is a perspective view illustrating the PS3 system with the single surface platform wings removed to accommodate a narrow MRI bed.
Figure 7:
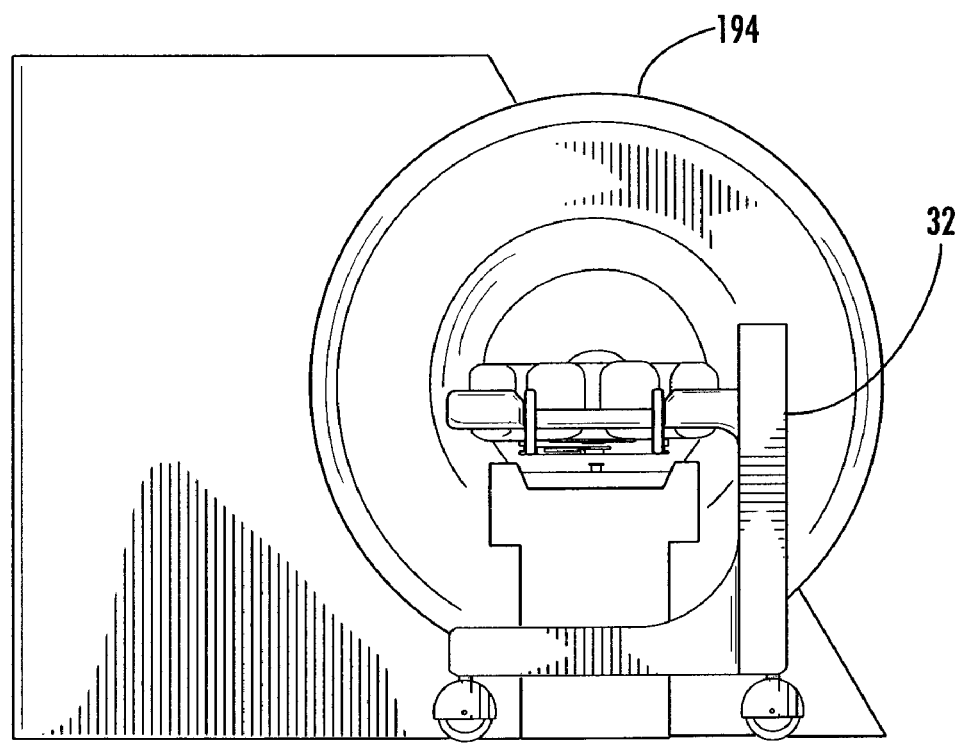
FIG. 7 is an end view of FIG. 4, with the quick release single surface platform wings removed to accommodate a narrow MRI bed, also locking T-pins are shown on the MRI bed.
Figure 110:
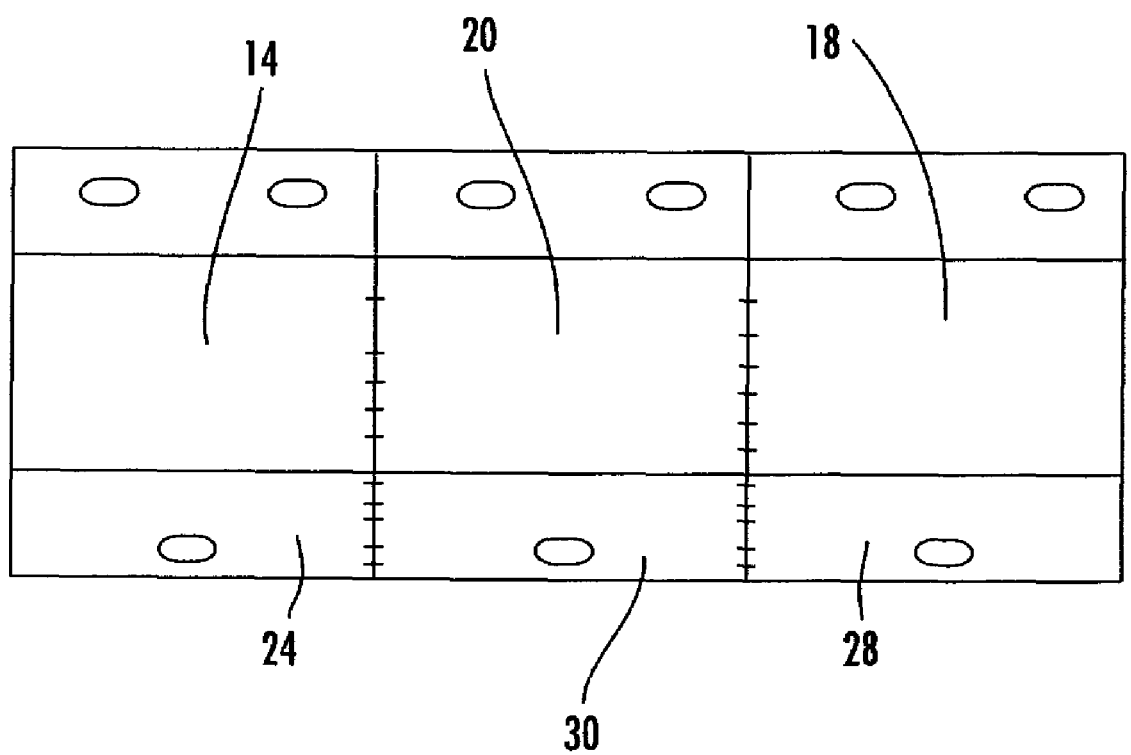
FIG. 110 is a top plane view of the PS3 single surface platform incorporating an upper body section hinged to a mid section which is hinged to a lower leg section. Separate wing sections are illustrated on the top portion of the FIG. and hinged wing sections are illustrated on the lower portion of the FIG.

Now with particular reference to FIGS. 1-10, a stepwise example of use of the PS3 system in conjunction with an MRI is described. PS3 design features that facilitate each step are shown as well in the following MRI example. The heart of the PS3 system is a frameless single surface platform 12 which may be formed in 2-3 segments to provide articulation of a backrest portion 14 and an optional mid portion and knee gatch of sections 20 and 18 respectively (FIG. 110). The single surface platform is designed to be lightweight, thin and modular. A wing system may be incorporated onto the single surface platform for scalability in width. In an embodiment a self-locking, quick release wing system 22 is provided to adapt the single surface platform 12 to width requirements dictated by either patient comfort requirements, equipment space requirements or the like. As illustrated in FIG. 5 wing sections 24 may be attached to one or both sides of the backrest portion 14 of the single surface platform. Also, wing sections 26 may be attached to one or both sides of the lower portion 16 of the single surface platform. As shown in FIG. 110 wing section 28 may be attached to one or both sides of the knee gatch portion 18 of the single surface platform and wing section 30 may be attached to one or both sides of the mid portion 20 of the single surface platform. Wing sections can be attached to each other to further increase the width of the platform. For example, 2 or more wing sections 24 and/or 26 can be attached to one or both sides of the single surface platform in FIG. 5.

With reference to FIG. 1, a perspective view is shown depicting the initial alignment of PS3 single surface platform 12, while supported upon the transfer frame 32, as the patient is transported to the MRI lab and initially positioned next to the MRI device 194 upon the extended MRI bed 196. Initially usage of PS3 simply involves the transport of the patient on the PS3 apparatus 10 to the MRI lab, as one would do on a standard gurney. Modes of operation for vertical raising and lowering or Trendelenburg motion are through either electromechanical means, hydraulic or pneumatic means. FIG. 1 illustrates step of raising the PS3 platform into position by either electromechanical means, hydraulic or pneumatic means. Also, the initial alignment of PS3 and patient next to the MRI bed. Note the placement of means for securing the PS3 platform 12 to the MRI bed, herein illustrated as T-pins 86.

FIG. 1, illustrates the steps of raising the PS3 Single surface platform into position by either electromechanical means, hydraulic or pneumatic means and then translating the PS3, by pushing it into position above the MRI bed.

Figure 2:
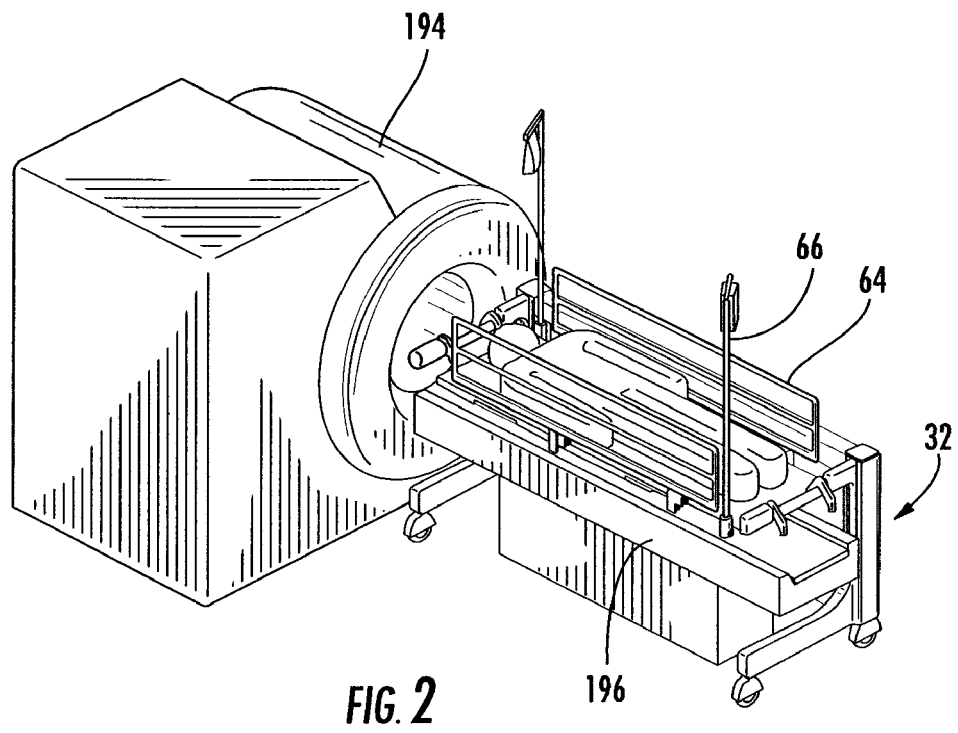
FIG. 2 is perspective view of the PS3 system depicting the next step of raising the MRI Bed into position then pushing PS3 system into position above the MRI bed.

As further illustrated in FIG. 2, the PS3 single surface platform is next lowered into position by vertical translation of the cantilevered arms or single surface to frame interface 40 of the transport and transfer interface frame 32 to a safe distance just above (~1 inch) the MRI bed. Note that the quick release guard rails 64 and auxiliaries 66 remain in place.

Regarding FIG. 3, illustrated here is removal of the quick release guardrails 64 and auxiliaries 66. The guard rails may be placed aside or hung from the frame on hooks (not shown), while the quick release auxiliary blocks and poles, may be likewise removed or shifted to the distal end of the PS3, as necessary, thereby permitting entry into the MRI apparatus.

The embodiment illustrated in FIG. 4 illustrates a frame upper cross member 34 (which may be replaced by an alternative transfer frame which permits reversal of the cantilever frame). Note the frame lower legs 38 are provided with wheels 46 permitting easy transport of the frame. Frame to single surface interface or cantilever arms 40 are mounted on frame cantilever column 36 enabling vertical movement of the cantilever arms.

Now referring to FIG. 5, an exploded view of PS3 single surface platform, wing sections and guardrails is illustrated. The single surface platform is segmented into two sections, a backrest section or uppermost section 14 and a lower section 16. In addition backrest section wings 24 (2 shown) and a lower section wings 26 (2 shown) are illustrated. The backrest section and lower section of the platform are provided with single surface to frame interfaces or hooks 50. The single surface platform is shown as frameless. However, a frame may be associated with the platform. For example, a frame could completely encircle the perimeter of the single surface platform or only extend along both longitudinal edges of the platform.

Figure 8:
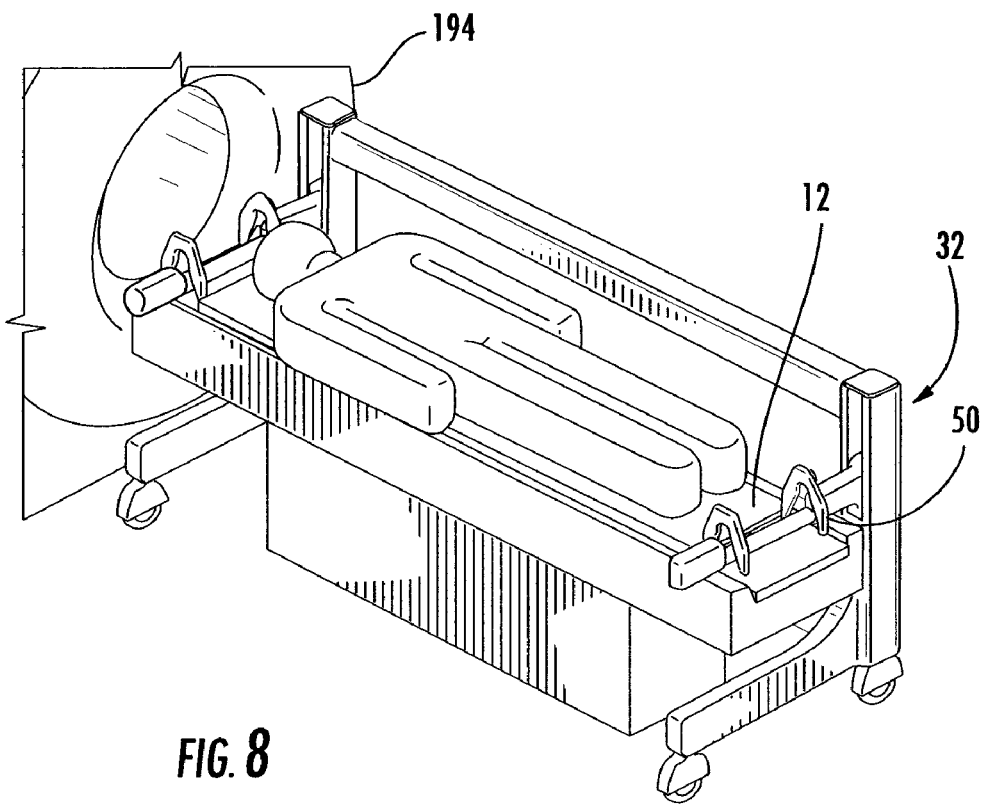
FIG. 8 is a perspective view of FIG. 7, illustrating the PS3 single surface platform and patient lowered fully onto a MRI bed and locked into self-guiding T-pins.
Figure 9:
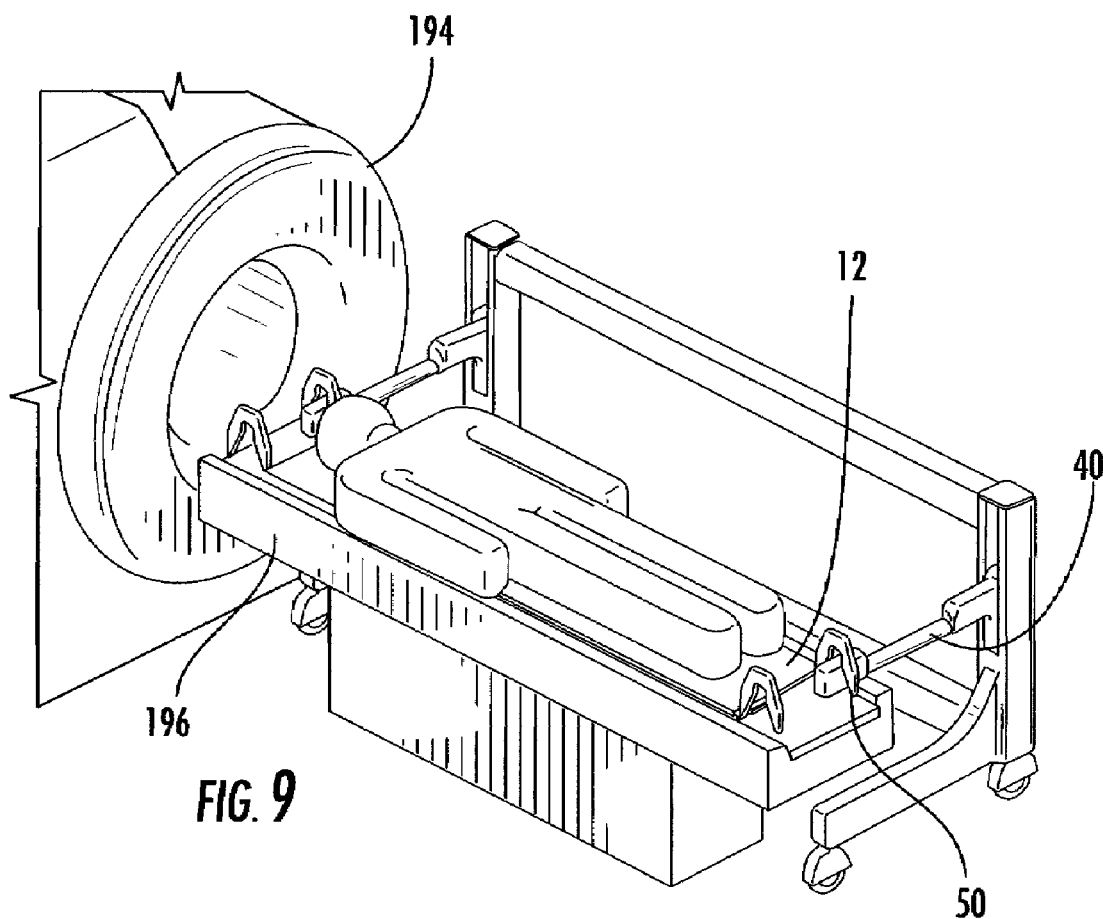
FIG. 9 is a perspective view of the system similar to FIG. 7, illustrating the PS3 cantilevered frame being removed from the PS3 single surface platform and MRI bed.

FIG. 8 shows the PS3 platform and patient lowered fully onto the MRI bed platform and locked into the self-guiding T-pins. The PS3 platform is released from the cantilever frame 32 at this stage. Note gap between the frame to single surface interface or single surface supporting member 40 and the single surface to frame interface or supporting member engagement means 50, which allows for the removal of the frame. Due to the design of the frame and hook components, the frame to single surface interface 50 enables separation from the transport frame 32 without requiring the frame to single surface interface hooks to drop below the surface of the platform 12.

Figure 10:
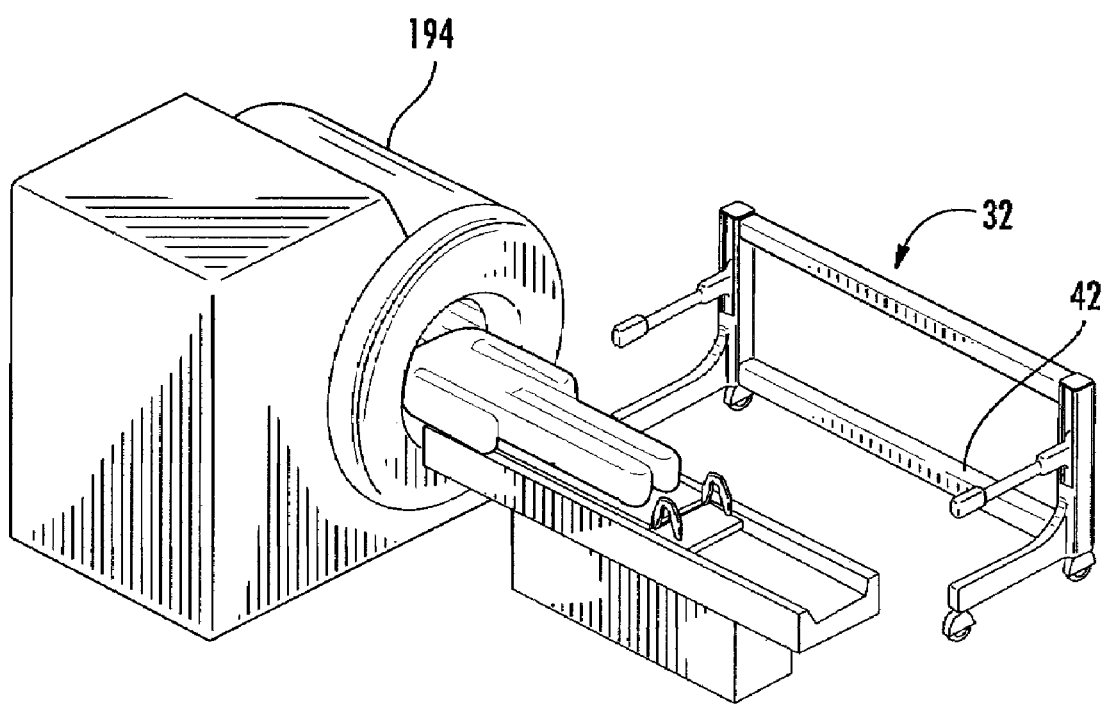
FIG. 10 is a perspective view of the PS3 single surface platform illustrating its ability to transfer a patient into a MRI device while patient remains on PS3 single surface platform.

FIG. 10 illustrates an ability to complete the MRI test by traversal of the PS3, shown in mechanical engagement with the MRI bed, into the MRI device. Note that the self lock, quick-release hooks or single surface to frame interface 50 can be removed if necessary. It is understood that to retrieve the patient for further transport/transfer, the above steps will be reversed.

It is further noted that the unique design of the single surface to frame interface 50 on the single surface platform provides a secure, self-aligning interface between the PS3 platform 12 and the frame to single surface interface 40. The single surface to frame interface also allows quick release of the single surface platform 12 from the frame 32 once the single surface platform is fully lowered onto another surface.

Figure 11:
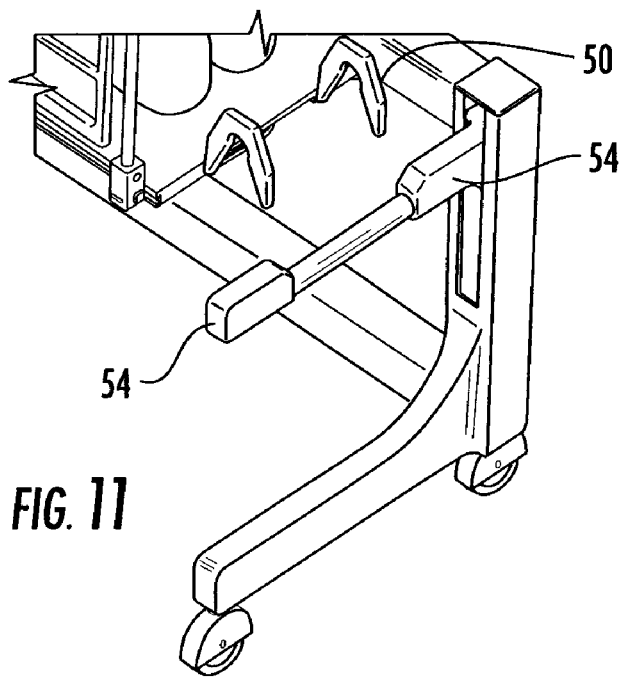
FIG. 11 is a partial view of the PS3 system illustrating one example of the PS3 single surface platform to frame interface.

FIG. 11 shows an illustrative example of a PS3 single surface to frame interface 50 using a hook style which is self aligning with the alignment and lateral location members 54 on the frame to single surface interface 40.

Figure 12:
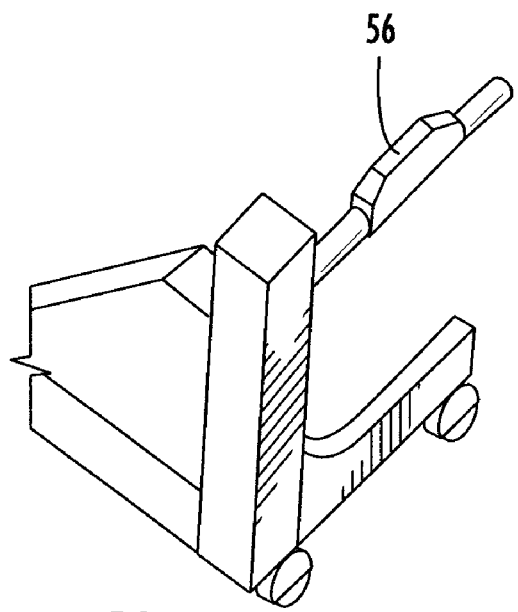
FIG. 12 is a perspective view of another embodiment of the PS3 frame to single surface interface member.

FIG. 12 shows an alternative illustrative example of a central, upraised alignment and lateral location member 56 on the frame to single surface interface.

Figure 13:
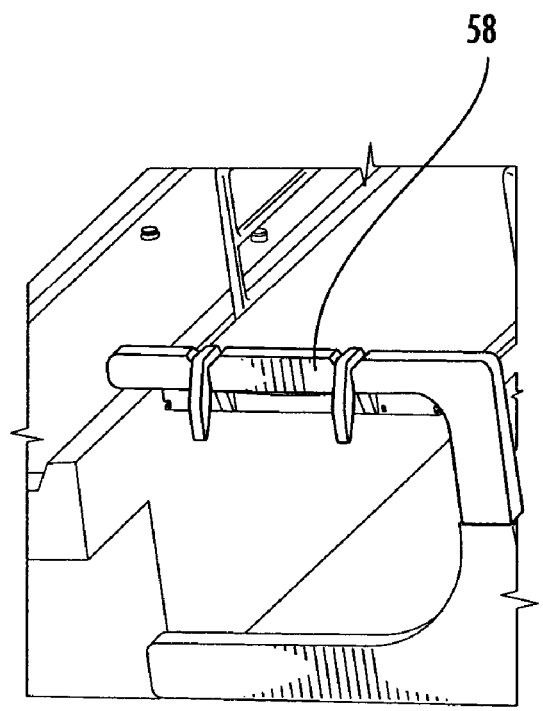
FIG. 13 is a perspective view illustrating a third embodiment of a PS3 frame to single surface interface member with redundant alignment surfaces for the single surface to frame interface members.

FIG. 13 is yet another illustrative example of a PS3 single surface to frame interface which depicts redundant transverse surfaces on the frame to single surface interface 58 for mating of the single surface to frame interface 50 with the frame to single surface 58.

Figure 14:
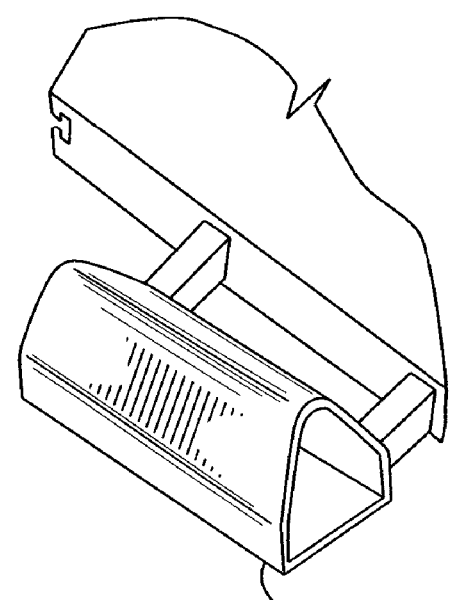
FIG. 14 is a partial view of the PS3 single surface platform provided with a "box" receiver, as an additional example of the single surface to frame interface, for insertion of the frame to single surface interface of FIG. 11.

FIG. 14 shows an alternative embodiment of the PS3 single surface to frame interface wherein a receiver or "box" 52 is designed to encircle and self-align with a frame to single surface interface as shown in FIG. 11. Alternatively, this design may be formed with an upper opening for receipt of the central upraised surface of the arm of FIG. 12, in order to make that coupling self-aligning as well.

Figure 15:
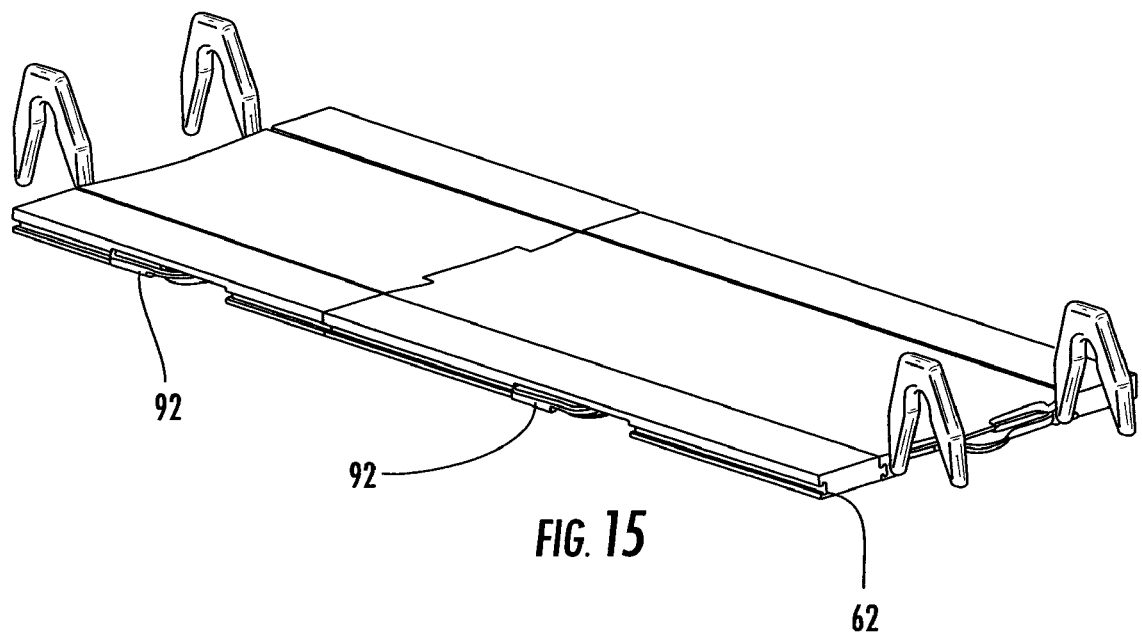
FIG. 15 is a perspective view of the PS3 single surface platform with the wings attached and a hinge for the single surface backrest section.

FIG. 15 represents a perspective view of the PS3 segmented single surface, inclusive of segmented wing assemblies, removable single surface to frame interfaces or hooks and actuation handles 92.

Figure 16:
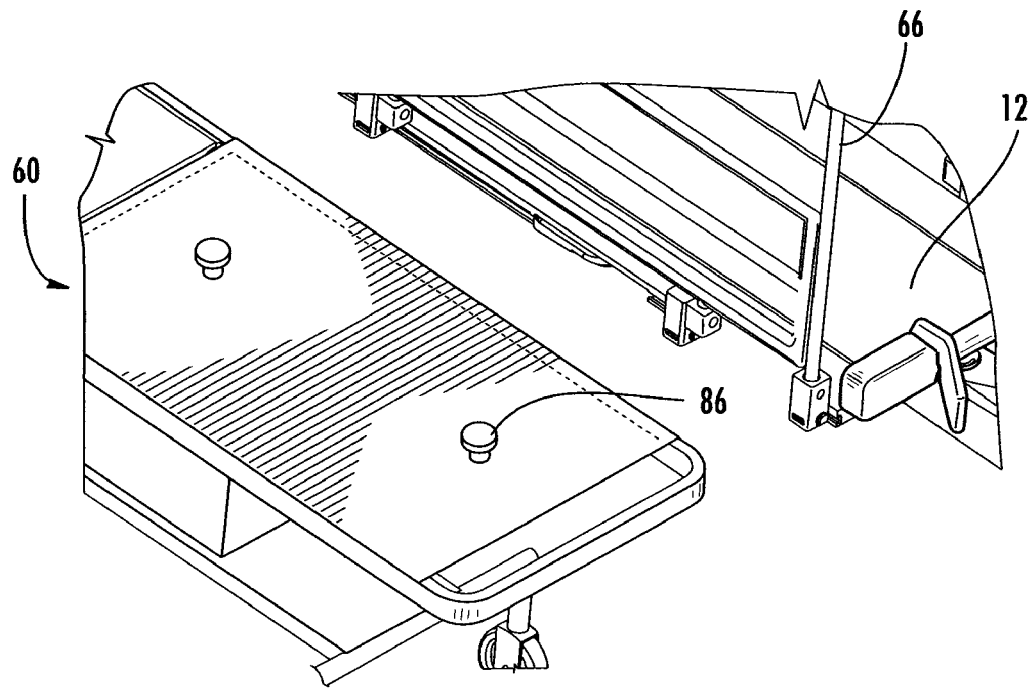
FIG. 16 illustrates the PS3 system and a gurney onto which the PS3 single surface platform is to be placed.

FIG. 16 shows an embodiment which illustrates the PS3 single surface platform 12 approaching a gurney 60. The gurney includes mating T-pins for affixing the PS3 single surface platform to the gurney, which are the only additions/modifications required to the gurney to allow a secure interface with the PS3 single surface, thereby enabling disengagement of the articulation inter-lock system 68. Engagement of the inter-lock system prevents the hinged portions of the frameless version single surface from bending with respect to each other. Thus permitting the frameless version single surface support platform to be supported only at each of the ends.

Details regarding the secure interface and articulation inter-lock follow in FIG. 18 to FIG. 27.

Figure 17:
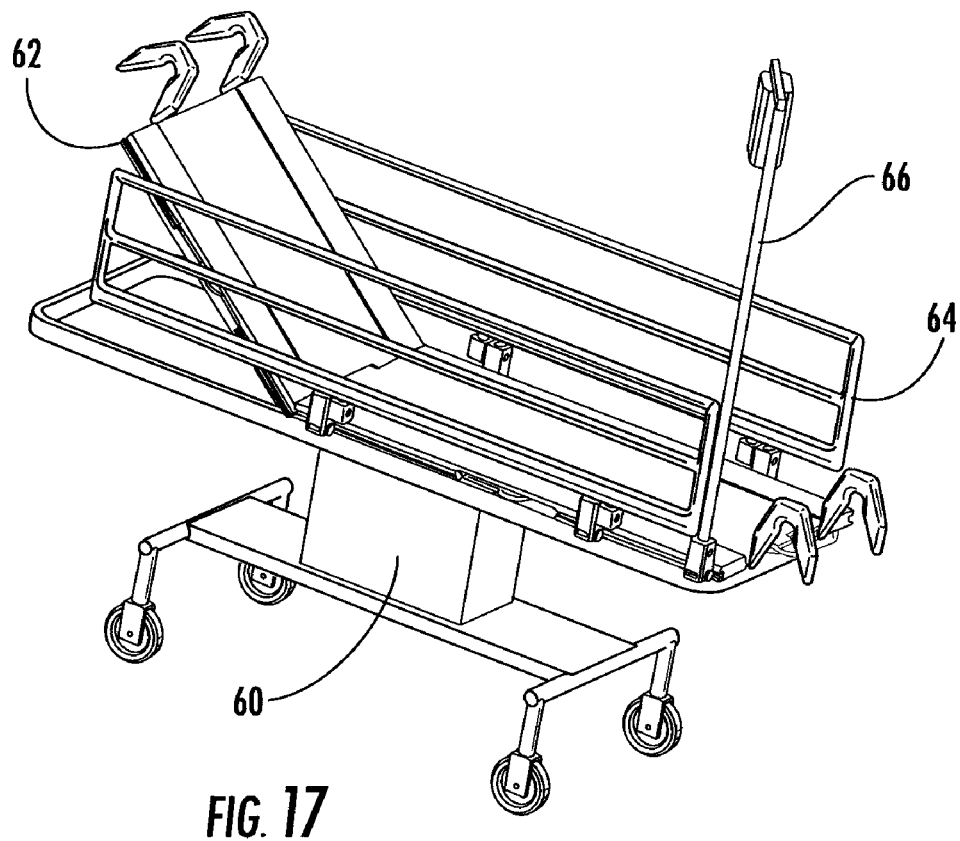
FIG. 17 is a perspective view of the PS3 single surface platform illustrating the single surface backrest section of the PS3 single surface platform tilting, after the PS3 is securely mated to the gurney.

FIG. 17 illustrates the PS3 single surface platform with the backrest portion 14 elevated, such articulation only being enabled once the PS3 single surface is securely mated to a surface like this wheeled gurney via positive engagement of the T-pins whereby the articulation inter-lock may be disengaged.

Figure 18:
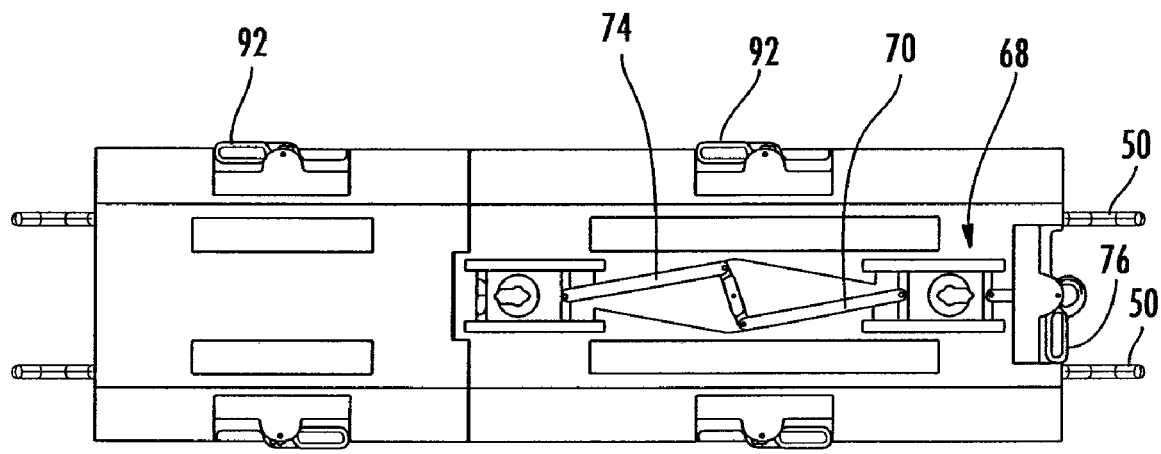
FIG. 18 is a bottom view of the PS3 single surface platform assembly of FIG. 15.

FIG. 18 is an underside view of the PS3 single surface platform having the articulation inter-lock system formed integral therewith and illustrates translation of the interlock plates via the four-bar linkage 70 which is enabled upon engagement of interlock plate release lever (not shown) by the T-pins (not shown). Note the eccentric lever 76 or "articulation handle(s)" effective to operate the articulation inter-lock system and lever 92 effective to operate the inter-lock for the wing assemblies.

Figure 19:
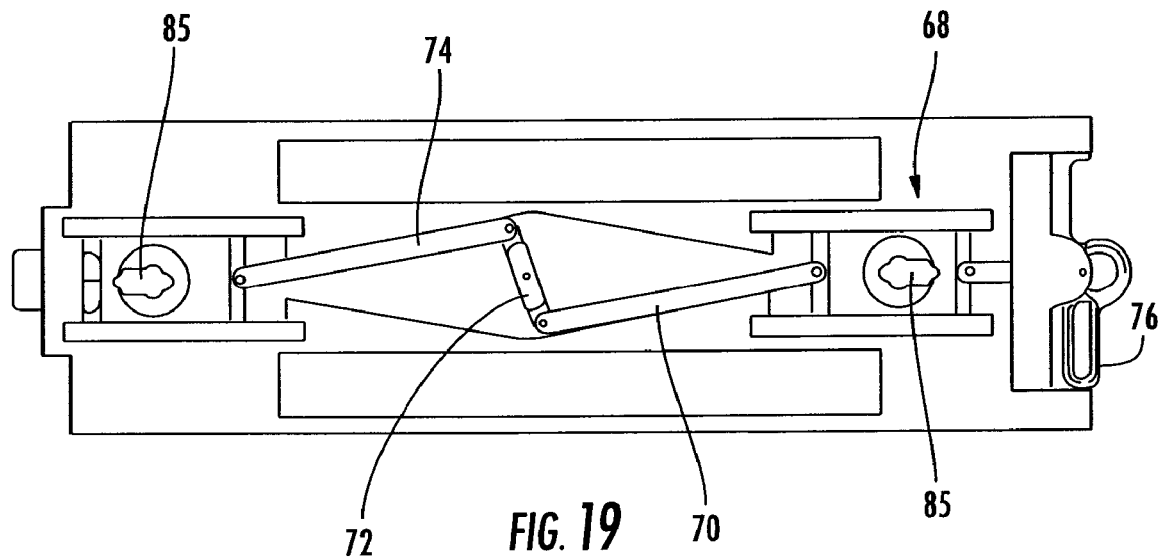
FIG. 19 is a bottom view of the PS3 single surface platform assembly without wings and without the single surface backrest section, illustrating the lock plates and 4-bar linkage, which causes the plates to move toward each other when the handle is rotated.

FIG. 19 is an underside view of the PS3 single surface platform without wings and without the backrest section. This figure shows the inter-lock plates 78 and four-bar linkage 70. Rotation of the handle 76 in a counterclockwise direction moves the right inter-lock plate 78 toward the left, which pushes bar 70 to the left. This action rotates four-bar center link 72 clockwise, which pulls four-bar link 74 to the right. This moves the left inter-lock plate to the right thereby causes the inter-lock plates to move toward each other when the eccentric lever 76 is rotated. Additionally, a backrest lock bar 88 (FIGS. 25 & 26) keeps the frameless PS3 single surface platform rigid and flat when it is suspended and/or not properly supported by a mating surface underneath such as a gurney. The T-pin inter-lock keyhole 85 is illustrated wherein an internal taper surrounding the keyhole slot 85 provides a self-aligning feature.

Figure 20:
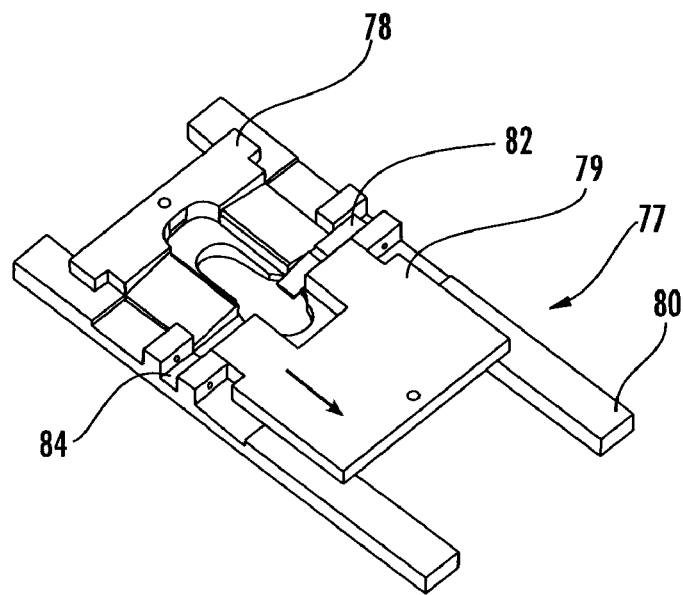
FIG. 20 is a top perspective view of the PS3 lock plate with keyhole and interlock.

FIG. 20 is a detailed isometric view of the inter-lock plate assembly 78 showing the inter-lock plate rails 80 which are affixed to the PS3 single surface platform. The inter-lock plate is in its open position, and the spring-biased inter-lock lever 82 is shown in its lower position, in inter-lock lever recess 84, which prevents movement of inter-lock plate 78. Inter-lock plate is connected to four-bar link 70 which moves another inter-lock plate 79. Inter-lock lever 82 is raised upon insertion of the T-pin 86 or equivalent mating means, thereby enabling translation of the inter-lock plate about the mating device to retract the single surface locking pins (not shown) while simultaneously affixing the single surface platform to the underlying support gurney, MRI/scanner bed, articulating transfer frame, or the like.

Figure 21:
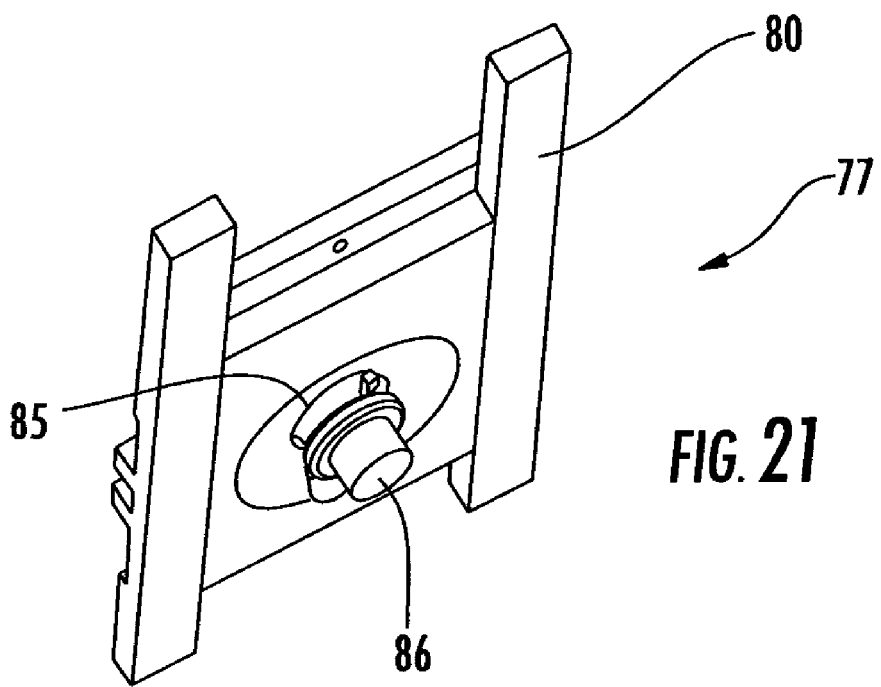
FIG. 21 is a bottom perspective view of the PS3 lock plate and a T-pin.

FIG. 21 is an isometric view of the underside of the PS3 inter-lock plate module 77, showing alignment of the T-pin 86 with the keyhole 85, by virtue of the tapered mating area by which a self-aligning utility is achieved, and also showing the small to large cross-sectional are of each which allows secure mating in all directions. Although the T-pin or inter-lock module securement element 86 is illustrated as being round, triangular, hexagonal, or the like shapes may be used effectively, so long as they generally embody a large cross-section versus small cross section relationship that facilitates their mating together.

Figure 22:
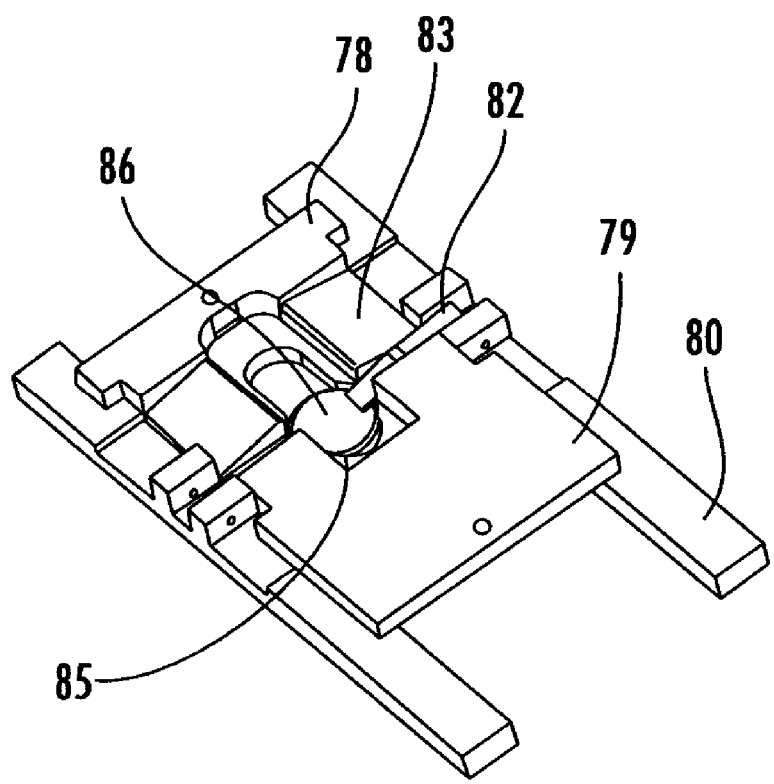
FIG. 22 is a top perspective view of the PS3 lock plate engaging a T-pin.

FIG. 22 illustrates the PS3 single surface platform inter-lock plate module 77 with the T-pin 86 engaged in large end of keyhole 85. Note that the inter-lock lever 82 is still below the top surface of the inter-lock ramp 83. The inter-lock plate 78 still cannot translate motion to inter-lock plate 79 at this stage.

Figure 23:
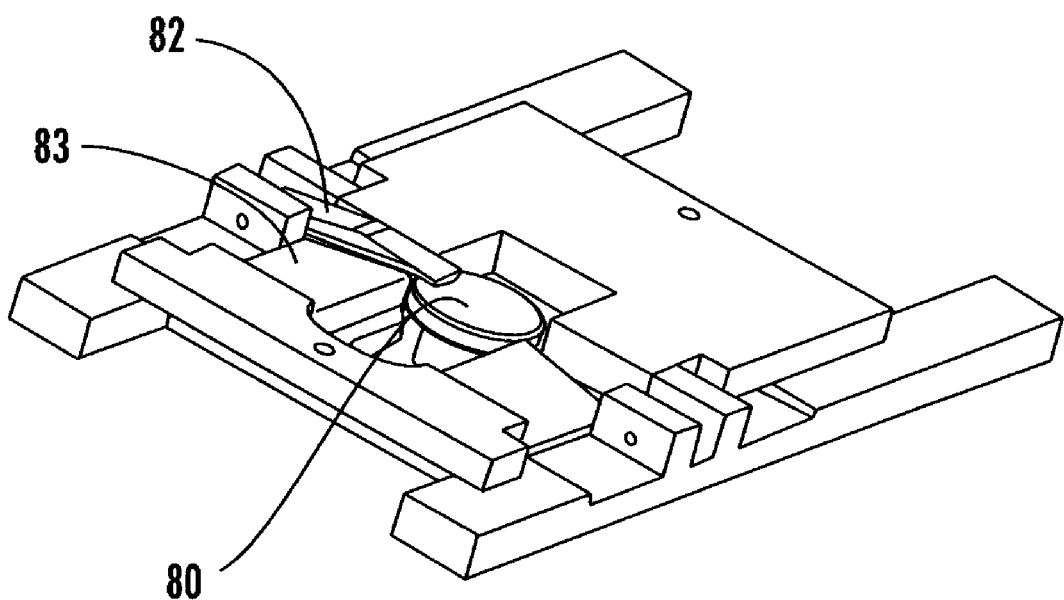
FIG. 23 is a top perspective view of the PS3 lock plate illustrating positioning of the PS3 interlock lever above the interlock ramp when the bottom of the PS3 single surface platform is resting on a mating surface.

FIG. 23 illustrates further engagement of the T-pin with the inter-lock plate module 77 whereby the PS3 inter-lock lever 82 is now above the inter-lock ramp 83. At this stage, since the bottom of the PS3 single surface platform is resting on a mating surface such as a gurnie, the inter-lock lock plate can translate motion to the inter-lock plate 79 (in the direction of the arrow shown in FIG. 20) as long as the other inter-lock plate block 77 is disengaged in a similar manner.

Figure 24:
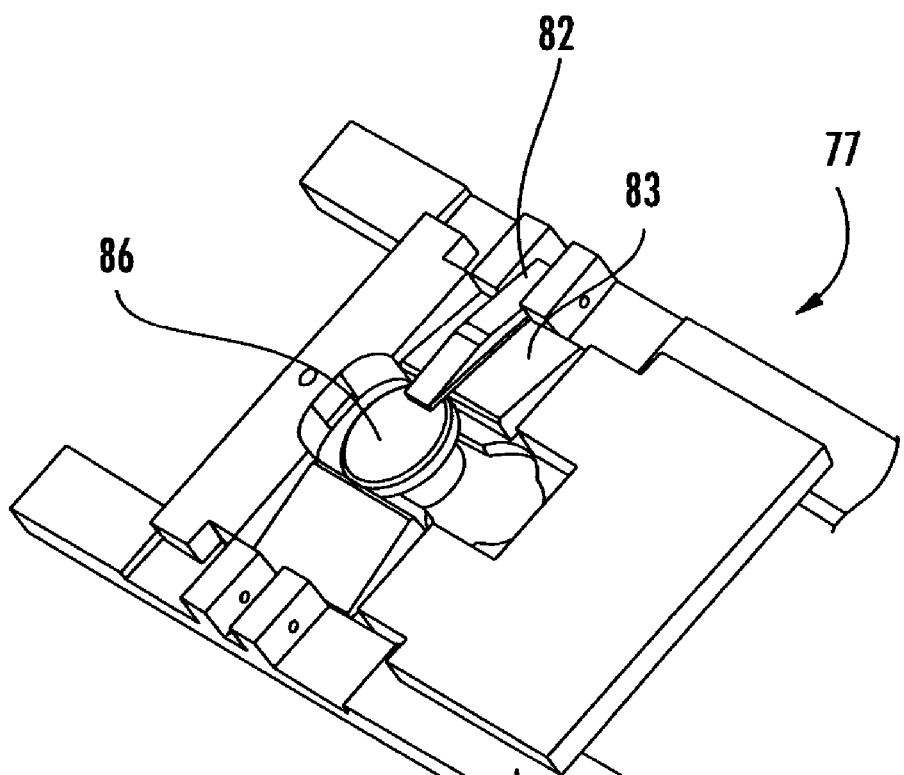
FIG. 24 is a top perspective view of the PS3 lock plate in its final locked position.

FIG. 24 shows the PS3 inter-lock block 77 in its final locked position as its opposing inter-lock plate is as well, whereby the PS3 Single surface platform is secure to its mating surface in all directions. Also, the Backrest lock bar 88 is retracted as shown in FIG. 27.

Figure 25:
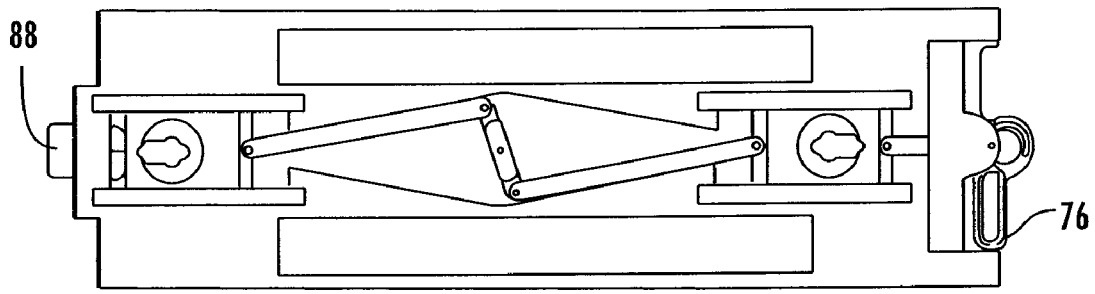
FIG. 25 is a bottom view similar to FIG. 19, illustrates the PS3 single surface without wings and without the single surface backrest section, illustrating the lock plates and 4-Bar linkage.
Figure 26:
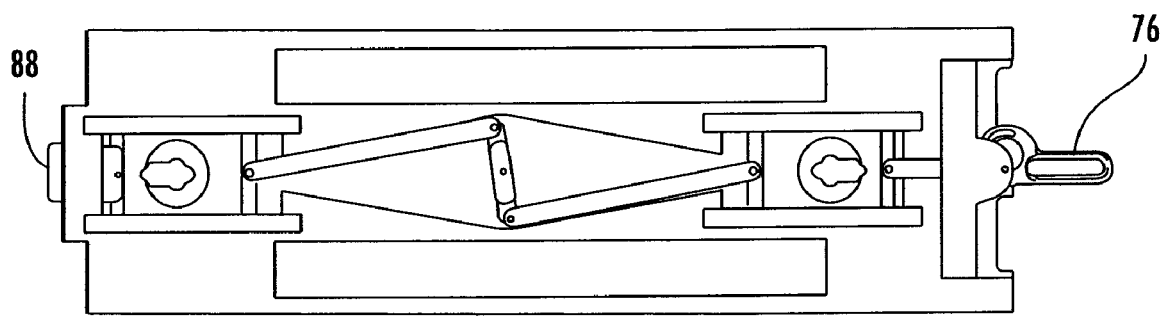
FIG. 26 is the PS3 single surface platform of FIG. 25 illustrating the PS3 lock/unlock handle rotated 90 degrees counter clockwise causing translation of the two lock modules toward each other (due to the 4-Bar Linkage) to secure the PS3 single surface to the mating surface and retracting the single surface backrest section lock bar.
Figure 27:
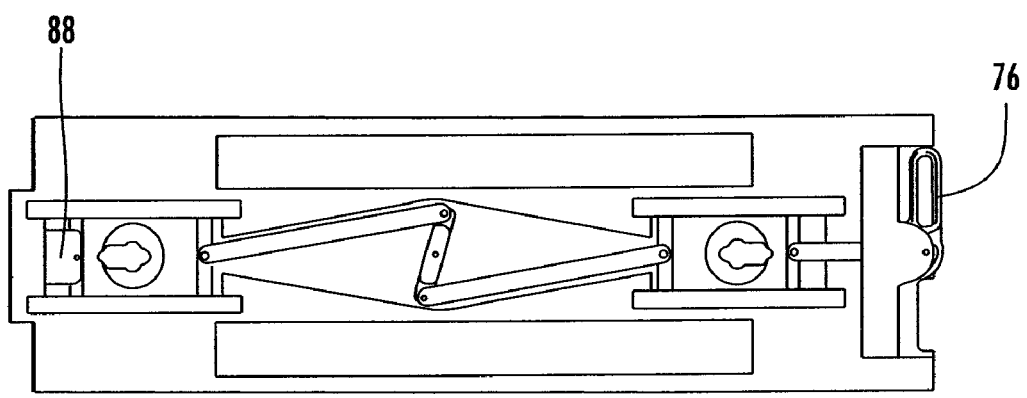
FIG. 27 is the PS3 single surface platform of FIG. 25 with the PS3 lock/unlock handle rotated 180 degrees counter clockwise causing translation of the two lock modules toward each other to their final locked location, wherein the single surface backrest section lock bar is completely withdrawn.

With reference now to FIGS. 25-27, as FIG. 25 is equivalent to FIG. 19, above which shows an underside view of the PS3 single surface platform without wings and without the backrest section. These figures shows the inter-lock plates and four-bar linkage, which causes the plates to move toward each other when the eccentric lever is rotated (note that the eccentric lever could be flipped, the lock plates rotated 180 degrees and a flexure in the lock bar added like the knee gatch lock bar in which the lock plates would move away from each other). Additionally, the backrest tilt lock bar, which keeps the frameless PS3 single surface platform "Rigid" and flat when it is suspended and/or not properly supported by a mating surface underneath like, e.g. a stretcher. The docking/mating means (T-pin) interlock is illustrated wherein an internal taper surrounding the keyhole slot provides a self-aligning feature.

FIG. 26 shows the PS3 eccentric articulation handle 76 (Lock/Unlock Handle) rotated 90 degrees counter clockwise causing translation of the two inter-lock blocks 77 toward each other (due to the four-bar linkage) to secure the PS3 single surface lower section to the mating surface and retraction of the backrest lock bar 88 as shown. (T-pins are not shown for clarity, which would be required in position as shown above to release the Interlock and allow translation.)

FIG. 27 further illustrates the PS3 eccentric articulation handle 76 rotated 180 degrees counter clockwise causing translation of the two inter-lock blocks 77 toward each other to their final locked location and the backrest lock bar 88 completely withdrawn. (T-Pins not shown for clarity, which would be required in position as shown above to release the Interlock and allow translation of the Lock Plates.)

Figure 28:
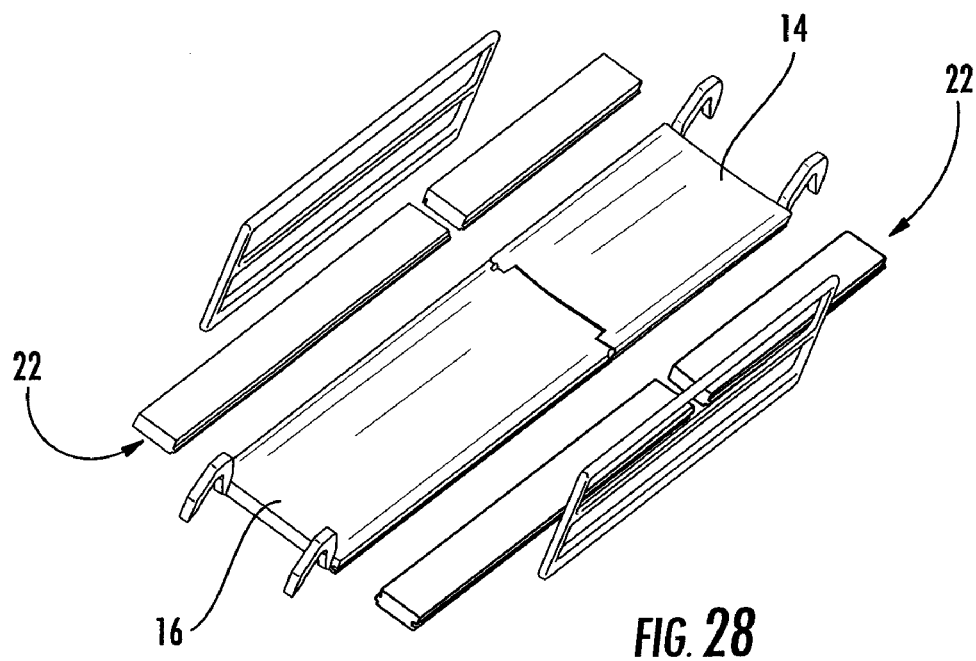
FIG. 28 is an exploded view of the PS3 single surface with incline wings and main wings separated from the single surface.

FIG. 28 illustrates the PS3 single surface platform provided with a backrest portion 14, a lower portion 16 and a wing system 22.

Figure 29A:
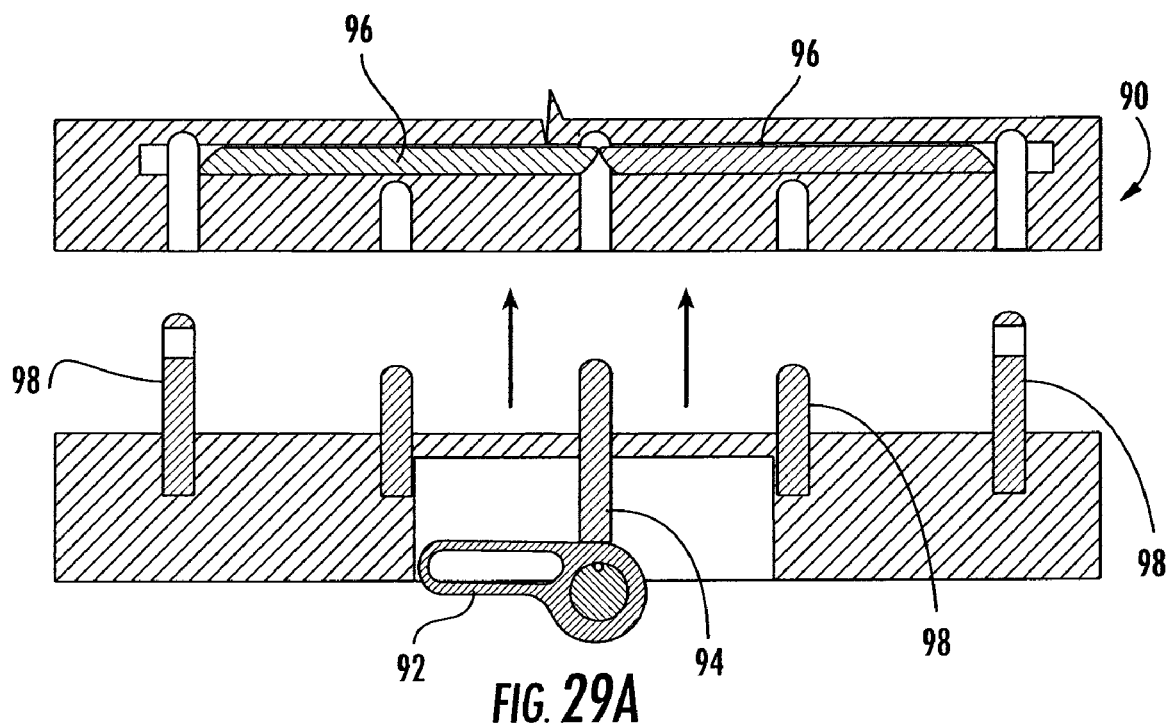
FIG. 29A illustrates an alternative PS3 lock for the wings, which is of a quick lock and release design, but is not self-locking into the side of the single surface.

FIG. 29A is illustrative of one embodiment of a PS3 wing lock assembly 90, illustrating a quick lock and release actuation handle 92. The actuation handle 92 is eccentrically mounted such that counterclockwise rotation moves lock actuation pin 94 in an upward direction. The actuation pin 94 moves lateral lock bars 96 in an outwardly horizontal direction engaging wing lock pins 98 (the inner pins are no longer lock pins, but alignment and vertical load support pins). The lateral lock bars and the lock pins have tapered profiles (not shown) to assist their engagement. The engagement of the lock pins 98 by the lateral lock bars secures the wings to the single surface platform. The lateral lock bars are spring loaded to return them to their unlocked position when the lock actuation pin 94 disengaged them and retracts.

Figure 29B:
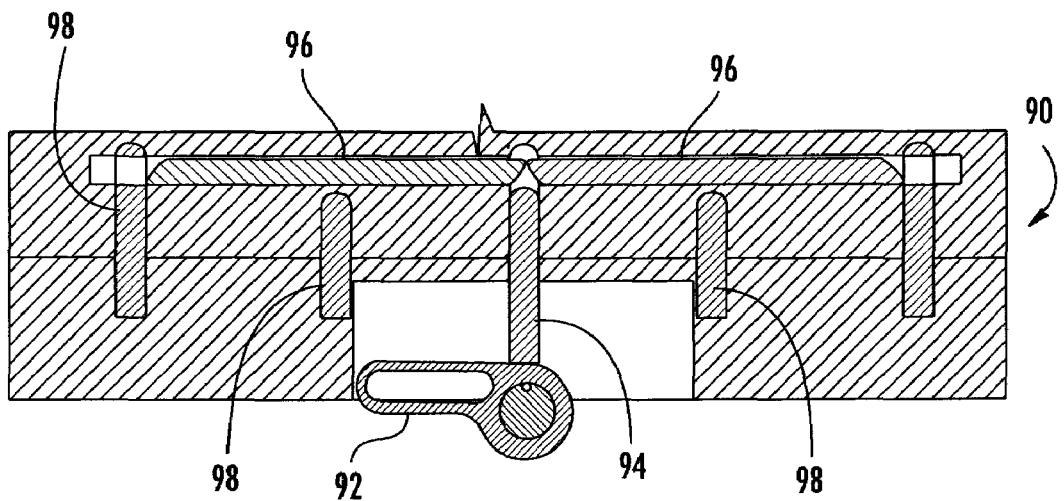
FIG. 29B illustrates the alternative PS3 lock, in its unlocked position, with the wing abutted to the single surface.

FIG. 29B is illustrative of the wing abutting the single surface prior to the lock being engaged.

Figure 30:
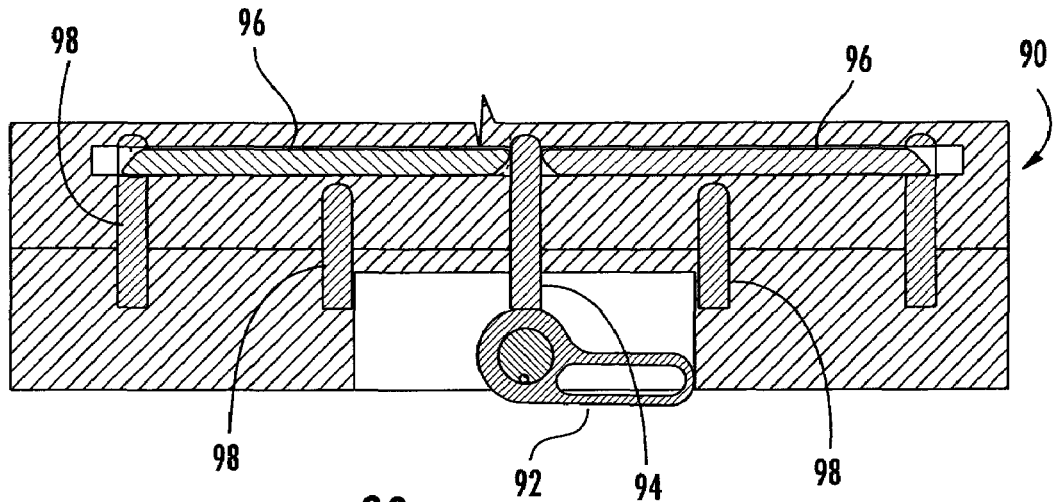
FIG. 30 illustrates the alternative PS3 lock, in its locked position, securing a wing to the single surface.

FIG. 30 illustrates engagement of the PS3 lock. Actuation handle 92 has been rotated clockwise to its locked position. The eccentricity of the actuation handle moves the lock actuation pin 94 upwardly which actuates a set of lateral lock bars 96. The short wing lock pins provide additional support of the wing with respect to the single support platform thereby locking the wings securely onto the single support surface platform.

Figure 31:
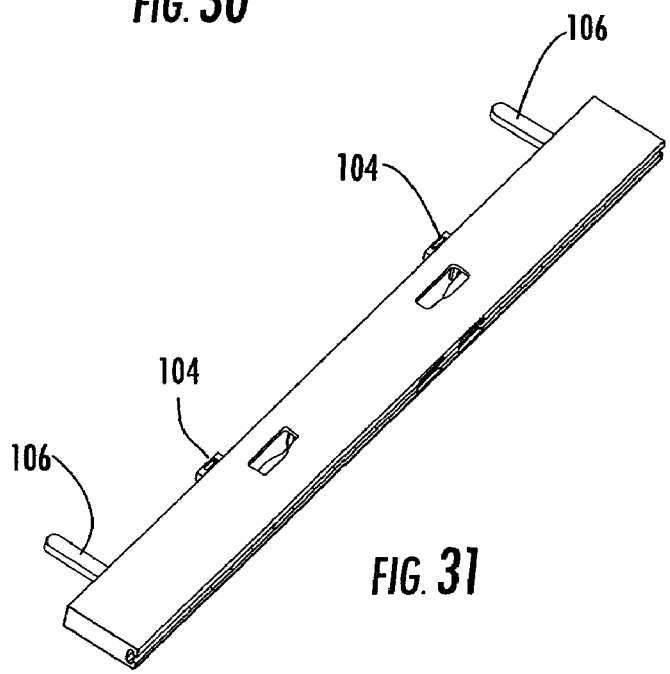
FIG. 31 is a perspective view of a preferred embodiment of a PS3 wing which is self-locking onto the main single surface platform.

FIG. 31 shows an embodiment of the PS3 wing which is self-locking into the PS3 single surface platform. The figure shows hand access cutouts for release levers to retract self-locking catches 104. Alignment pins 105 provide vertical load support and alignment to the single surface. The number of alignment pins 105 may vary as required, for example one or more may be added in the middle of the wing.

Figure 32:
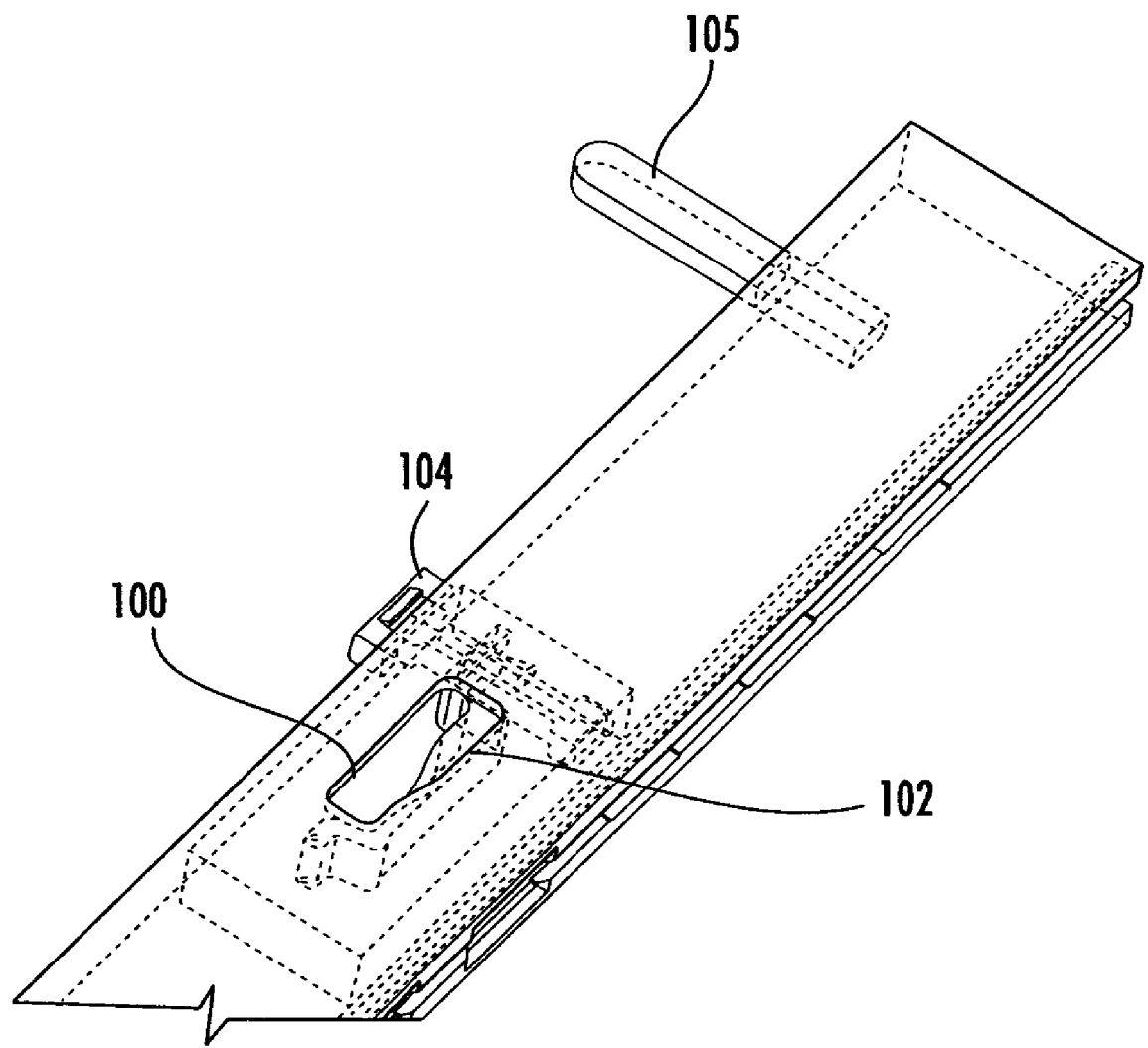
FIG. 32 is a partial perspective view of the PS3 wing illustrating the self-locking mechanism.

FIG. 32 illustrates a transparent view of a PS3 wing including hand access apertures 100 for release levers 102 to retract self-locking catches 104. Alignment pins 105 provide vertical load support and alignment with the single surface platform 12. A detailed depiction of the two-stage release lever and self-locking catch mechanism and the T-Slot for mounting auxiliaries is set forth below.

Figure 33:
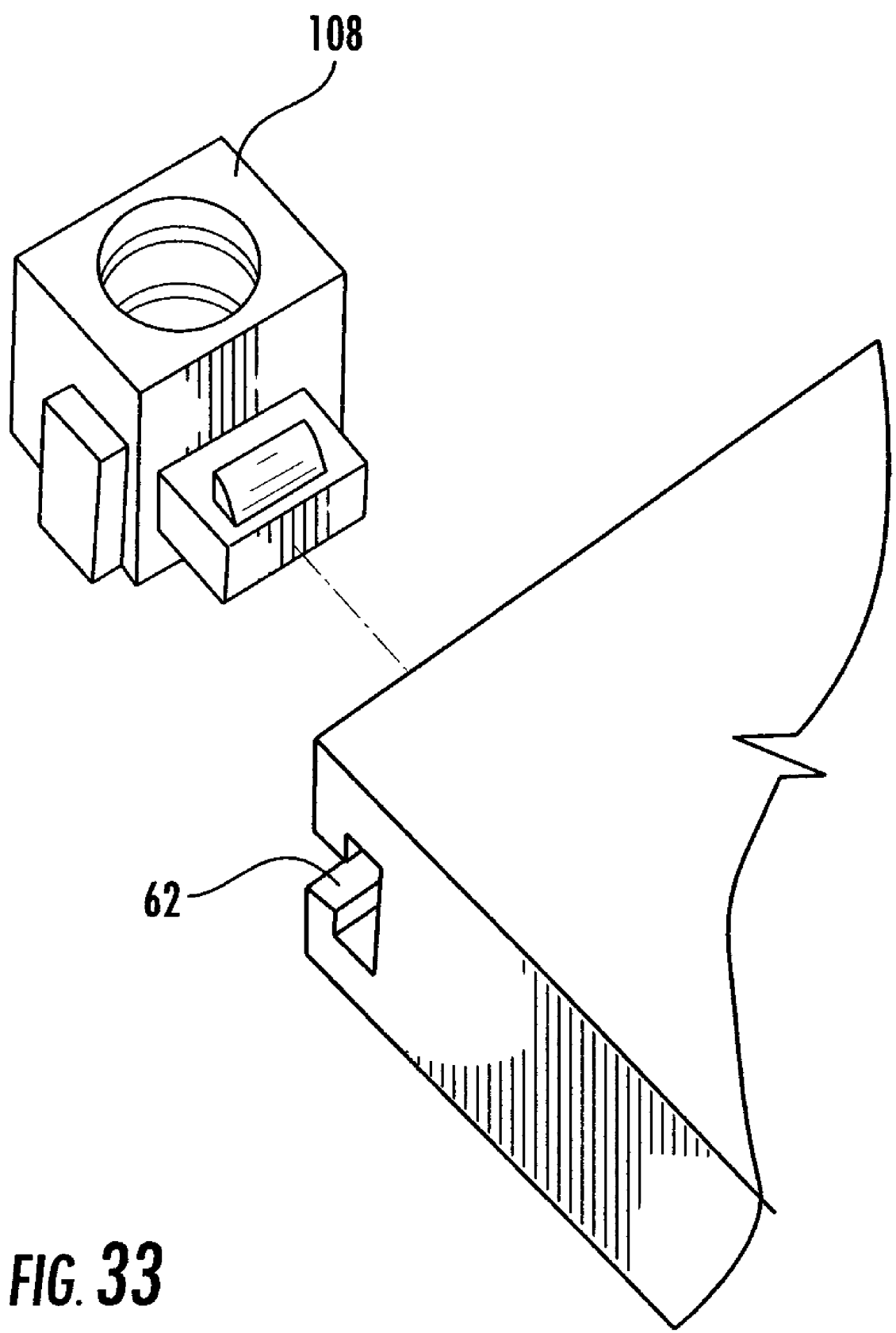
FIG. 33 is a perspective view of a PS3 push button modular auxiliary block, which self-locks onto the single surface platform or wing.

FIG. 33 illustrates a modular auxiliary block 108 having a push-button release mechanism coupled to a self-lock catch, having a pair of locking tabs which are spring biased to a locked position, but can be deflected to enable insertion into the T-slot 62 of the PS3 single surface platform or wing to enable self-locking therewith. It is noted that a passive part could also be utilized for appending to the T-slot, for example a T-pin (analogous to the T-nuts used in the machining industry for fixturing/clamping items to a T-slot surface) having a threaded nut which could be tightened to form a secure connection, or tightening of the tension lock lever style cam.

Figure 34:
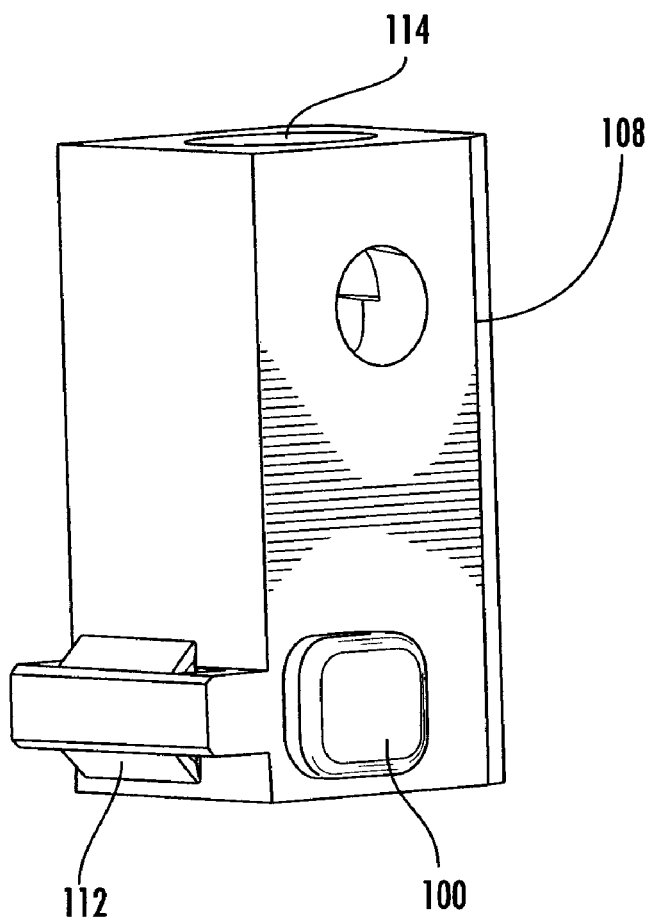
FIG. 34 is a perspective view of another embodiment of the push button modular auxiliary block illustrated in FIG. 33.
Figure 35:
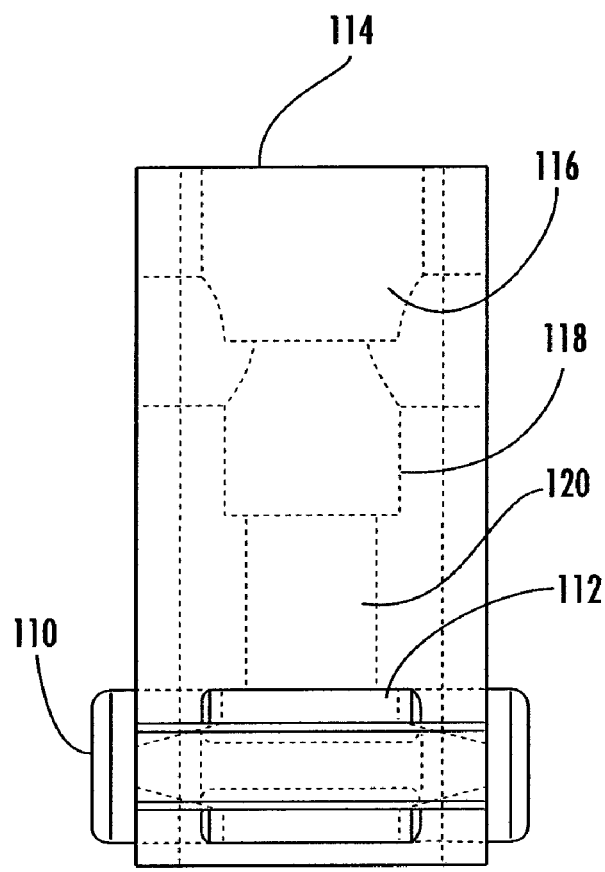
FIG. 35 is an end view of the push button modular auxiliary block illustrating the push button mechanism for closing and releasing the catch mechanism of the auxiliary block.

FIGS. 34 and 35 illustrate one embodiment of an auxiliary block design showing an external isometric view (FIG. 34) and transparent orthogonal view (FIG. 35) respectively. FIG. 34 illustrates shows push buttons 110 which interact with an internal spring biasing means (not shown) having tapered surfaces which act upon the catch tips 112 to close and release the catch when the push buttons are pressed inward. An auxiliary pole is inserted into the auxiliary block 108 through aperture 114. The auxiliary pole is then supported adjacent the single surface platform. FIG. 35 illustrates stepped holes 116, 118 and 120 which are designed to accept various auxiliary pole diameters and sizes.

Figure 36:
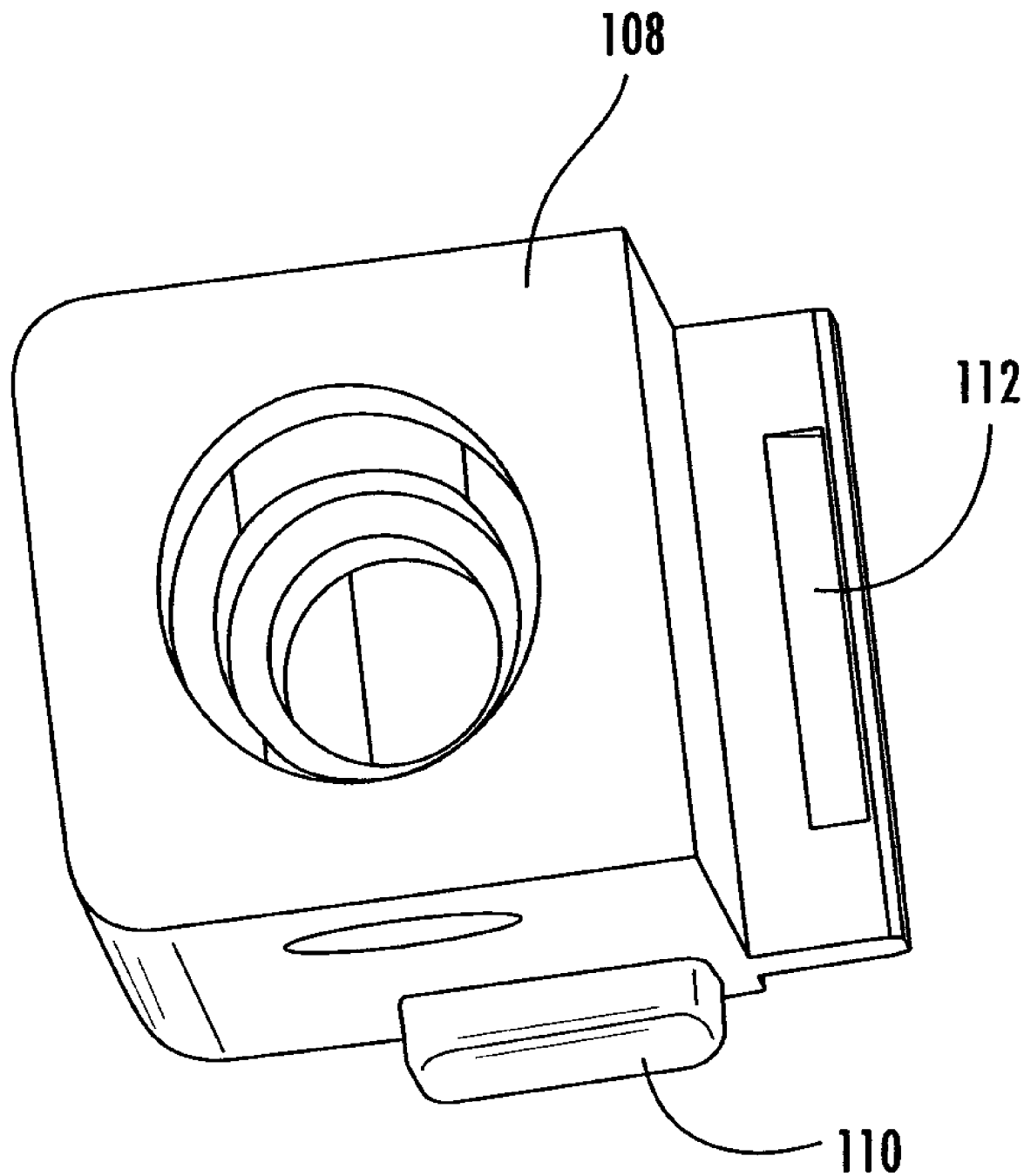
FIG. 36 is a top perspective view of the PS3 push button modular auxiliary block of FIG. 34, illustrating stepped holes to accommodate multiple pole diameters.
Figure 37B:
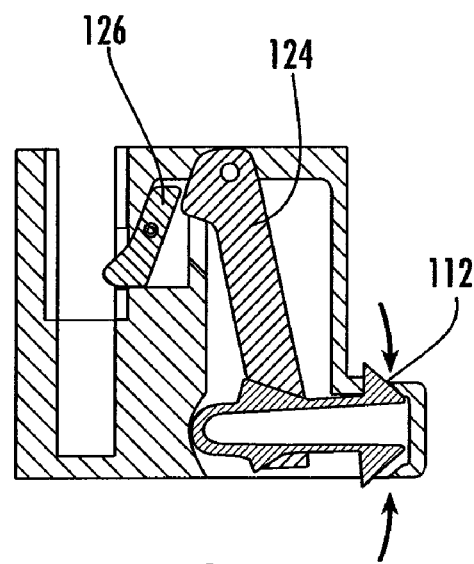
FIG. 37B is a cross sectional view of the auxiliary block of FIG. 37A, illustrating the internal design of the single lever, dual purpose T-slot and pole locking mechanism.
Figure 37A:
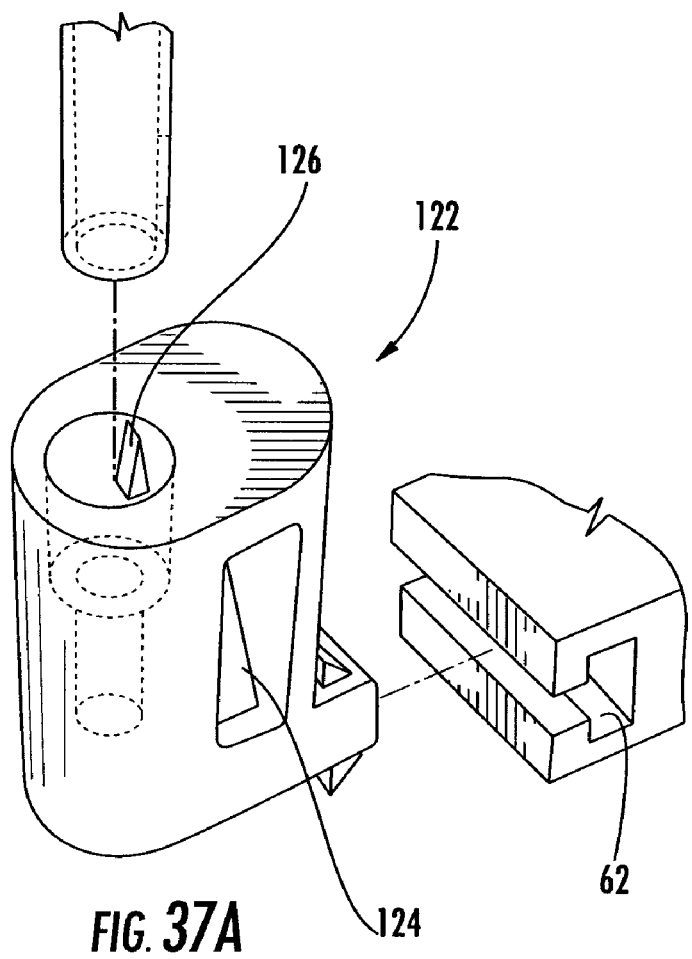
FIG. 37A is a perspective view of another embodiment of the auxiliary block illustrating a self-locking modular auxiliary block and its relationship with the PS3 main single surface platform or wing T-slot.

FIG. 36 is an perspective view of the auxiliary block of FIG. 35 which illustrates the inclusion of stepped holes to accommodate multiple pole diameters FIG. 37A is a perspective view of an alternative embodiment of the auxiliary block illustrating a self-locking modular auxiliary block 122. The auxiliary block is adapted to engage a T-slot 62 on the side of a wing or single surface platform. Release lever 124 activates both catch tips 112 and auxiliary pole lock 126 as further illustrated in FIG. 37B.

FIG. 37B is a cross sectional view of the auxiliary block of FIG. 37A, illustrating the internal design of the single lever, dual purpose release lever 124 and self-locking auxiliary pole lock 126. The release lever 124 may be moved to a first position, to the left in FIG. 48, which permits auxiliary pole lock 126 to disengage and auxiliary pole and provide for removal of the auxiliary pole. Subsequently the release lever 124 is moved to a second position which disengages the self-locking catch tips 112 from the T-slot 62 of the PS3 single surface platform or wing.

Figure 38:
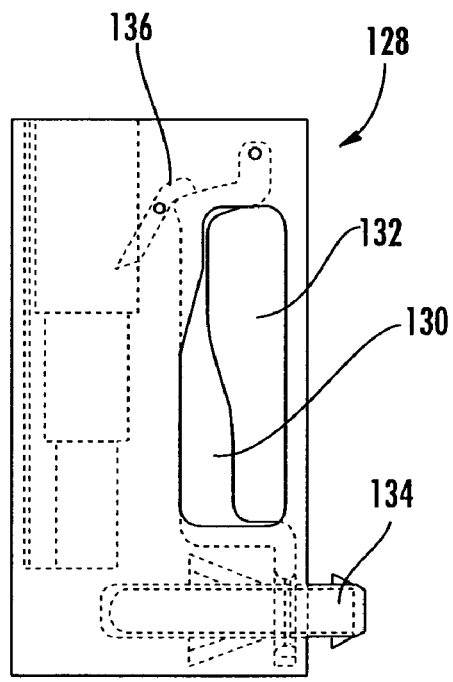
FIG. 38 is a side view of the PS3 auxiliary block of FIG. 37 A showing the release lever, and the self-locking catch, for mating between the auxiliary block and PS3 wing or main single surface platform, the auxiliary pole spring loaded lock and the stepped hole features for different sized auxiliaries.

FIG. 38 is a view of a preferred embodiment of PS3 auxiliary block 128 showing a release lever 130. A self-locking catch 134 is engagable with the PS3 T-Slot design in the wing or PS3 single surface for mating the auxiliary block 128 and PS3 wing or PS3 single surface. The front surface of the auxiliary block nose 134 is tapered to permit self alignment with a mating surface such as a T-slot. The release lever 130 also operates a auxiliary pole lock 136 which secures and auxiliary pole to the auxiliary block.

Figure 39:
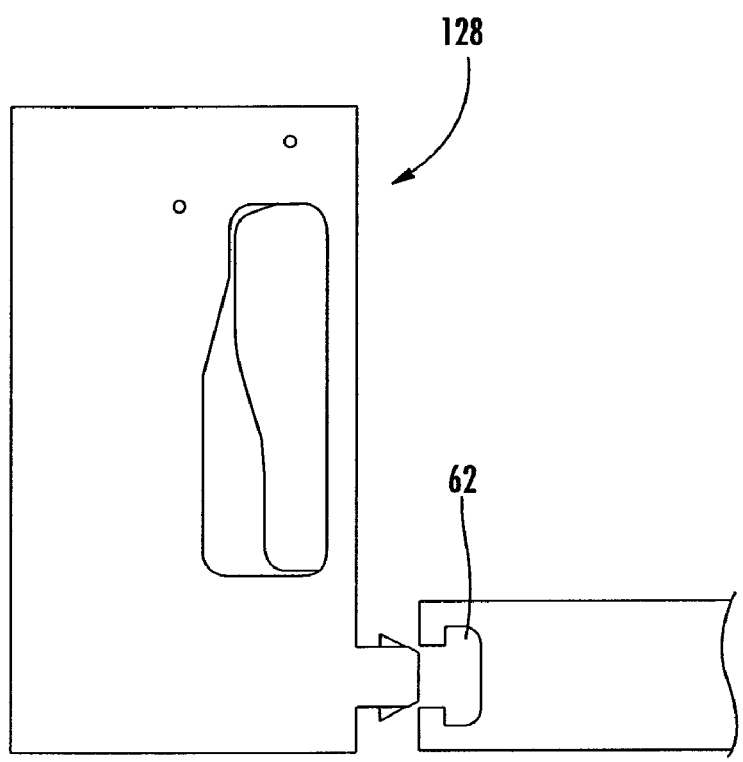
FIG. 39 illustrates the auxiliary block in position to engage the T-Slot in the PS3 main single surface platform or wing.

FIG. 39 illustrates the auxiliary block 128 of FIG. 38 in position to engage the T-Slot 62 in the PS3 single surface platform or wing.

Figure 40:
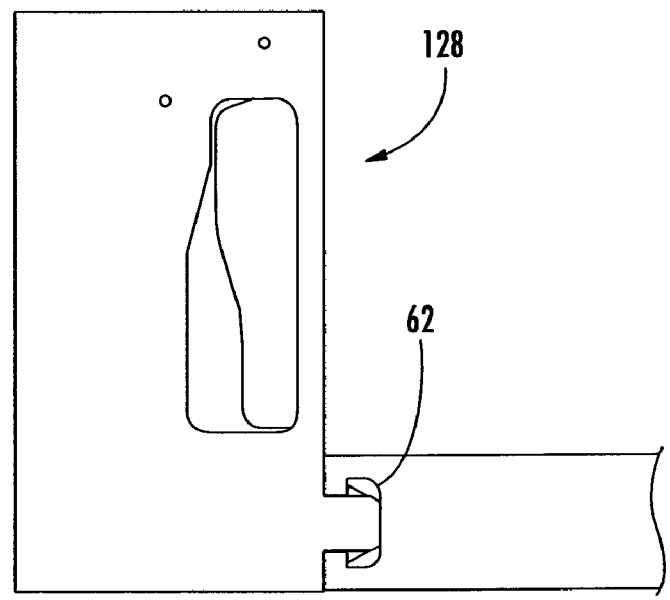
FIG. 40 illustrates the auxiliary block locked into the T-Slot in the PS3 main single surface platform or wing.

FIG. 40 illustrates the auxiliary block 128 of FIG. 38 locked into the T-Slot 62 in the PS3 single surface platform or wing. The tapered self-locking catches 112 are biased in the outward "locked" position but self-retract upon engagement with the T-slot (due to the tapers) and then "spring" back into locked position once fully engaged into the T-slot as depicted in this figure.

Figure 41:
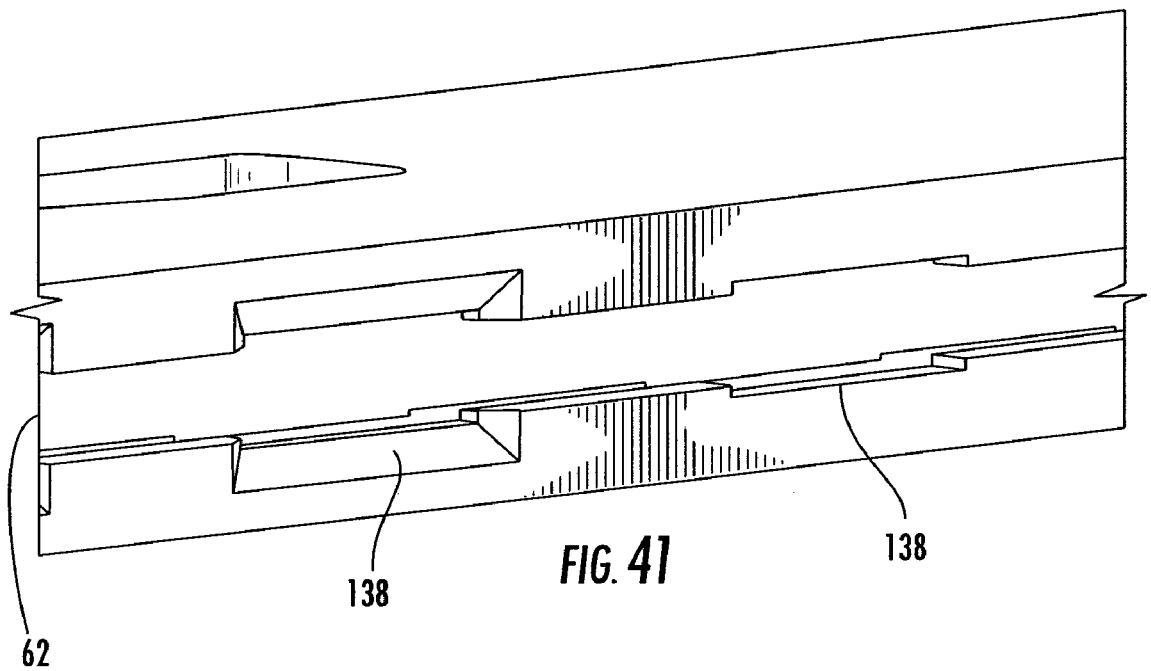
FIG. 41 illustrates a modified T-Slot in the PS3 single surface platform or wing, which includes cutouts with vertical surfaces to securely locate the auxiliary blocks along the length of the slot.

FIG. 41 illustrates a modified T-slot 62 in the PS3 single surface or wing, which includes cutouts 138 with vertical surfaces to securely locate the auxiliary blocks laterally or along the length of the slot, and further depicts tapers for self-alignment laterally and vertically.

Figure 42:
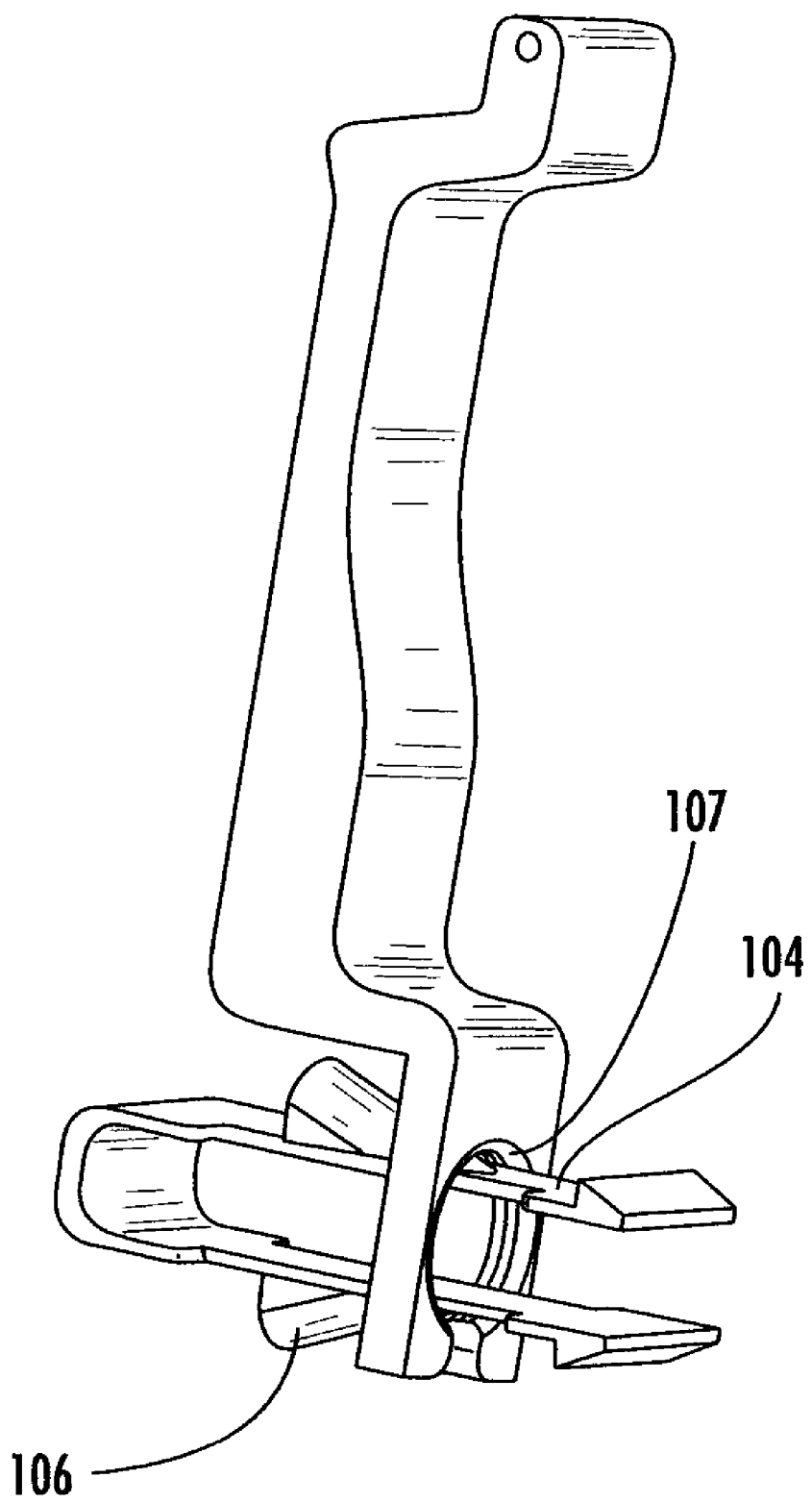
FIG. 42 shows the PS3 auxiliary block release lever wherein the release lever translates and engages a conical ramp feature on the self-locking catch for self-lock into PS3 main single surface platform or wings, The catch is formed as a spring or living hinge.

FIG. 42 illustrates the PS3 auxiliary block release lever which can rotate to engage a conical ramp 106 on the self-locking catch 104 for self-lock into PS3 single surface or wings. The aperture 107 in the release handle engages the conical ramp thereby causing the self-locking catch ends to move toward each other and release from the T-Slot on the edge of a single surface or wing. The conical ramp feature 106 on the self-locking catch 104 allows any orientation of the self-locking catch along its horizontal axis, as illustrated further in FIG. 43. The self-locking catch is formed as a spring or living hinge.

Figure 43:
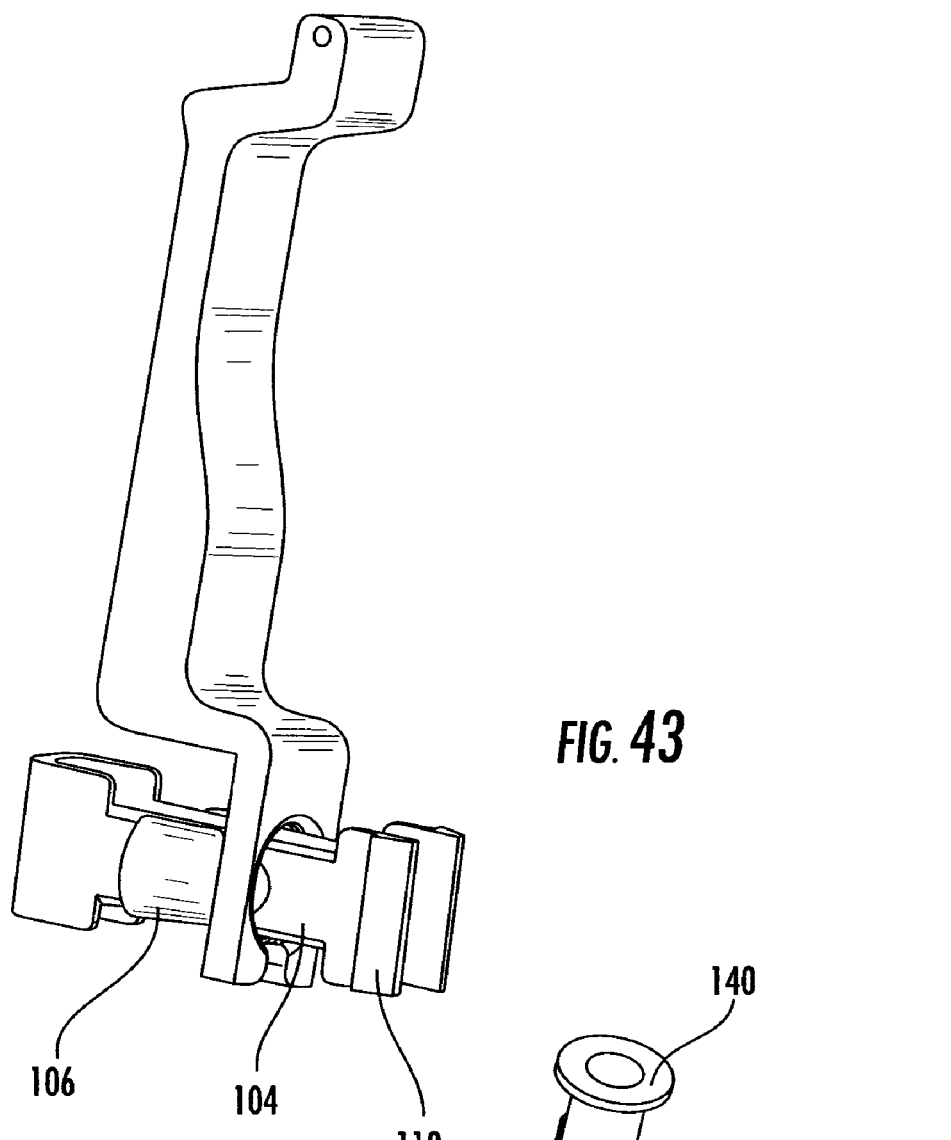
FIG. 43 illustrates another embodiment of the PS3 auxiliary block release lever and auxiliary catch wherein the catch is rotated 90 degrees from the position shown in FIG. 42.

FIG. 43 additionally illustrates the functioning of the PS3 auxiliary block release lever and auxiliary catch. Note the self-locking catch 104 is rotated 90 degrees from the prior figure. This orientation is the one used for the single surface wing self-locking catch mechanism. This orientation could also be used fro a "horizontal" version of the auxiliary block, for example.

Figure 44:
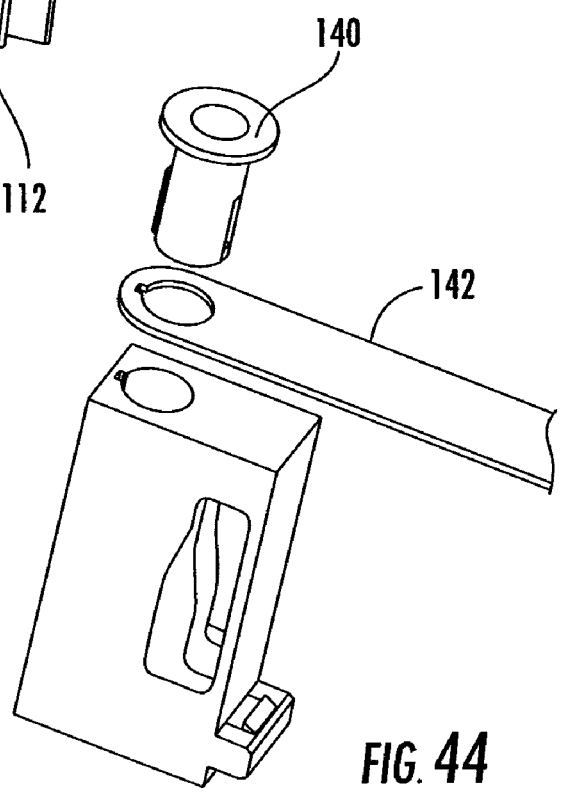
FIG. 44 is a perspective view of the PS3 auxiliary block illustrating a slot in the top to mate with the spline feature of an auxiliary lock ring to insure they mate properly. It also shows a patient safety strap attached to the auxiliary block.

FIG. 44 shows a PS3 auxiliary lock ring 140 with a spline on the side to mate with the auxiliary block 128 and insure they go together properly for the self-locking auxiliary pole lock 136. It also shows a patient safety strap 142 in position to mate to the auxiliary block.

Figure 45:
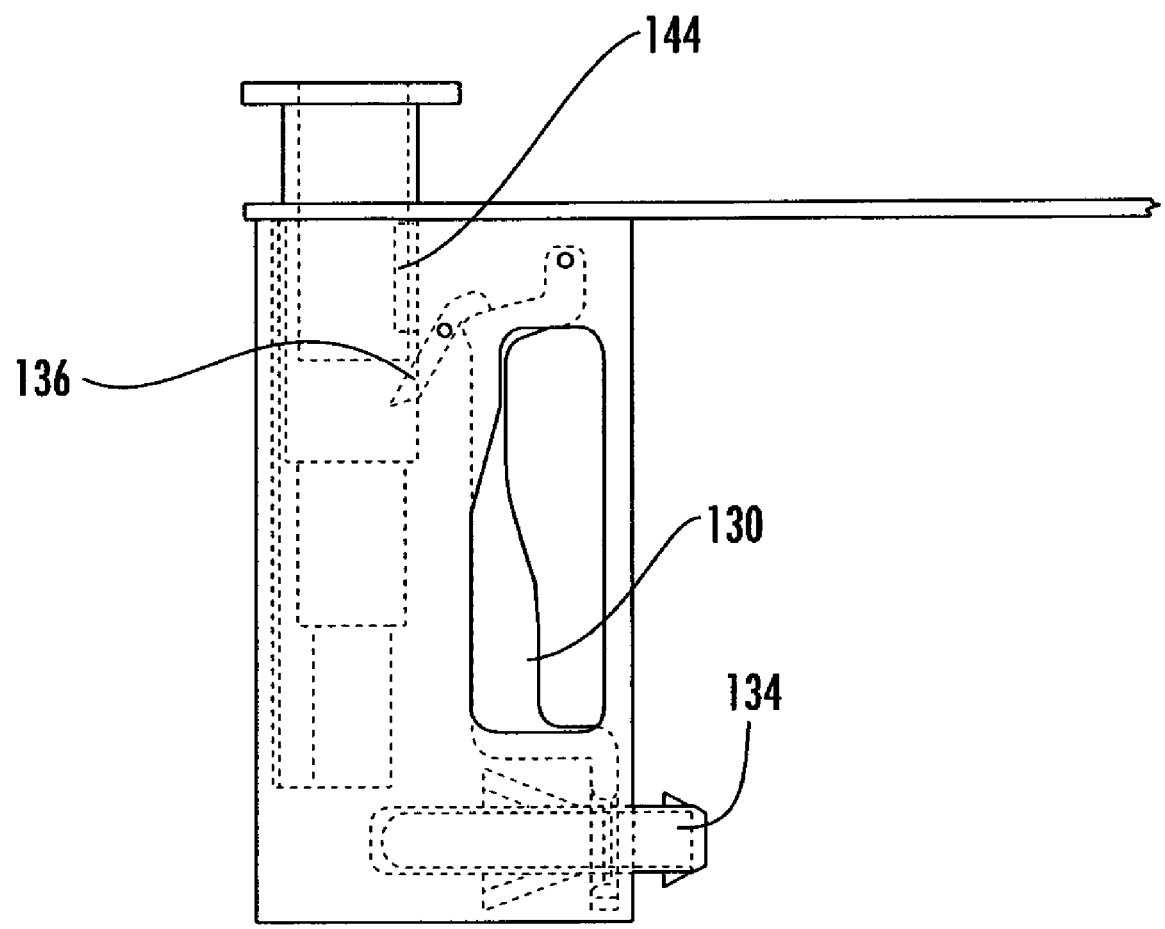
FIG. 45 illustrates the PS3 auxiliary lock ring starting to engage the auxiliary pole lock, a standard auxiliary pole is then inserted inside this lock ring allowing accommodation of the belt strap and an auxiliary pole.

Now with reference to FIG. 45, an embodiment of the PS3 auxiliary lock ring 140 is illustrated as it begins to engage the "locked" position biased auxiliary pole lock 136. The lock ring is provided with a slot or aperture 144 into which auxiliary pole lock 136 can move to secure the lock ring to the auxiliary pole. Note, a standard auxiliary pole can fit inside the lock ring to allow accommodation of both the patient safety strap and an auxiliary pole.

Figure 46:
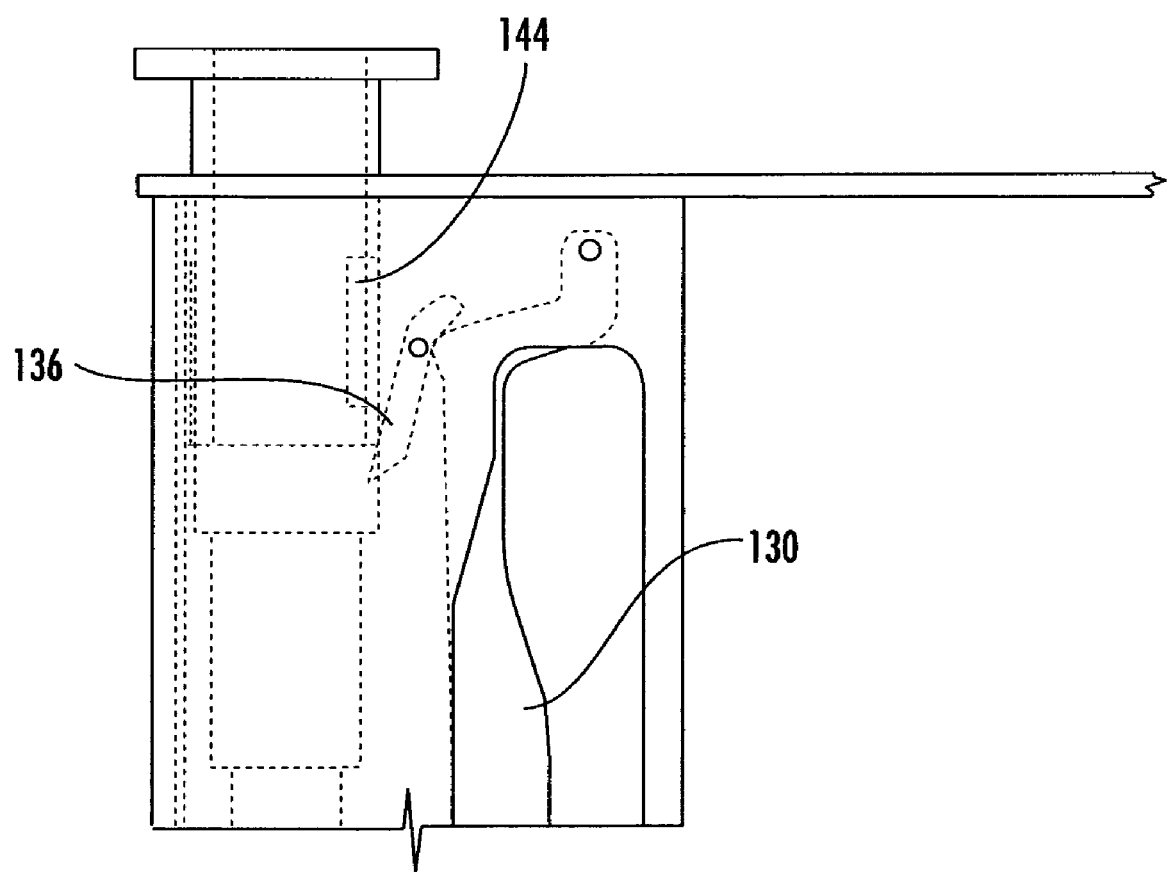
FIG. 46 illustrates the PS3 lock ring "opening" the auxiliary pole lock.

FIG. 46 is the next step wherein the PS3 lock ring is shown starting to engage the auxiliary pole lock 136 to force it to "unlock" prior to self-returning into the slot 144 in the lock ring. Although not herein depicted, it is understood that the engaging leading edges of the auxiliary poles, lock ring and receiving holes' top edges in the auxiliary block may be tapered to aid self-alignment as used throughout the PS3 design.

Figure 47:
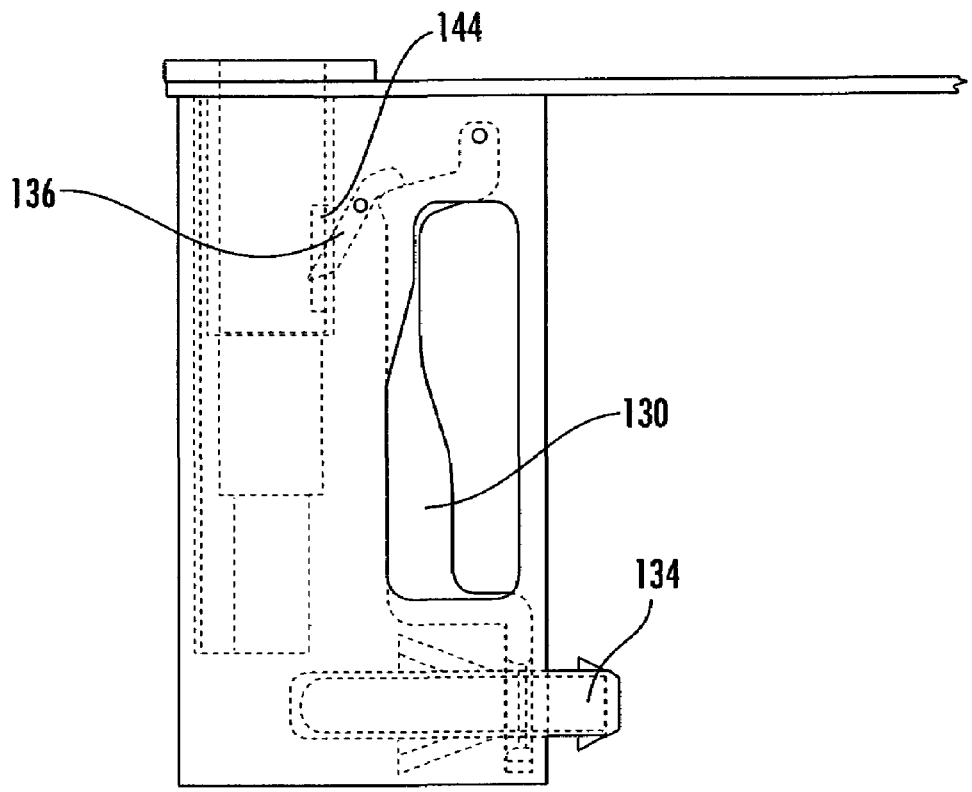
FIG. 47 illustrates the auxiliary pole lock in its locked position.

FIG. 47 illustrates the final step wherein the auxiliary pole lock has self-returned and is fully engaged with the auxiliary block. The auxiliary pole lock 136 is shown in aperture 144 thus securing the lock ring to the auxiliary block.

Figure 48:
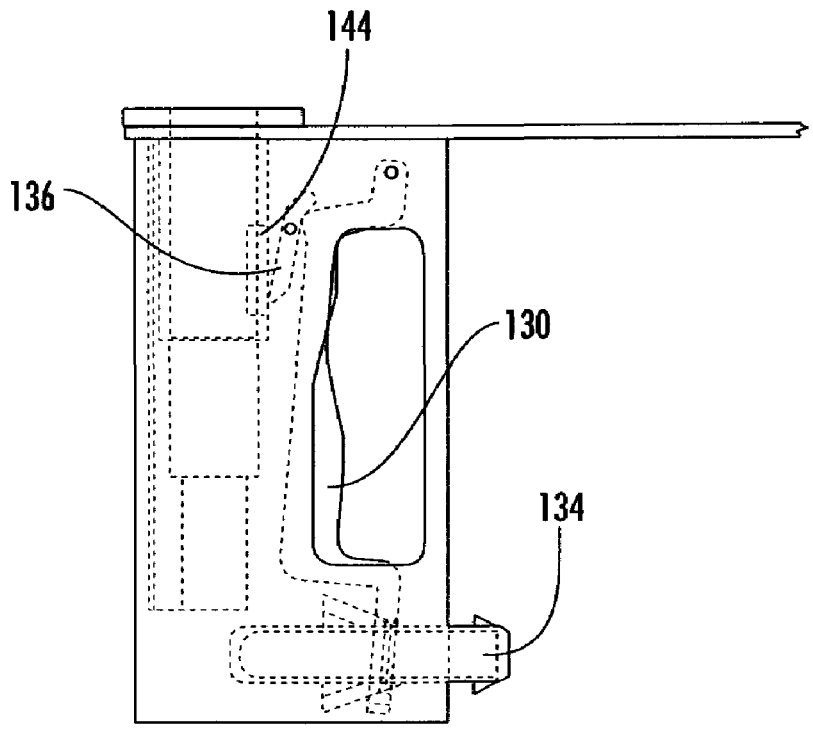
FIG. 48 illustrates the PS3 auxiliary block showing the first phase of the staged release wherein the auxiliary pole lock has completely disengaged the slots in the auxiliary poles or lock ring to allow removal of auxiliary poles or lock ring, while the release lever has just started to engage the self-locking catch.

FIG. 48 is illustrative of positioning of the release lever 130 of the PS3 auxiliary block showing a first phase of staged release. In this figure, the auxiliary pole lock 136 has completely disengaged the slot 144 in the lock ring to allow removal of auxiliary poles and lock ring. In addition, the release lever 130 has just started to engage the self-locking catch ramps 106 of the self-locking catch 134. Note, kinematics are key to allow staged process and proper engagement between the release handle and catch. In addition, the kinematics of the release lever rotation must be correct to properly engage both the top and bottom of the catch.

Figure 49:
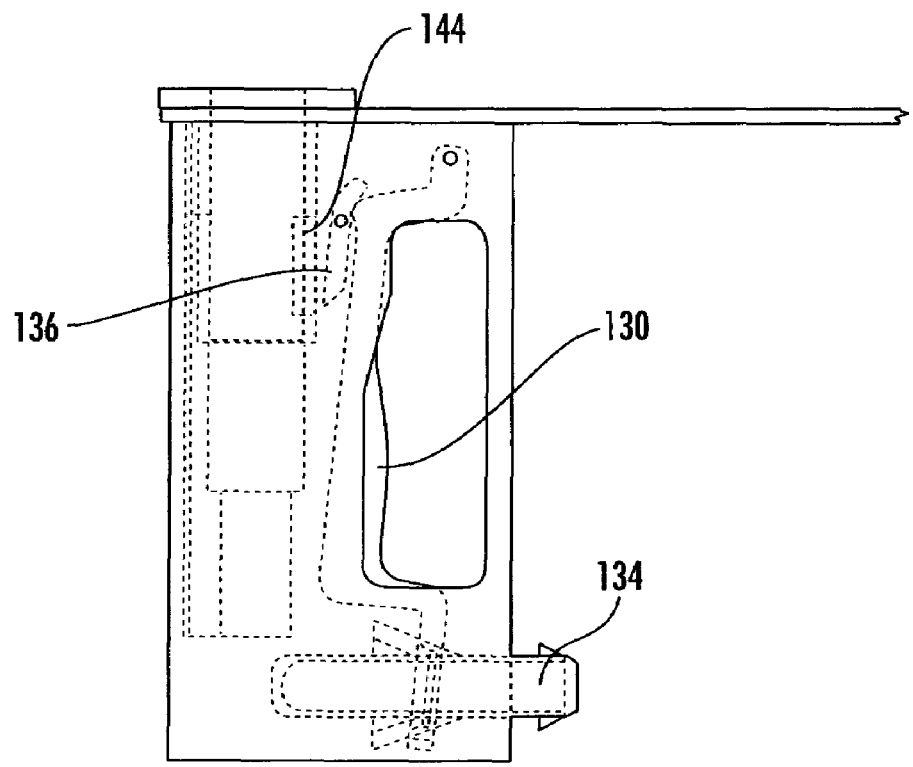
FIG. 49 further illustrates the PS3 auxiliary block showing the second phase of staged release, wherein the release handle has engaged the self-locking catch enough for the catch tips to completely retract.

With reference to FIG. 49, the PS3 auxiliary block is illustrated showing the second phase of staged release. The release handle 130 has engaged the self-locking catch ramps 106 enough for the catch tips 112 to completely retract. (Note catches are not shown retracted).

Figure 50:
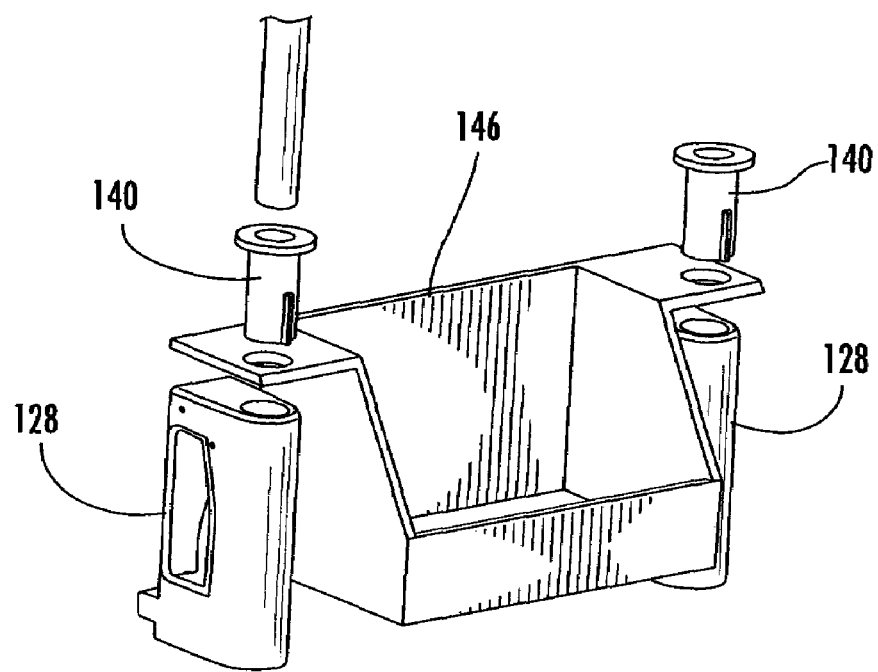
FIG. 50 is an exploded view of a PS3 auxiliary tray assembly which includes an auxiliary tray, two auxiliary block assemblies, two lock rings to lock the assembly together and an auxiliary pole.

FIG. 50 is a front isometric exploded view of a PS3 auxiliary tray assembly 146 which includes: an auxiliary tray, two auxiliary blocks (self-locking assemblies) 128, two lock rings 140 to lock the assembly together and an auxiliary pole, which fits inside the lock ring and is secure in the auxiliary block.

Figure 51:
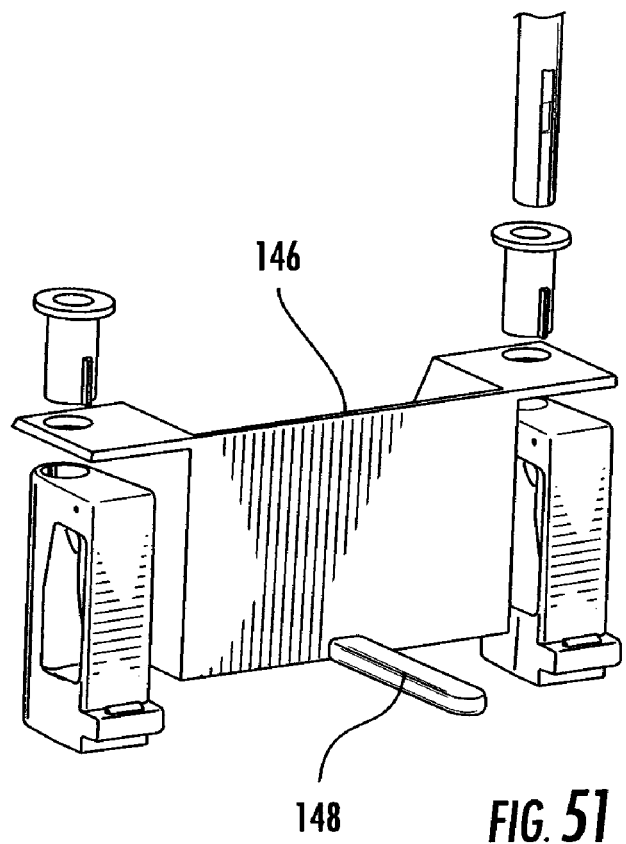
FIG. 51 is a rear of FIG. 50 illustrating the support pin attached to the rear of the auxiliary tray to support heavier loads.

Referring to FIG. 51, a rear isometric exploded view of the PS3 auxiliary tray assembly 146 is provided, which shows the same elements as those in FIG. 50 as well as a support pin 148 to support heavier vertical loading in the auxiliary tray.

Figure 52:
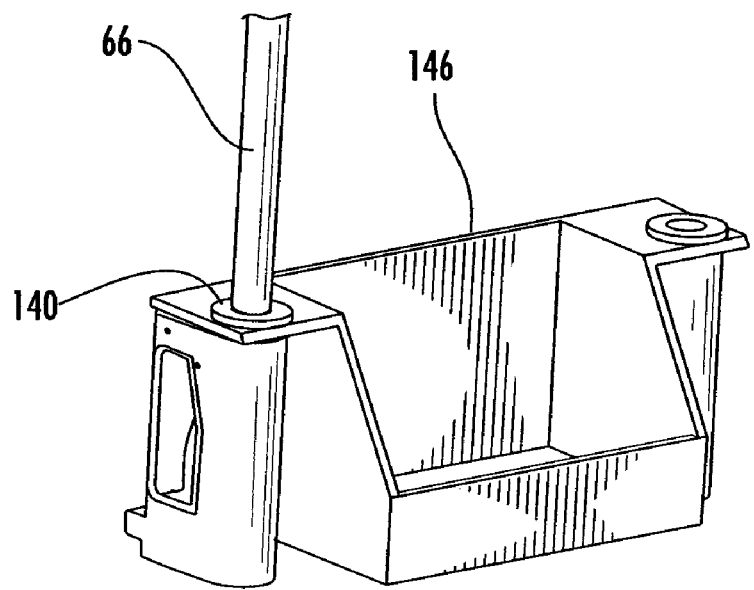
FIG. 52 is a front perspective view of the assembly shown in FIGS. 50 and 51.

FIG. 52 is a front isometric view of the auxiliary tray assembly in an assembled condition shown in FIG. 50 and FIG. 51.

Figure 53:
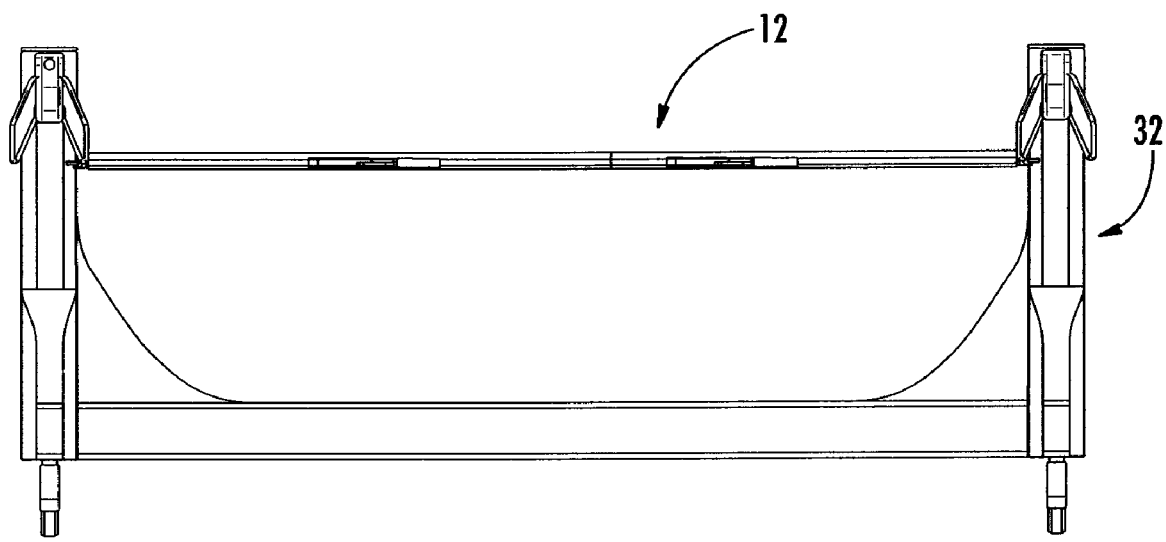
FIG. 53 is a side view of the PS3 assembly with the main single surface platform in a horizontal position.

FIG. 53 is a side view of the PS3 single surface platform 12 (in a horizontal position), frame to single surface interface arms 50 and a new pivot center 40 for one frame to single surface interface arm. The pivot center allows rotation of the frame to single surface interface arms to compensate for the reduction in the horizontal distance (X-Direction) between the two frame to single surface interface arm pairs when the PS3 single surface platform is placed in a Trendelenburg (tilted) position.

Figure 54:
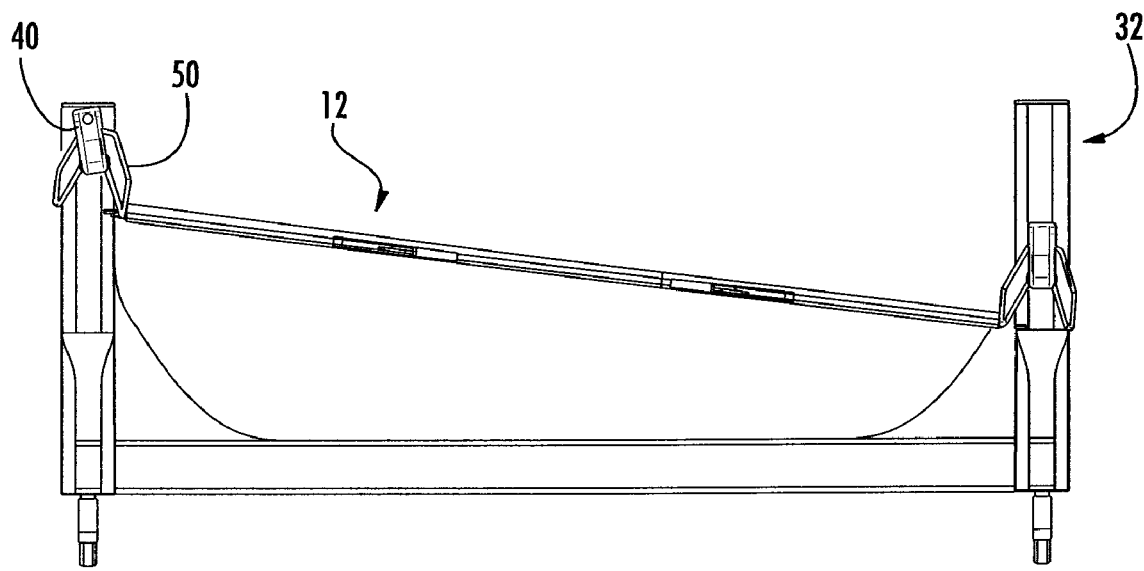
FIG. 54 is a side view of the PS3 assembly with the main single surface platform in a Trendelenburg (tilted) position in which the single surface platform to frame interface arms on the left have rotated about the frame to single surface interface to compensate for the reduction in the horizontal distance between the two frame to single surface interface members.

FIG. 54 is a side view of the PS3 single surface platform in a Trendelenburg (tilted) position in which the frame to single surface interface arm, on the left has rotated about its pivot center accordingly to compensate for the reduction in the horizontal distance between the two single surface to frame interface centers.

Figure 55:
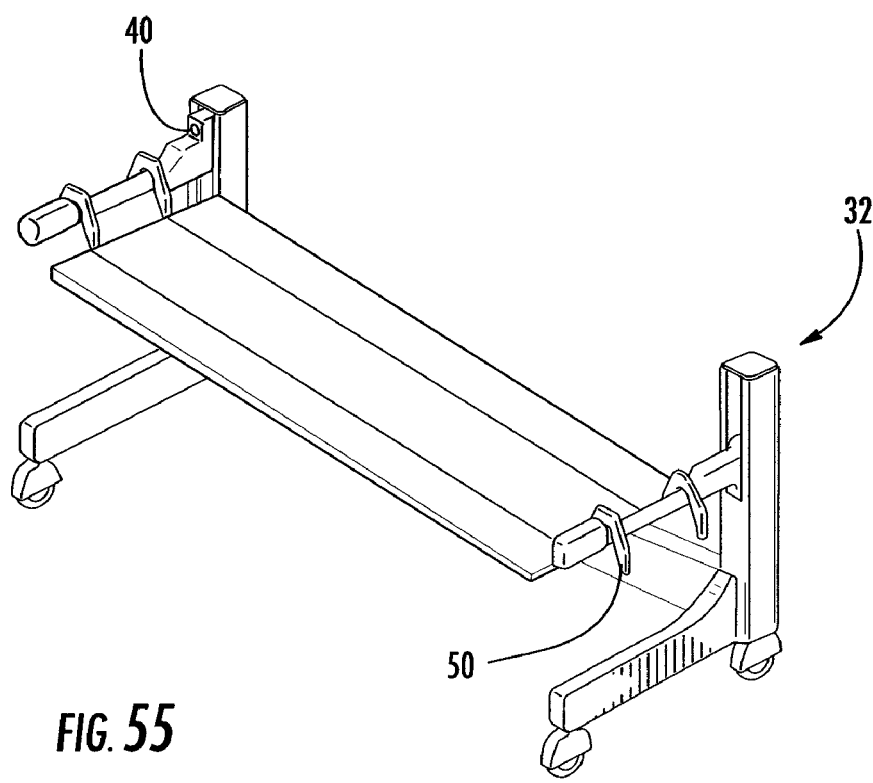
FIG. 55 is an perspective view of the PS3 single surface platform in a Trendelenburg (tilted) position in which one of the frame to single surface members is lower than the other one.

FIG. 55 is an isometric view of the PS3 single surface platform in a Trendelenburg (tilted) position in which the frame to single surface interface arm 40, on the left has rotated about its pivot center accordingly to compensate for the reduction in the horizontal distance between the two single surface to frame interface centers. Note a round interface between the frame to single surface arms and the single surface to frame interface hooks is still required for Trendelenburg (full bed tilt) as shown.

Figure 56:
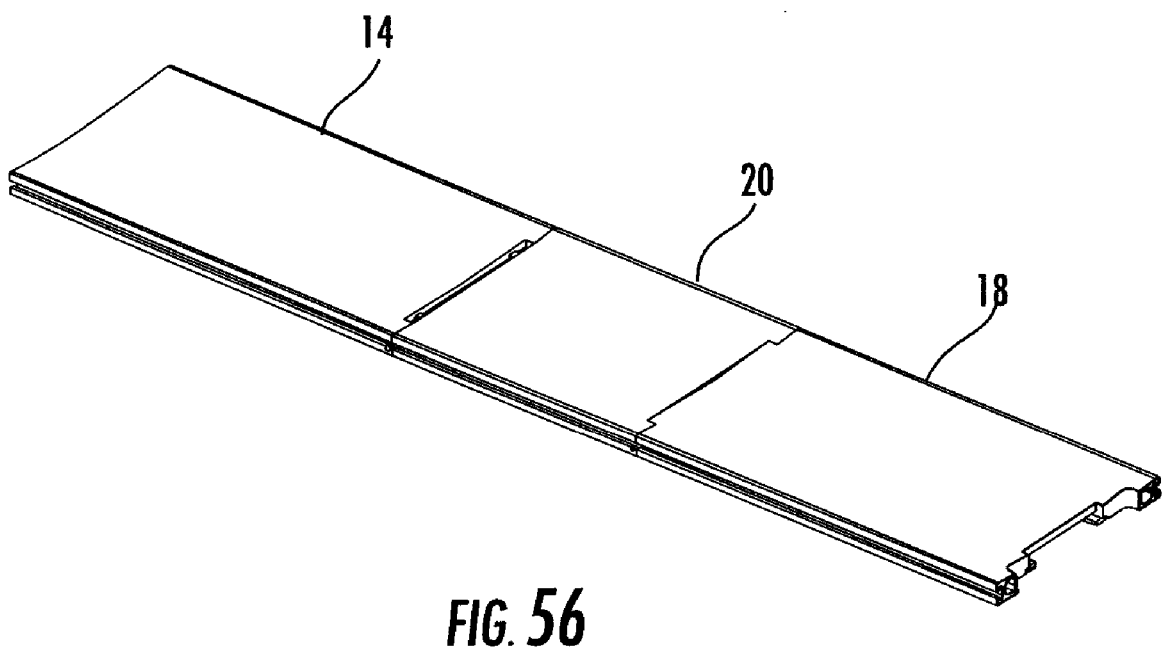
FIG. 56 is a top perspective view of the PS3 main single surface platform including an upper body section and a knee gatch section.

FIG. 56 is a top isometric view of a three segment base PS3 single surface platform without the articulation inter-lock system 152 and single surface to frame interface hooks. Labeled specifically are the single surface backrest or uppermost section 14, the single surface mid or middle section 20 and the single surface knee gatch or lowermost section 18 with hinged interface/joints therebetween. The construction of this single surface platform would likely be of a composite exterior shell utilizing, for example structural foam, honeycomb, balsa wood, etc. for core for stiffness to weight, X-Ray translucency and non-magnetic (MRI) compatibility. The T-Slots would likely be extruded or machined in plastic and sandwiched in the composite shell. All aspects of the PS3 single surface platform design facilitate the use of non-ferrous materials. This rigid backboard mode is intended for just that, a backboard, to facilitate usage by the EMS.

Figure 57:
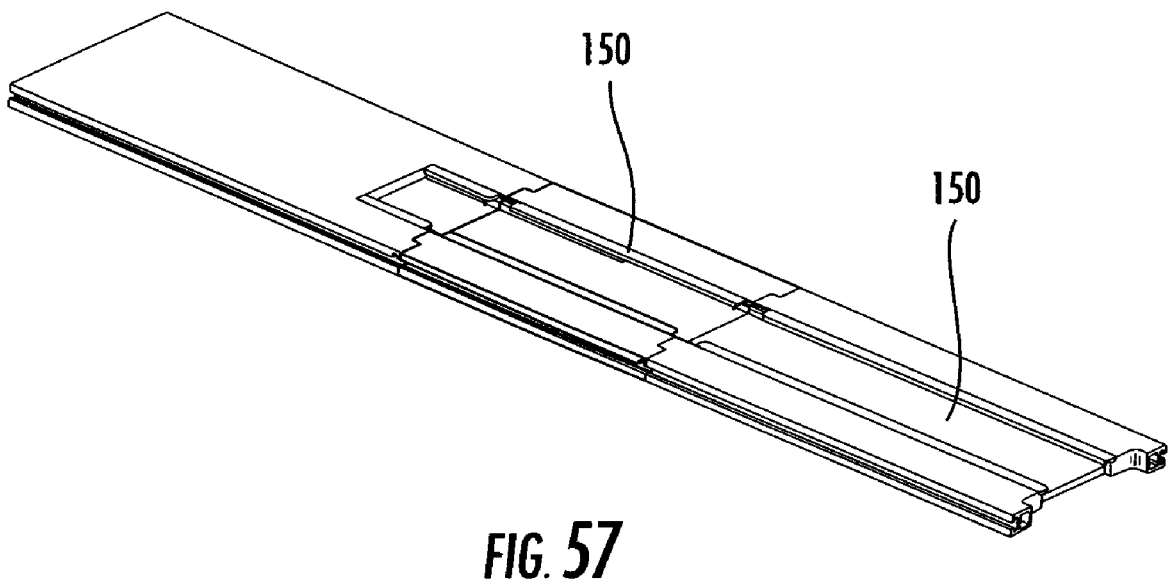
FIG. 57 is a bottom perspective view of the PS3 main single surface platform without the interlock/interface module and single surface platform to frame transfer arms.

FIG. 57 is a bottom isometric view of the base three segment PS3 single surface platform without the articulation inter-lock system and single surface to frame interface hooks. Labeled specifically are the recesses 150 for the articulation inter-lock system.

Figure 58:
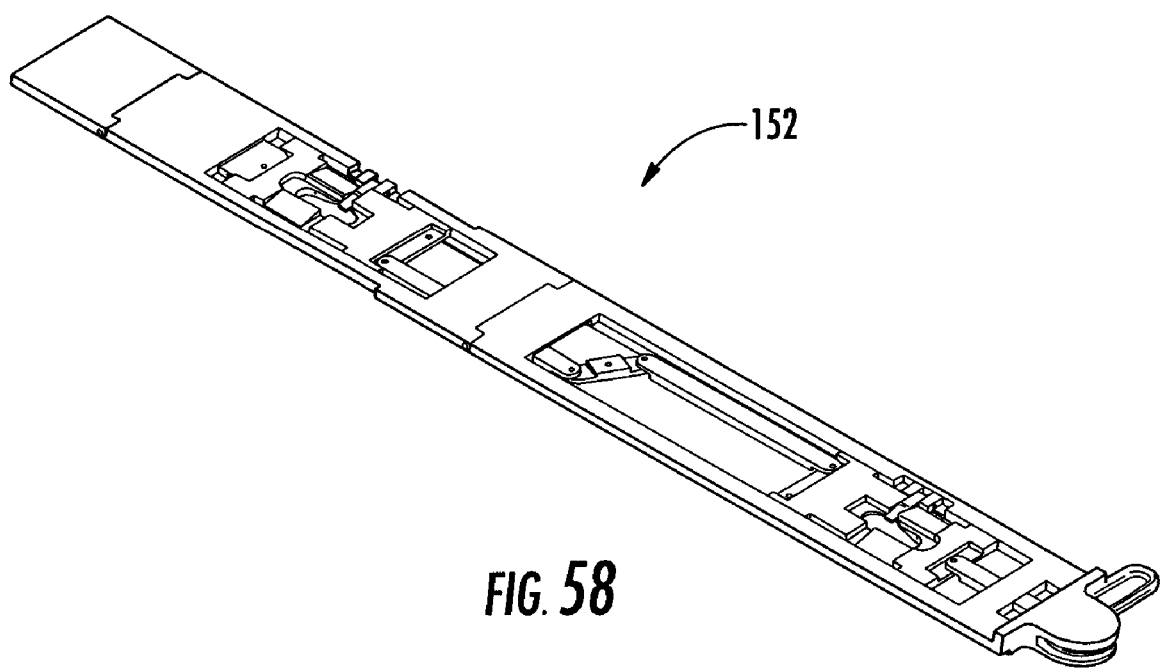
FIG. 58 is a top perspective view of a removable three segment self-contained interlock/interface module which cooperates with the main single surface platform of FIGS. 56 and 57.

FIG. 58 illustrates a top isometric view of the three segment self-contained articulation inter-lock module system. This figure and FIG. 63 through FIG. 66 show the same basic inter-lock mechanisms and include therein the self-contained articulation system itself and the addition of lock and unlock for the knee gatch section.

Figure 59:
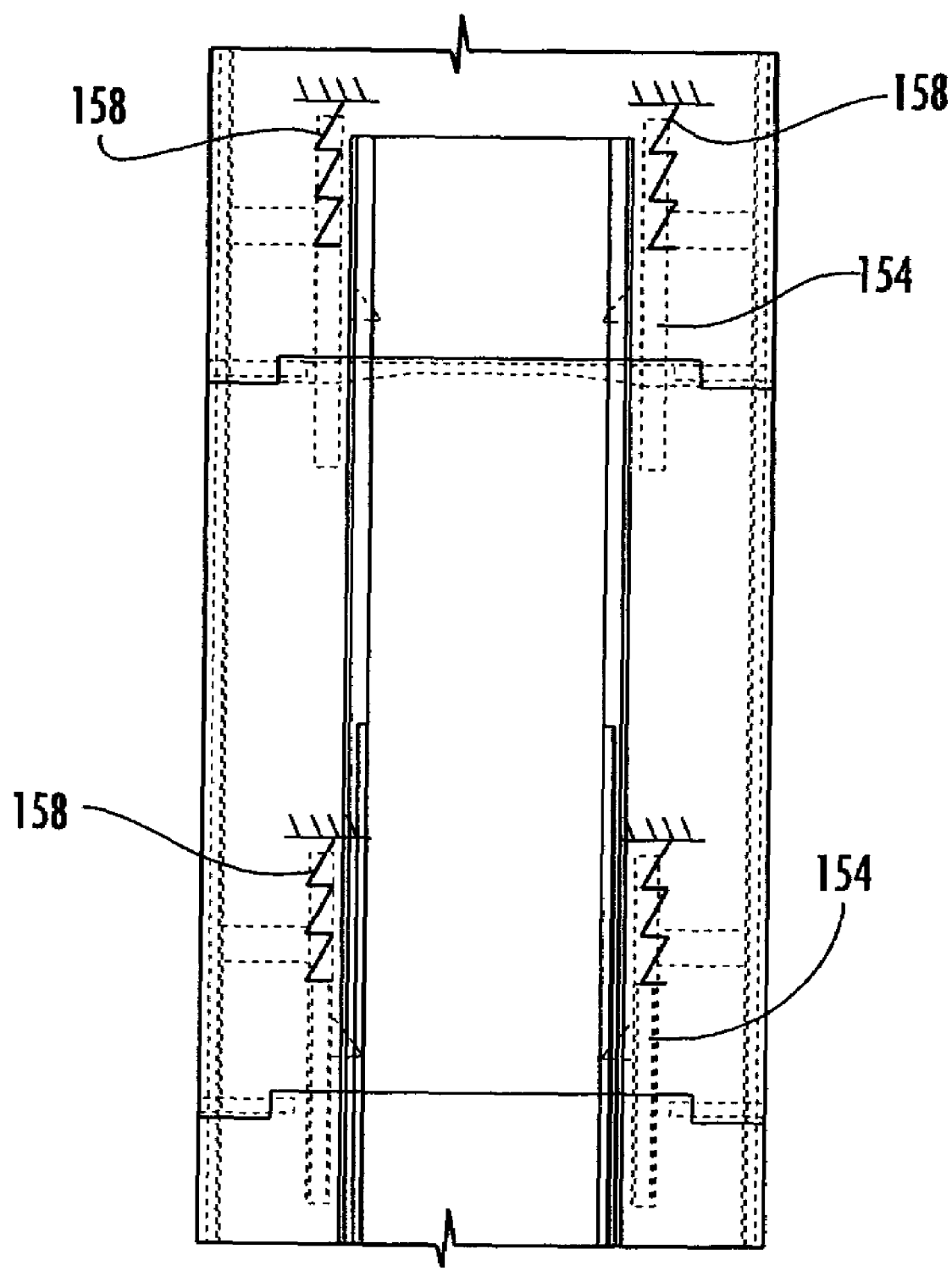
FIG. 59 is a bottom partial view of a base three segment PS3 single surface platform without the interlock/interface module and module retainer plates. It also shows the tilt/bend lock tubes connecting the upper body section and the main single surface platform section. Also the tilt/bend lock tubes connect the lower leg section to the main single surface platform section.

FIG. 59 illustrates a bottom view of the base three segment PS3 single surface platform without the articulation inter-lock system 152 and module retainer plates. It shows a portion of the single surface backrest portion and the single surface knee gatch and all of the single surface mid portion. It also again highlights the pivot centers hinged interface/joint between the single surface backrest portion and single surface mid portion and the hinged interface/joint between the single surface mid portion and single surface knee gatch section. FIG. 59 further illustrates the spring loaded tilt/bend lock tubes 154. The tilt/bend lock tubes that translate longitudinally are shown normally spring loaded in position to "lock out" or prevent any tilting or bending of the three segments maintaining a single flat surface. Spring 158 provides the bias to hold the tilt/bend lock tubes in this position. The spring could be a non-ferrous coil design or a composite or non-ferrous leaf spring as is the case for anything of the "spring-loaded" mechanisms in PS3. Also shown are tips 156 on the tilt/bend lock tubes which contact specific points on the articulation inter-lock system to retract the lock tubes. When the self-contained articulation system 152 is inserted into the apertures 150 in the single surface platform (FIG. 57) the top edge and the stepped edge of the articulation system engage the tips 156 of the tilt/bend lock tubes 154 and push the tubes upwardly (FIG. 59) disengaging the connection between the backrest portion and mid portion and also between the mid portion and the knee gatch. The self-contained installed articulation interlock module takes "control" of locking out the articulation of the backrest and knee gatch joints prior to the complete retraction of the lock tubes. The articulation inter-lock module self-locks into place via the same self-lock catch and release mechanisms described throughout PS3.

Figure 60:
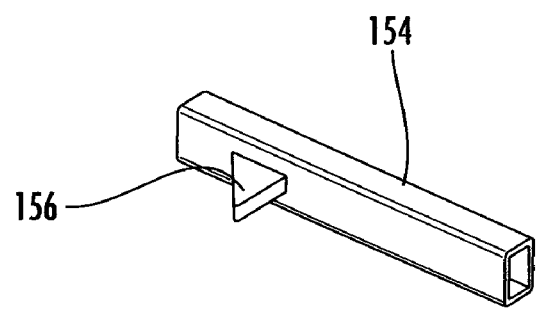
FIG. 60 is an perspective view of the tilt/bend lock tube.

FIG. 60 is an isometric view of the tilt/bend lock tube 154 including tip 156.

Figure 61:
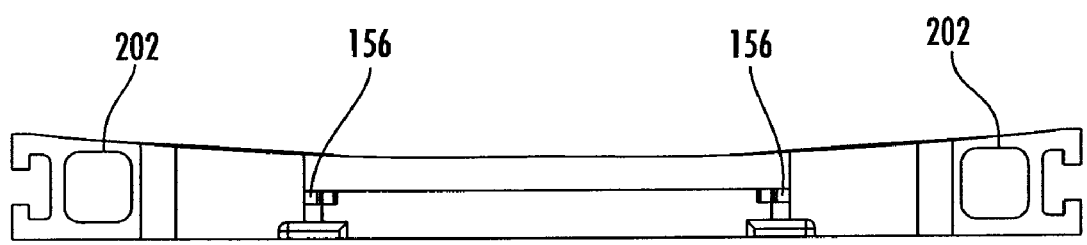
FIG. 61 is an end view of the PS3 single surface platform without the interlock/interface module, illustrating the tips of the tilt/bend lock tubes that interface the interlock/interface module.

FIG. 61 represents an end view of the PS3 single surface platform without the articulation inter-lock system and single surface to frame interface hooks. Shown are the horizontally staggered tips 156 of the tilt/bend lock tubes that interface the articulation inter-lock system. Note, tips of the tilt/bend lock tubes could be alternatively staggered vertically. This figure also illustrates the apertures 202 for attachment of the extension on the single surface to frame interface.

Figure 62:
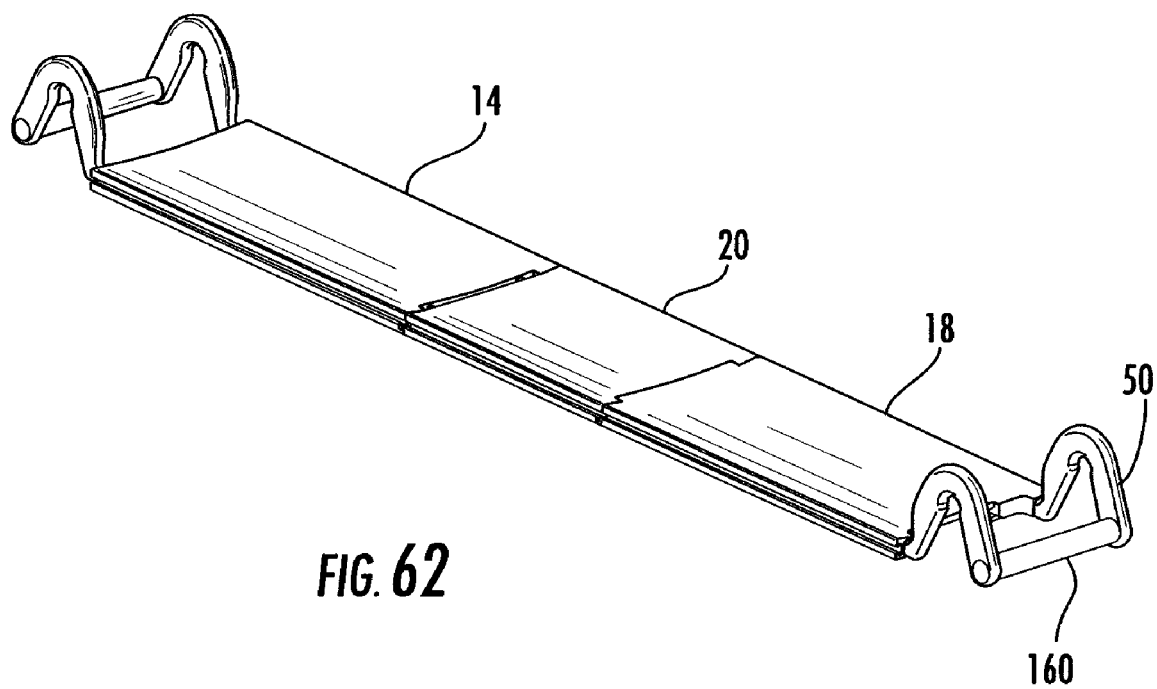
FIG. 62 is a perspective view of the three segment PS3 main single surface platform, without the interlock/interface module, including single surface platform to frame interface hooks which have been provided with a cross bar so they can be used as handles.

FIG. 62 is a top isometric view of the base three segment PS3 single surface platform without the articulation inter-lock system, but with the single surface to frame interface hooks. Cross bars 160 are provided between the hooks and can be used as a handle or receiver for the interface hooks.

Figure 63:
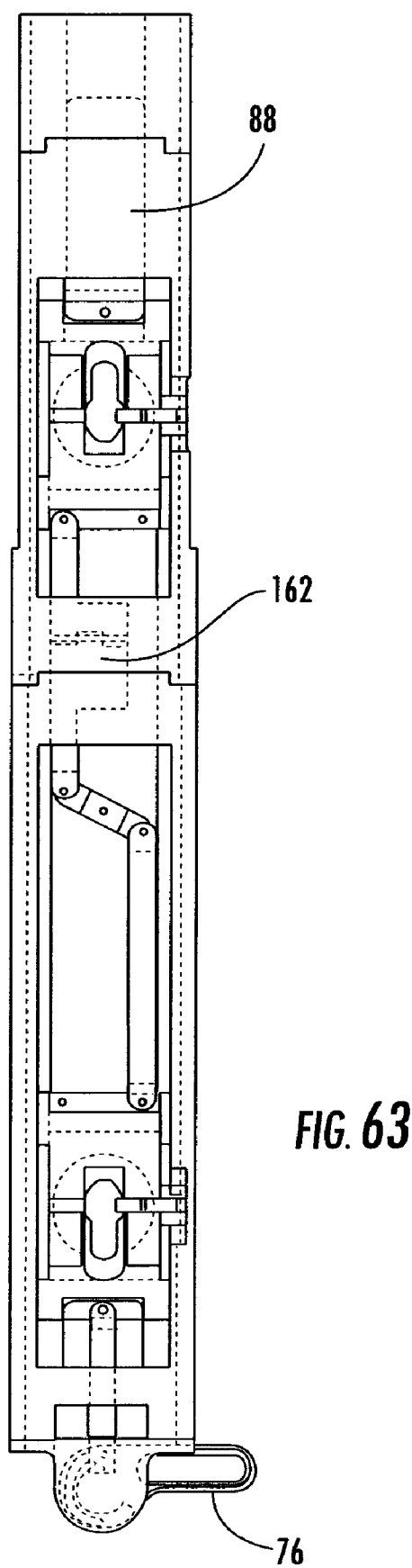
FIG. 63 is a top view of a three segment interlock/interface module with the mechanisms in the locked position.

FIG. 63 is a top view of the three segment separable self-contained articulation inter-lock system 152 shown in FIG. 58 with the mechanisms in the locked position. Backrest lock bar 88 locks the mid portion to the backrest portion. Knee gatch lock bar 162 locks the mid portion to the knee gatch such that the three single surface platform segments are not allowed to bend at the hinge joints.

FIG. 63 through FIG. 66 show the same basic inter-lock mechanisms as described in the document in FIGS. 18 through 27 of the detailed description overview with the following additions involving the inter-lock system itself and the addition of lock and unlock for the knee gatch segment. The first addition is comprised of the knee gatch lock bar 162 for the knee gatch segment and a corresponding hinge lock bar. Note, these figures initially show the four bar member and lock bar in position such that the segments cannot articulate. In addition, these figures show surfaces which contact the tips on the tilt/bend lock tube in FIG. 59 and FIG. 60. This interface and significance is described in further detail below in FIG. 67 and FIG. 68.

Figure 64:
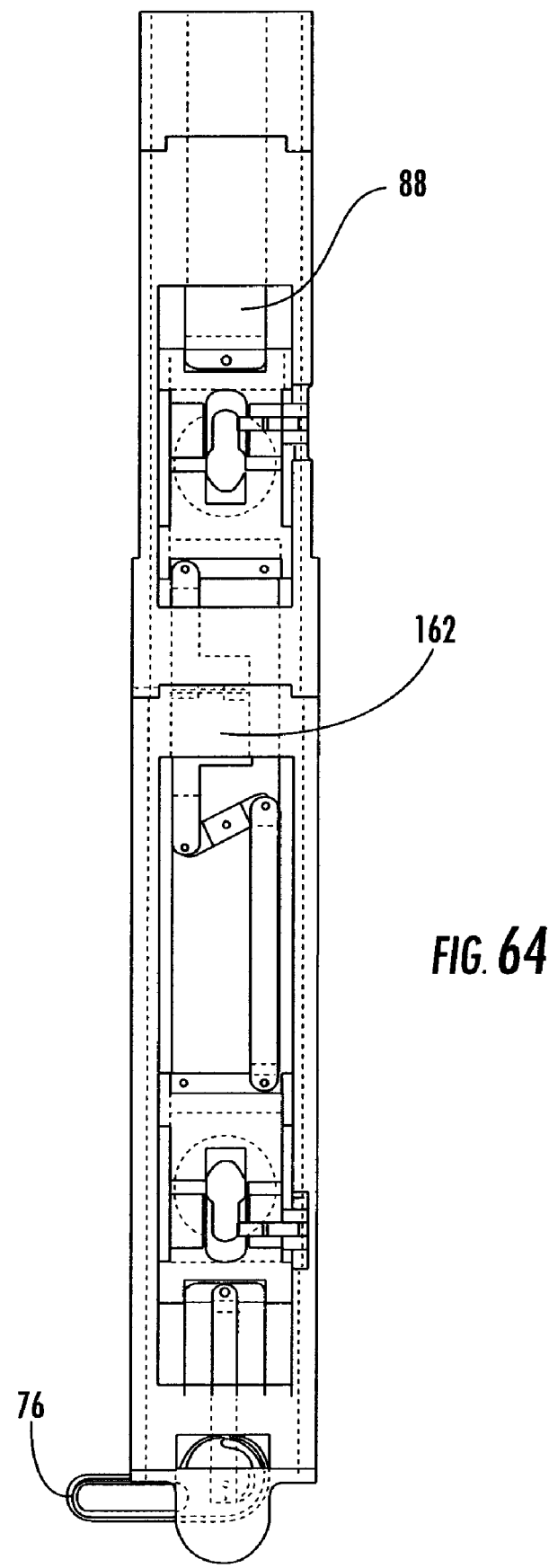
FIG. 64 is a top view of a three segment interlock/interface module with the mechanisms in the unlocked position.

FIG. 64 is a top view of the three segment articulation inter-lock system with the mechanisms in the unlocked position. The three segments and corresponding single surface platform portions are allowed to bend at the hinges. This figure now shows the elements positioned such that the portions can articulate. The hinge joint of the single surface platform is aligned with the hinge joint of the articulation inter-lock system to allow this articulation along with full retraction of the knee gatch lock bar 162. A simple revolute hinge can be used at the hinge joint, however, a spherical joint could be used as well to allow for some misalignment of the hinge axis or a flexible coupling/joint. Use of this same design provides an ability to add segments and add hinge joints to the corresponding four bar mechanism such that the additional joints align with the new segment joint when the entire mechanism is in the unlock position. T-pins, although required to unlock the interlock plate module, are not shown in these figures.

Figure 65:
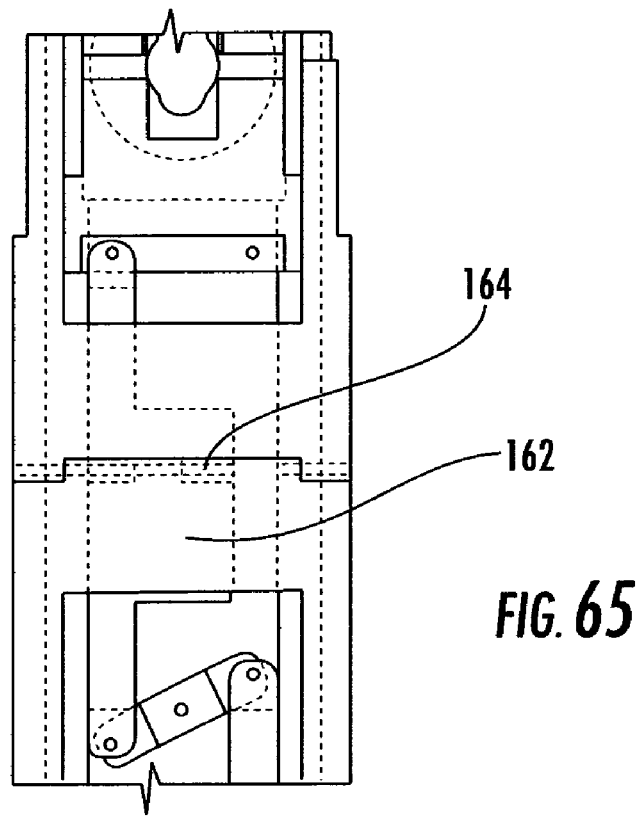
FIG. 65 is a partial view of a three segment interlock/interface module illustrating the alignment between hinge joints on the interlock/interface module and the four bar member, which allows articulation of the single surface backrest portion, mid portion and knee gatch portion.

FIG. 65 is directed toward a zoomed in top view of the alignment between hinge joints on the articulation inter-lock system and the single surface platform, which ultimately allows articulation of the single surface knee gatch portion with respect to the mid portion.

Figure 66:
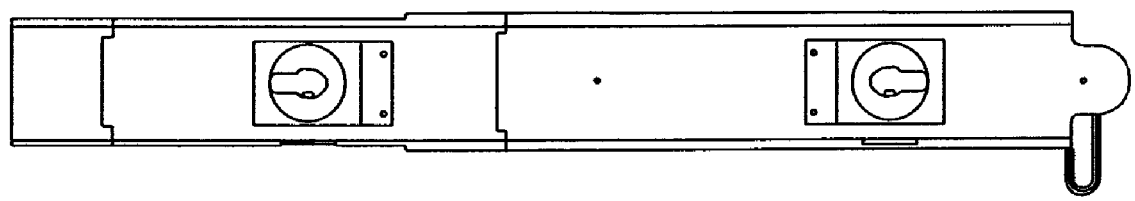
FIG. 66 is a bottom view of the complete interlock/interface module.

FIG. 66 is a bottom view of the complete self-contained articulation inter-lock system 152.

Figure 67:
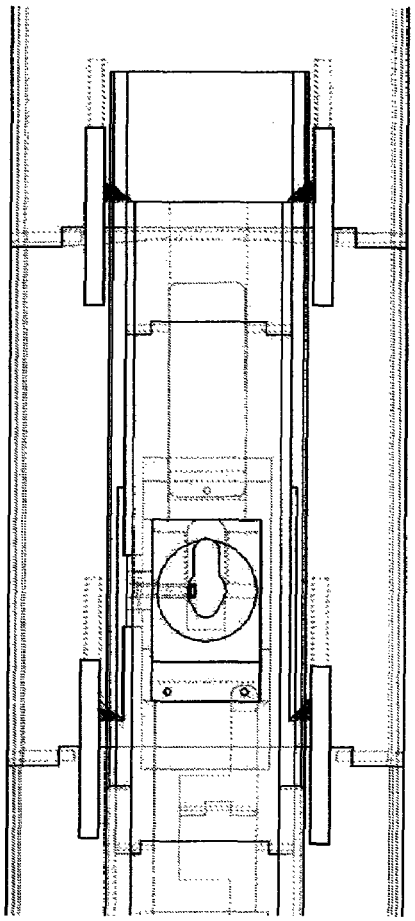
FIG. 67: is a bottom view in part of the interlock/interface module docking into the PS3 single surface platform and just starting to engage the tilt/bend lock tubes.

FIG. 67 is a bottom view of the articulation inter-lock system 152 sliding/docking into the PS3 single surface platform and just beginning to engage the tips of the tilt/bend lock tubes. The stagger of the lower interface is required to properly engage the tilt/bend lock tubes. As illustrated, the tilt/bend lock tubes are in their baseline position which is maintained by the four springs 158, thereby locking the three segment PS3 single surface platform into one flat surface at this point.

Figure 68:
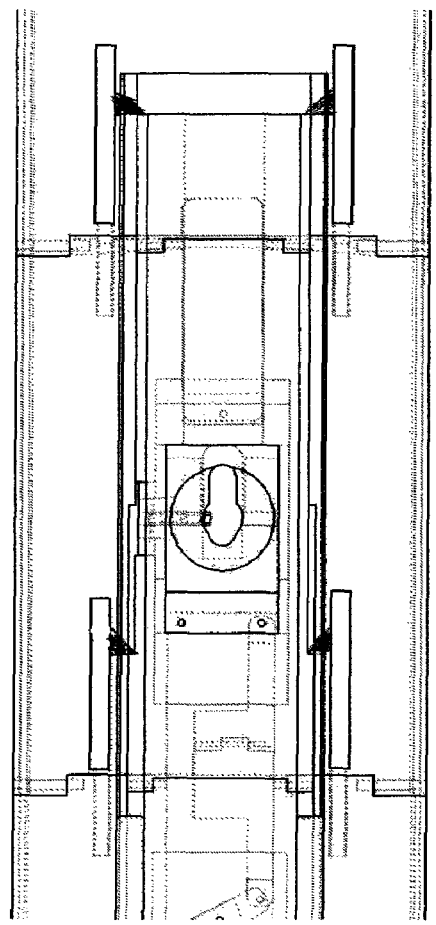
FIG. 68: is a bottom view in part of the interlock/interface module in its final position in the PS3 Single surface platform in which it has fully retracted the tilt/bend lock tubes beyond the hinge joints.

FIG. 68 is a bottom view of the articulation inter-lock system 152 in its final position in the PS3 single surface platform in which it has fully retracted the tilt/bend lock tubes beyond the hinge joints. At this point the articulation inter-lock system 152 controls articulation of the PS3 single surface platform joints. As described earlier, the inter-lock plate modules cannot be released without the two required T-Pins (mated to a separate surface like a gurney) engaged into the inter-lock plate module. Therefore, the articulation inter-lock system will always be in the locked configuration (no articulation of PS3 Single Surface joints allowed) while docking or removing the articulation inter-lock system. In addition, the four springs automatically force the four tilt/bend lock tubes back into a position, which securely locks out articulation of the hinge joints. Therefore, this design combination allows rapid installation and removal of the articulation inter-lock system without the chance of accidentally allowing articulation of the PS3 single surface platform hinge joints.

Figure 69:
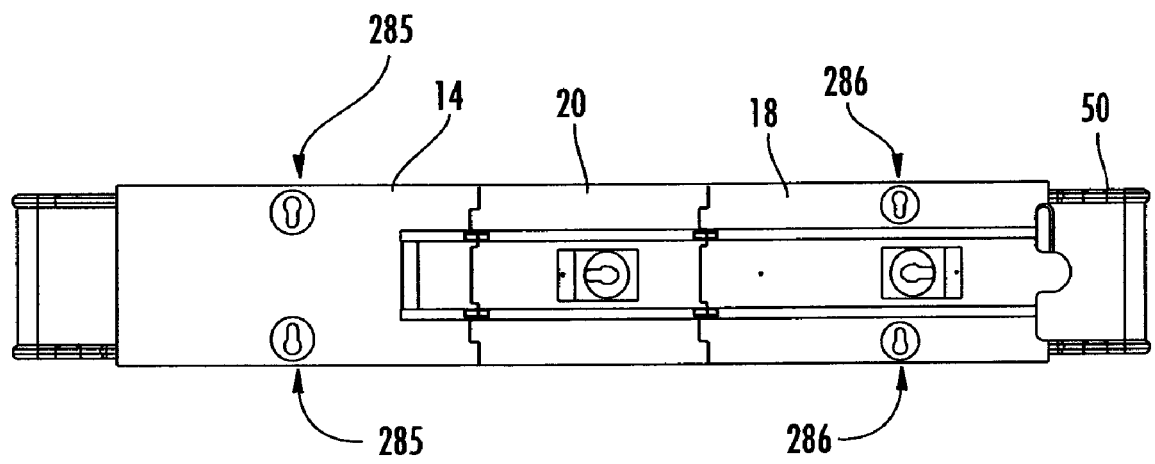
FIG. 69 is a bottom view of the assembled PS3 single surface platform, interlock/interface module and single surface platform to frame interface hooks.

FIG. 69 is a bottom view of the assembled PS3 single surface platform (14, 18, 20), articulation inter-lock system and single surface to frame interface hooks 50.

Figure 70:
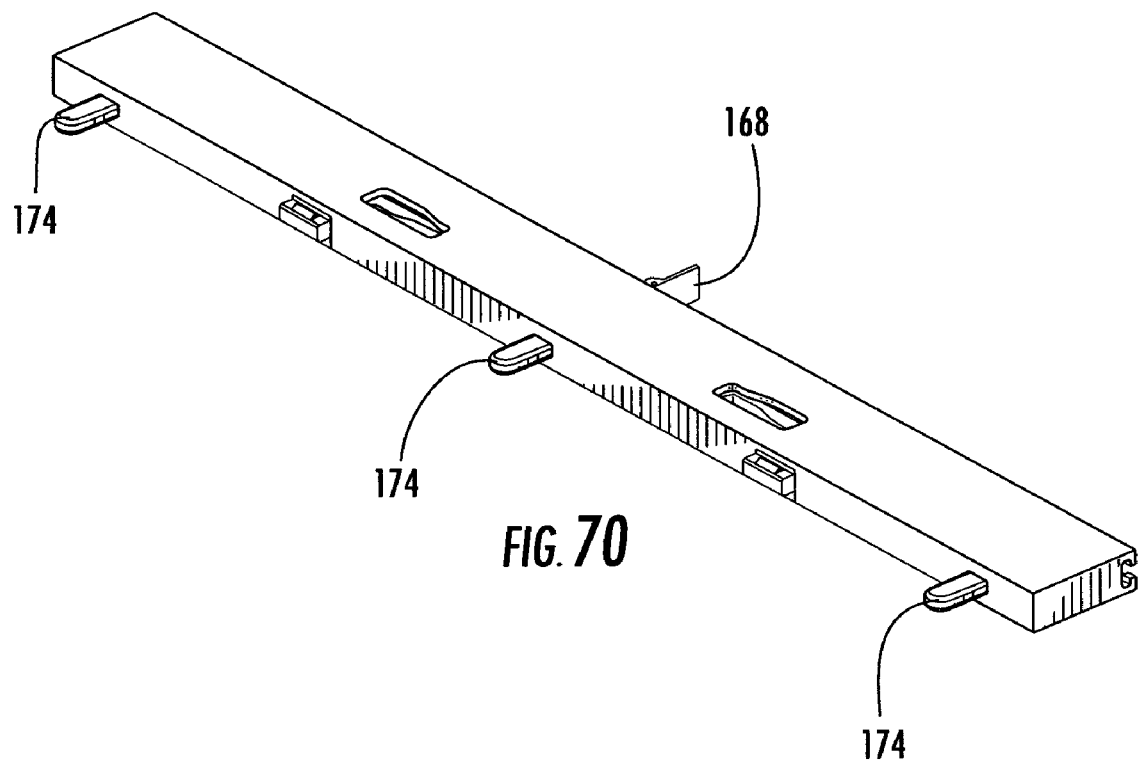
FIG. 70 is a top perspective view of a complete PS3 single surface platform wing assembly.

FIG. 70 illustrates a top isometric view of a complete PS3 single surface wing assembly. The wing is provides with three support pins 174 which provide additional support between the wing and the platform. Also an eccentric tension lever 168 is shown which will be described later.

Figure 71:
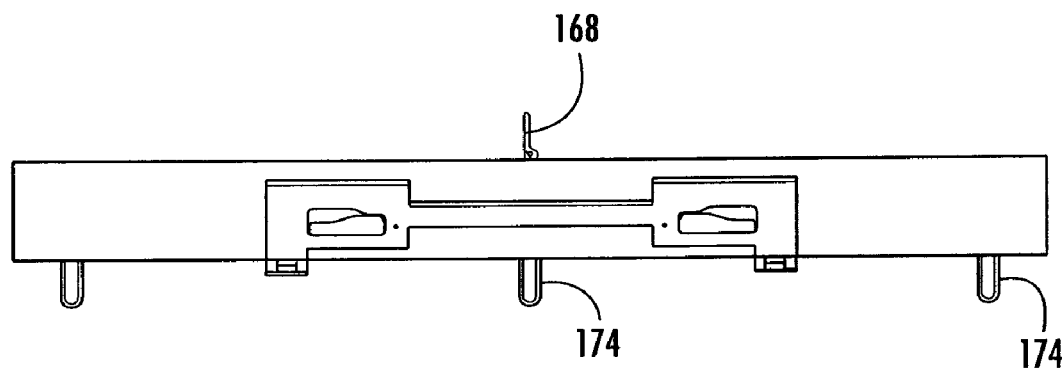
FIG. 71 is a bottom view of a complete PS3 single surface platform wing assembly.

FIG. 71 is a bottom view of the complete PS3 single surface wing assembly highlighting the inclusion of the wing catch/tension/release module 166 (FIG. 72), which comprises a pair of self-locking catch mechanisms and release levers joined by a bar 172. There could also be a single mechanism at the center of the wing for a wing of a shorter length.

Figure 72:
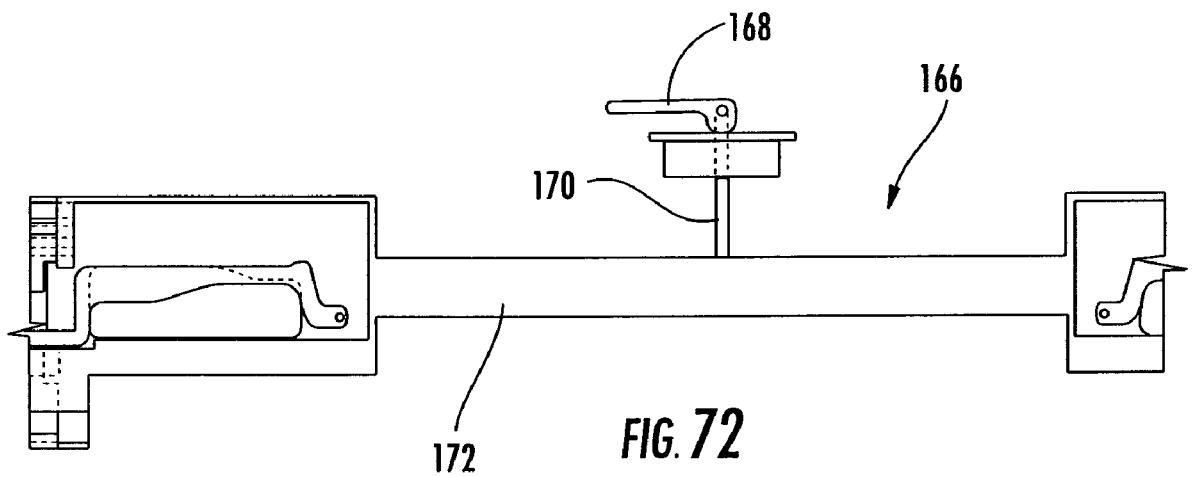
FIG. 72 is a perspective view of the wing catch/tension/release module removed from the single surface platform wing.

FIG. 72 is an enlarged top view of the wing catch/tension/release module 166 highlighting the parts thereof which include the eccentric tension lever 168, and the tension bar 170. The eccentric tension lever is shown in the "locked" position. Tension bar 170 is eccentrically mounted to the eccentric tension lever and connected to bar 172 connecting the catch mechanisms. Movement of the tension bar 170 by actuation of the tension lever 168 causes translation of the wing catch/tension/release module relative to the wing body itself due to the offset or eccentric nature of the pivot center versus the outer radius or cam profile of the tension lever 168. The tension bar 170 is threaded into the wing catch/tension/release bar 172, which allows for adjustment of the tension of the wing to the single surface platform side.

Figure 73:
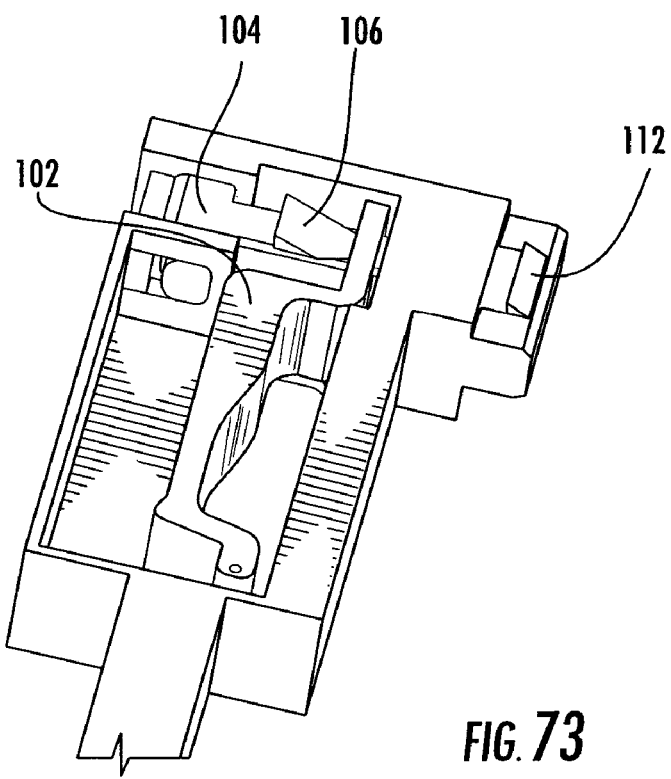
FIG. 73 is a perspective view of the wing catch/tension/release element.

FIG. 73 is a top isometric view of one of the wing catch/tension/release module elements. A release handle 102 engages the ramped portion 106 of the self-locking catch 104 thereby retracting catch the self-locking tips 112 from engaging the T-slots in the in single surface platform or wings.

Figure 74:
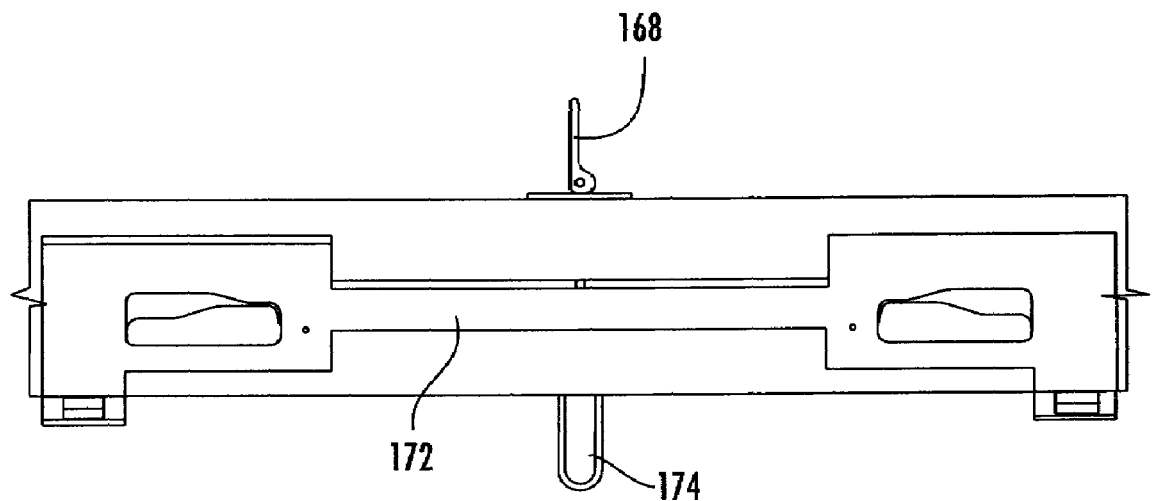
FIG. 74 is a bottom view is part of a PS3 single surface platform wing assembly with the eccentric tension lever of the wing catch/tension/release element in the unlocked position.

FIG. 74 is a bottom view of the complete PS3 single surface wing assembly with the eccentric tension lever 168 in the unlocked position. Note the gap between the wing catch/tension/release module and the wing itself and compare it to the gap in FIG. 75.

Figure 75:
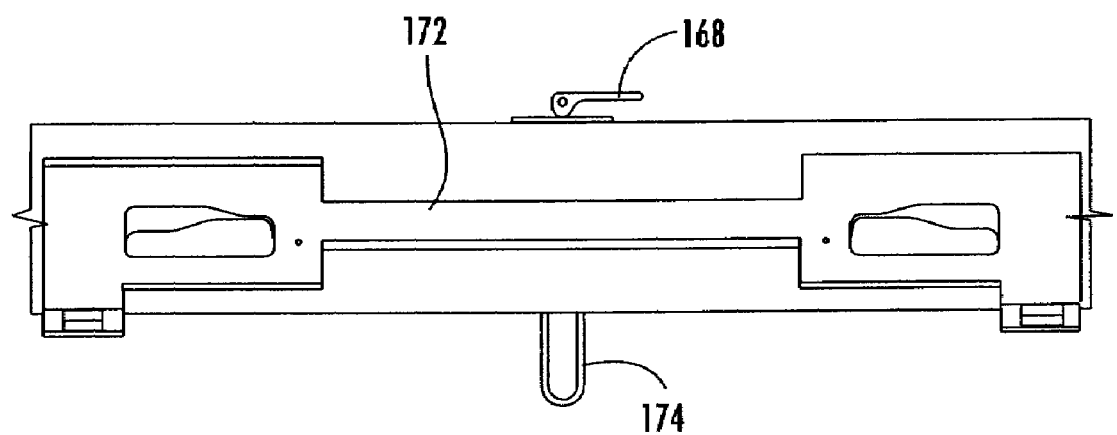
FIG. 75 illustrates the PS3 single surface platform wing assembly of FIG. 74 with the eccentric tension lever in the locked position.

FIG. 75 is a bottom view similar to FIG. 74 of the complete PS3 single surface wing assembly with the eccentric tension lever 168 in the locked position. Note that the gap between the wing catch/tension/release module and the wing itself has closed as the catch/tension/release module is moved upward. This relative movement upward causes the self-locking catches to pull the wing tight into the single surface platform side. Note this same tension and release system could be used on the prior described auxiliary block assemblies if desired.

Figure 76:
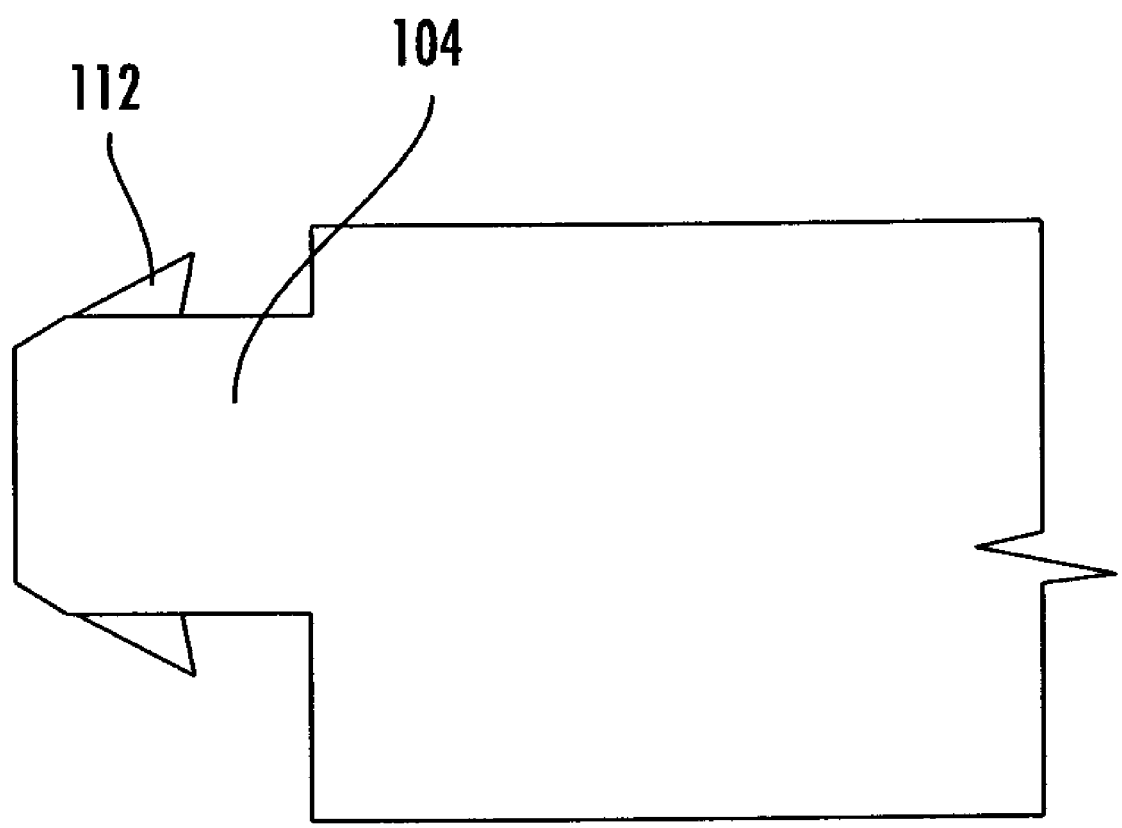
FIG. 76 is end view of the self catch/latch of the wing catch/tension/release element of FIGS. 74 and 75.

FIG. 76 represents an end view of the self-locking catch. The back side edge of the tips 112 are angled rearward from vertical, which contacts the vertical mating surface on the T-Slot on the single surface platform (the prior design showed this surface to be purely vertical). The rearward angle means the tip 112 of the self-locking catch will contact the T-slot before its base does and will provide a more secure lock into the T-Slot. This back angle will cause the self-locking catch tips to lock/bite into the T-Slot when the eccentric tension lever 168 is locked, which will not allow one to release the wing with the release levers until the eccentric tension lever is unlocked.

Figure 77A:
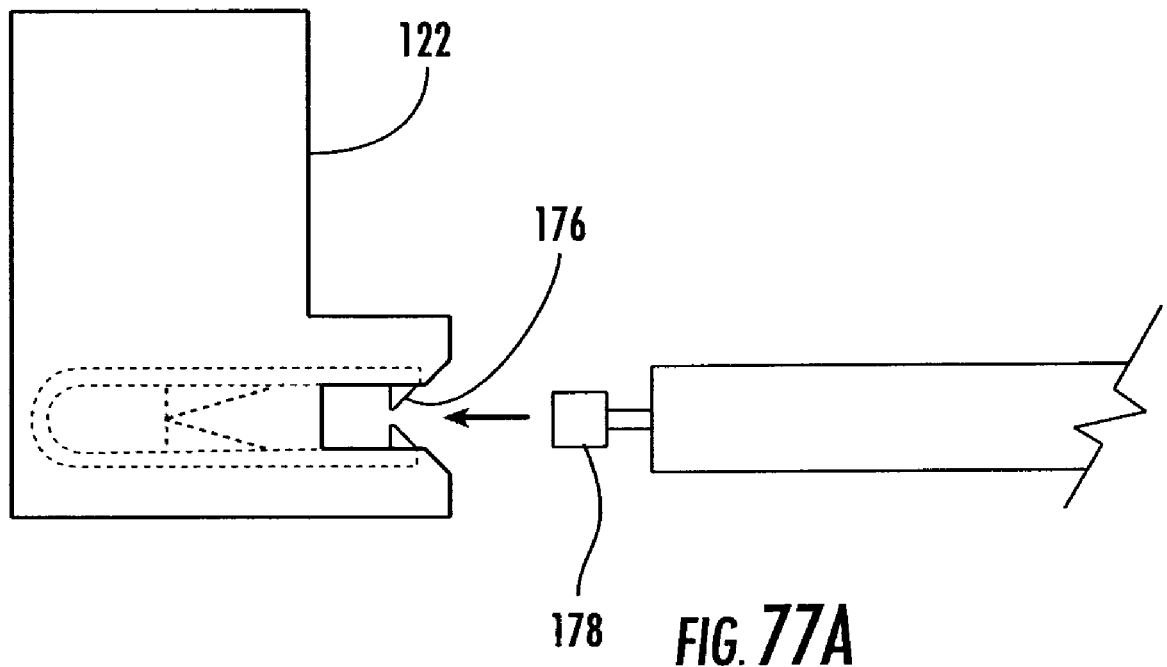
FIG. 77A is an end view of a rectangular or square single surface platform rail and a self catch auxiliary block prior to engagement.
Figure 77B:
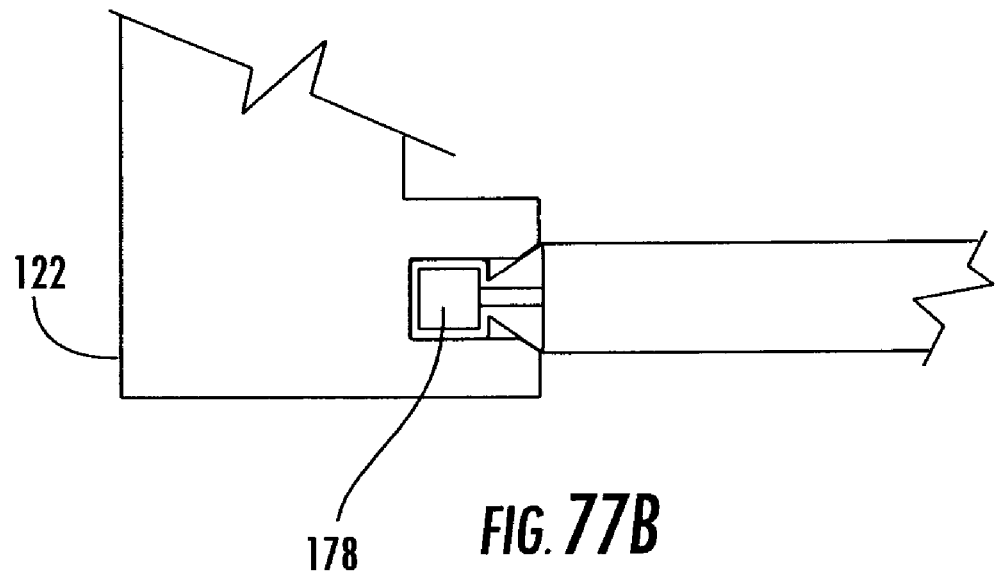
FIG. 77B is an end view of "external" engagement of a rectangular or square single surface platform rail with a self-catch auxiliary block.

FIGS. 77A and 77B illustrates a side view of an "External" engagement of a standard rectangular or square bed/stretcher/gurnie rail 178 by inwardly projecting self-locking catch tips 176 of auxiliary block 122.

Figure 78:
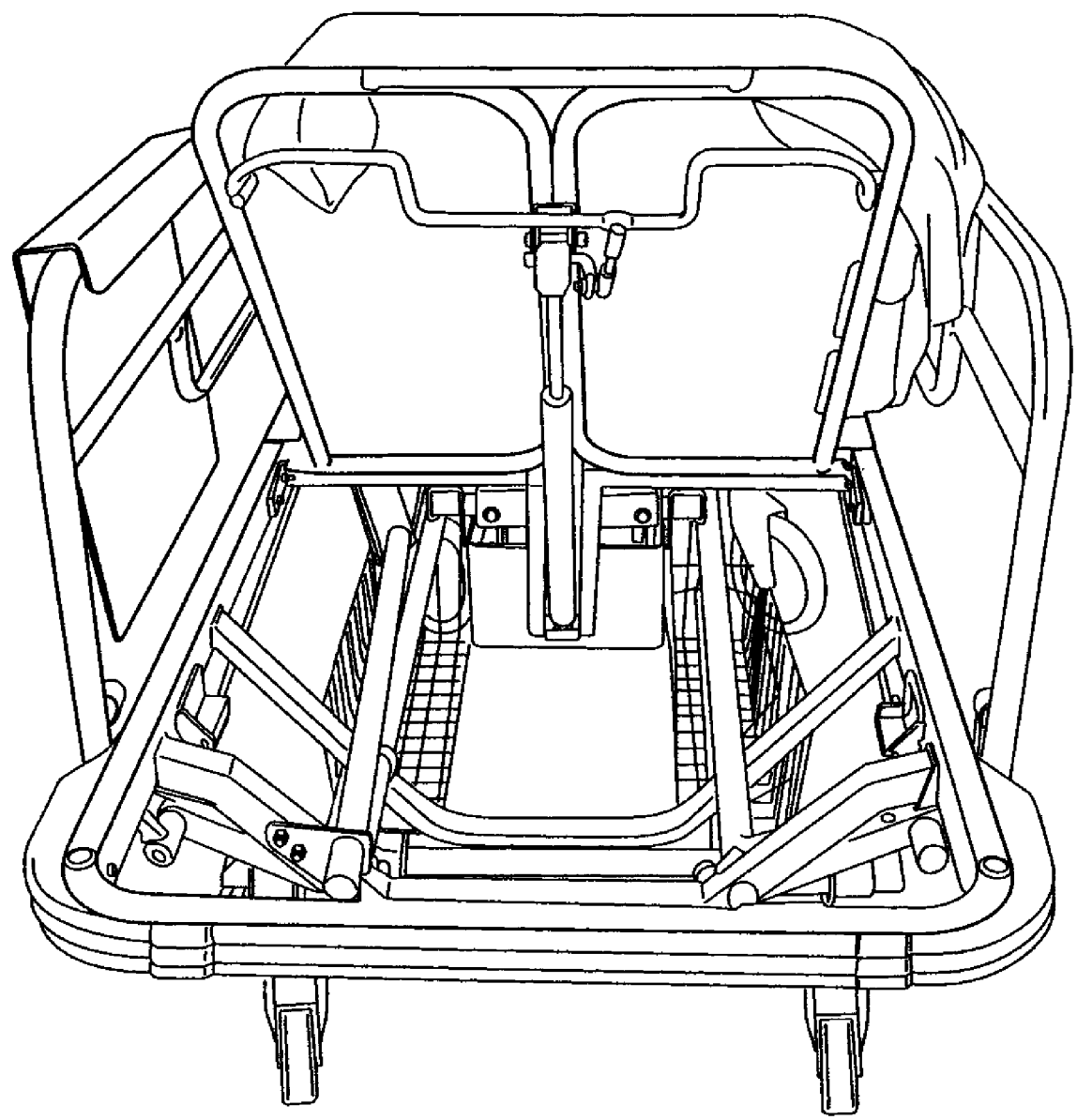
FIG. 78 illustrates a standard gurnie which could utilize the "external" engagement self-catch auxiliary block shown above in FIG. 77B.

FIG. 78 is a standard gurnie which could utilize the "External" engagement self-locking catch auxiliary design shown above in FIGS. 77A and 77B.

FIG. 79 is an isometric view of another alternative single surface platform rail 180 which provides for "External" engagement of the tips of auxiliary block.

FIG. 80 is an isometric view of the preferred "Internal" engagement of a self-locking catch auxiliary block 122 aligning to mate to an alternative standard rail design 180 with a slot or appropriately sized through hole.

FIG. 81 is an isometric view of the preferred "Internal" engagement of a self-locking catch auxiliary block 122 mated to an alternative standard rail design 180 with a slot or appropriately sized through hole.

Figure 82A:
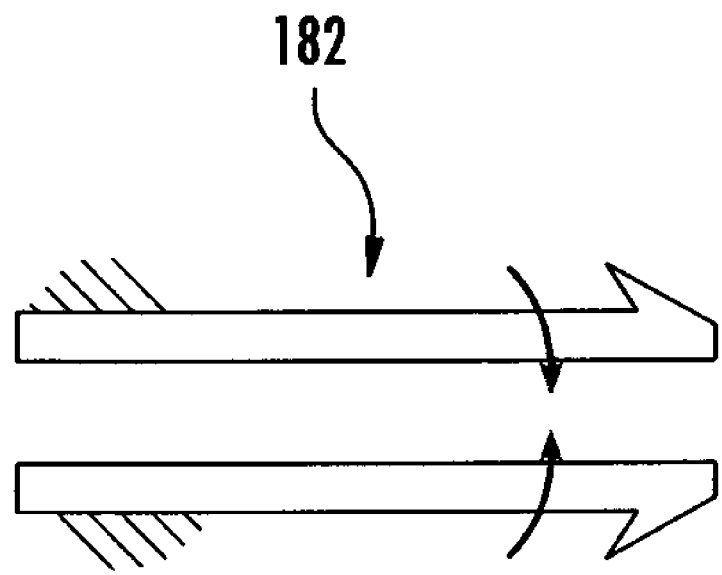
FIG. 82A illustrates a side view of alternative self-catch mechanism design.
Figure 82B:
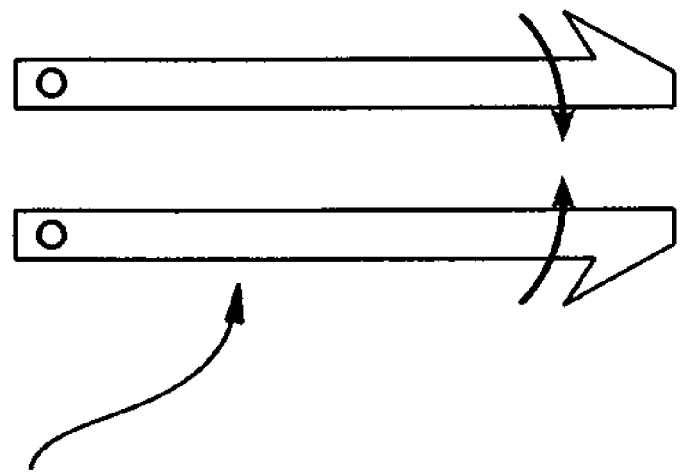
FIG. 82B illustrates a side view of another alternative self-catch mechanism design.

FIGS. 82A and 82B illustrate a side view of alternative types of mounts 182, 184 for self-locking catch designs. FIG. 82A depicts a "rigid" mount for the self-locking catches 182 in which the catch itself must flex/act as a living hinge. FIG. 82B depicts a pivot mount for the self-locking catches 182 in which the catch is spring-loaded.

Figure 83:
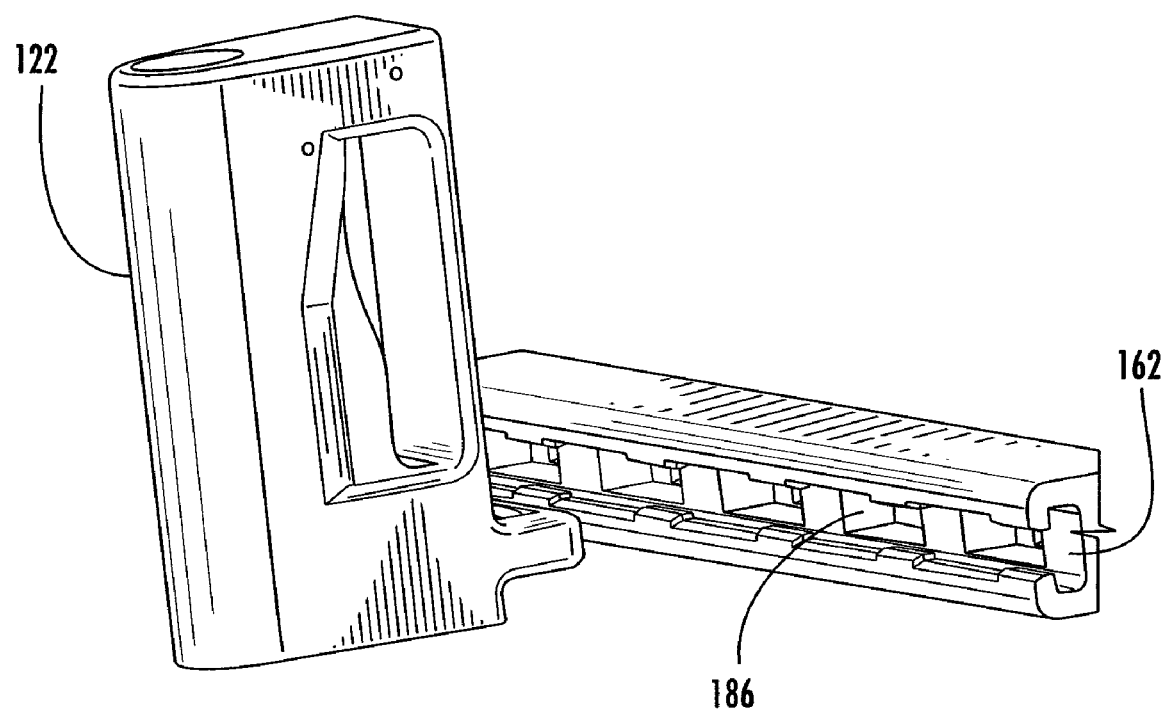
FIG. 83 is a perspective view of the auxiliary block assembly and a lateral lock version of the T-Slot.

FIG. 83 illustrates an isometric view of an auxiliary block assembly 122 mating to a lateral lock version of the T-Slot 162. This figure shows an auxiliary block with a longer "Nose" that fits into the apertures 186 (5 shown) at the back wall of the T-Slot. This mate improves the vertical load carrying ability of the auxiliary block and lateral lock.

Figure 84:
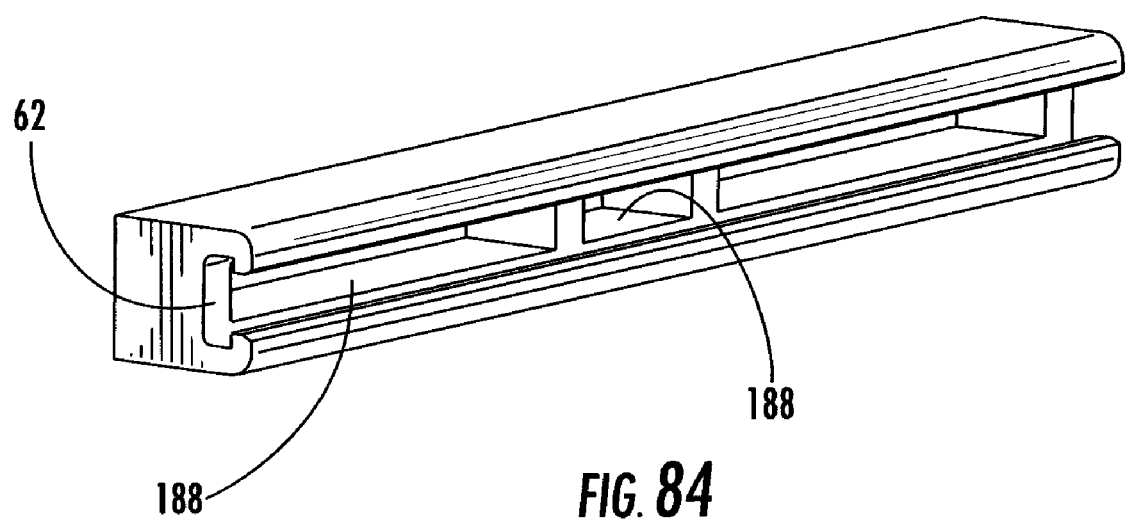
FIG. 84 is a perspective view of the a PS3 T-Slot with slots at the back wall of the T-Slot for the nose of the auxiliary block or the vertical support pins.

FIG. 84 is an isometric view of the standard PS3 T-Slot with slots 188 at the back wall of the T-slot for then nose of the auxiliary block. Note this is a separate piece of the standard PS3 T-Slot that can be placed anywhere (MRI, PS3 Frame, separate rack, a wall, etc. to accommodate PS3 wings, guardrails and auxiliaries when not assembled to the PS3 single surface platform. The same holds true for the lateral lock PS3 T-slot of FIG. 83.

Figure 85:
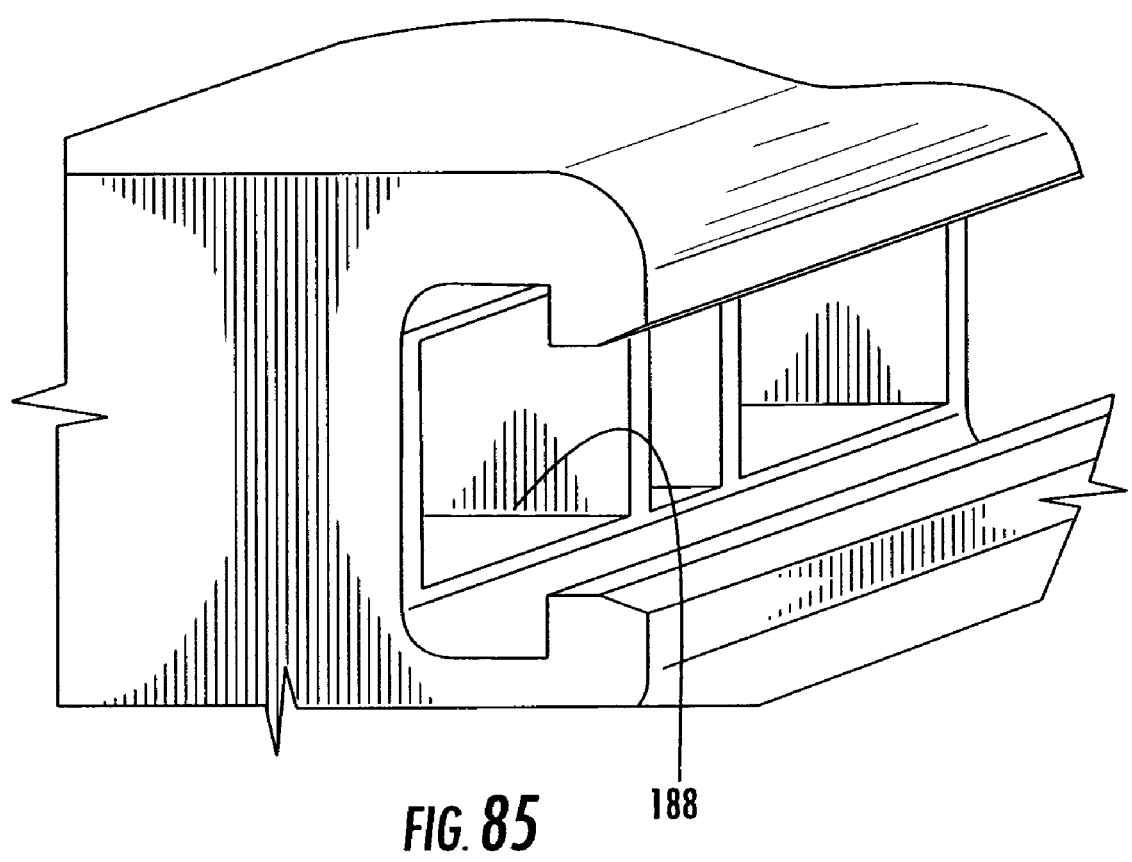
FIG. 85 is an enlarged view of FIG. 84.

FIG. 85 is an enlarged view of FIG. 84 illustrating a taper on the leading edge of the T-slots. This taper assists with the self-alignment of an auxiliary block or another wing section.

Figure 86:
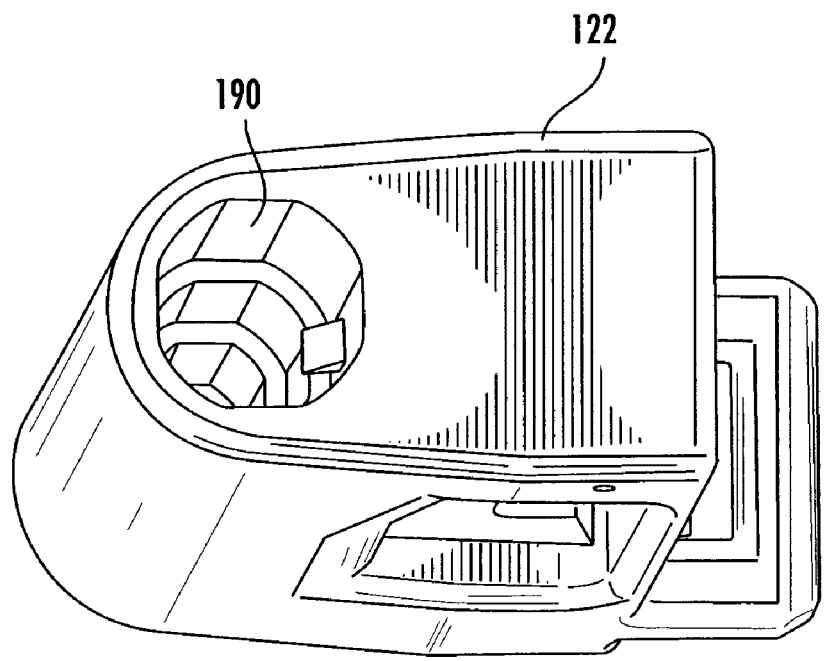
FIG. 86 is a top perspective view of the auxiliary block illustrating the four flats poke yoke.

FIG. 86 is a top isometric view of the auxiliary block 122 showing in detail the four flats-90 degrees apart configuration of the PokeYoke 190. This configuration allows four orientations of the pole and is easier from a manufacturing standpoint. Note, this also shows the auxiliary pole lock 136.

Figure 87:
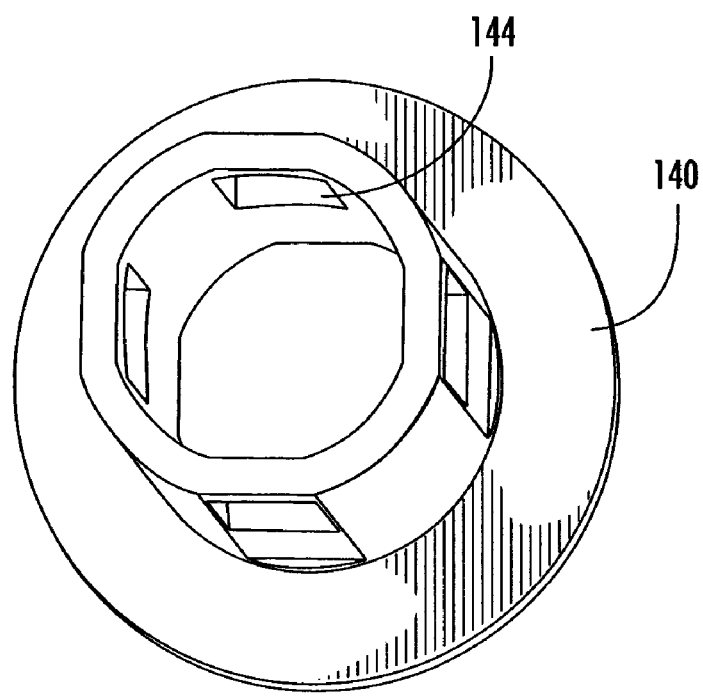
FIG. 87 is a bottom perspective view of the auxiliary lock ring with the four flats poke yoke and with corresponding slots for the auxiliary pole lock.

FIG. 87 is a bottom isometric view of the auxiliary lock ring 140 with the four flats-90 degrees apart PokeYoke with corresponding slots 144 for the auxiliary pole lock. The Poke Yoke insures 140 mates to 122 properly always resulting in a self-lock mate with pole lock 136.

Figure 88:
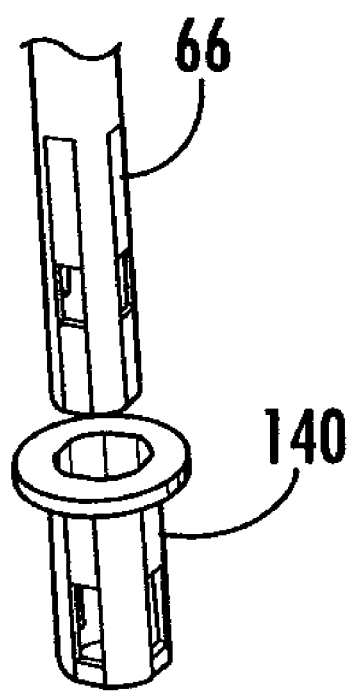
FIG. 88 is an exploded view of the auxiliary block, auxiliary lock ring and the bottom of the auxiliary pole.
Figure 88:
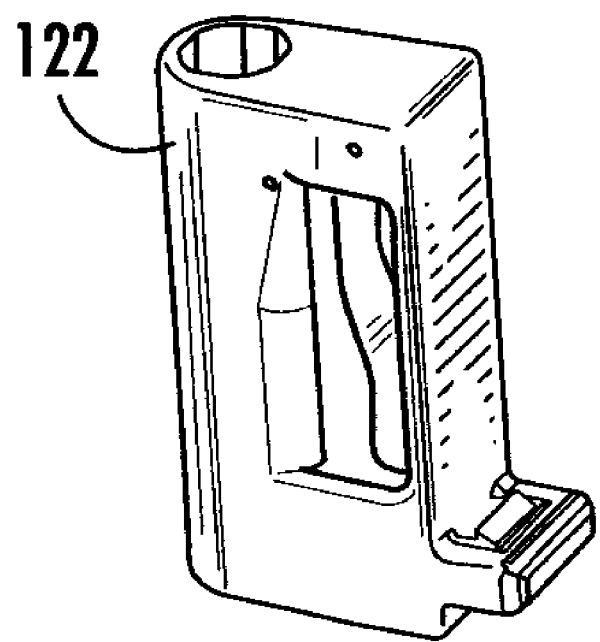

FIG. 88 is an isometric exploded view illustrating the relationship of the auxiliary block 122, the auxiliary lock ring 140 and the bottom of the auxiliary pole 66.

Figure 89:
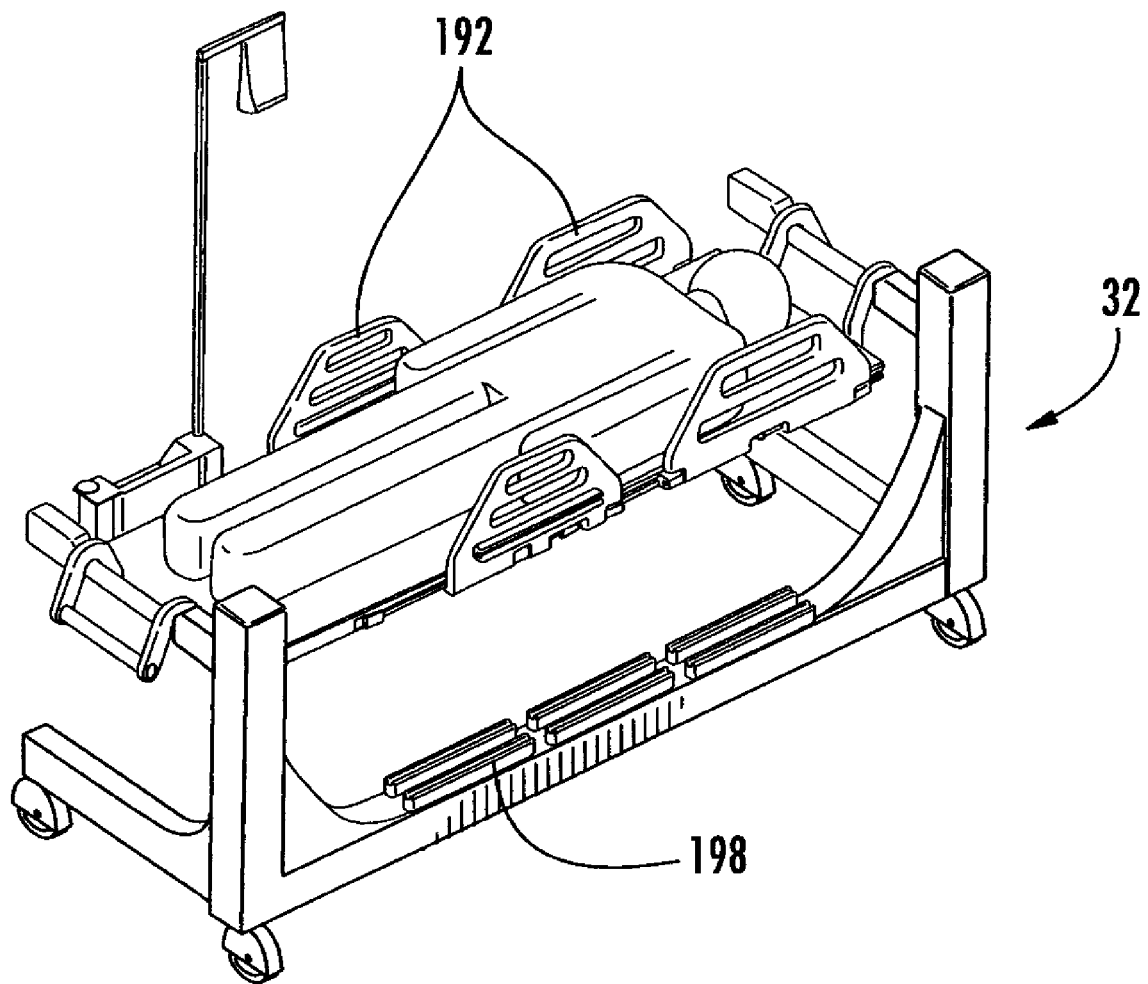
FIG. 89 is a perspective view of the PS3 system including guardrails, which mount into the PS3 T-Slot with the same Self-Catch Mechanism as the Auxiliary Blocks and Wings.

FIG. 89 is an isometric view of the PS3 single surface platform including the addition of guardrails 192, which mount into the PS3 T-slot with the same self-locking catch mechanism as the auxiliary blocks and wings. The guardrails further include a PS3 auxiliary T-slot mounted thereon, and further illustrate the use inclusion of auxiliary T-slots 198 mounted to the frame 32.

Figure 90:
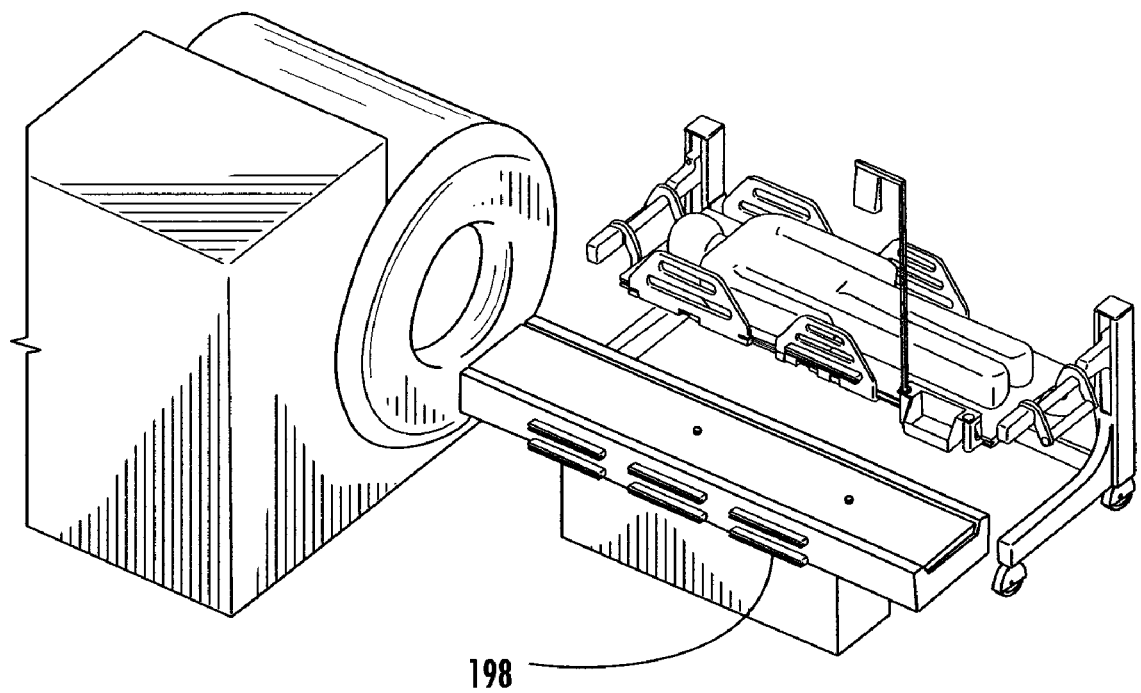
FIG. 90 is a perspective view of PS3 system approaching an MRI in which auxiliary T-Slots are placed on the side of the MRI bed platform to attach the PS3 wings and guardrails thereby providing additional patient safety.

FIG. 90 represents an isometric view of the above illustrated PS3 single surface platform approaching an MRI device in which auxiliary T-slots 198 are placed on the side of the MRI bed platform to attach the PS3 wings and guardrails. The guardrails would be placed in the upper T-slots on the MRI platform to provide additional patient safety. These auxiliary T-slots could be mounted horizontally as shown or vertically.

Figure 91:
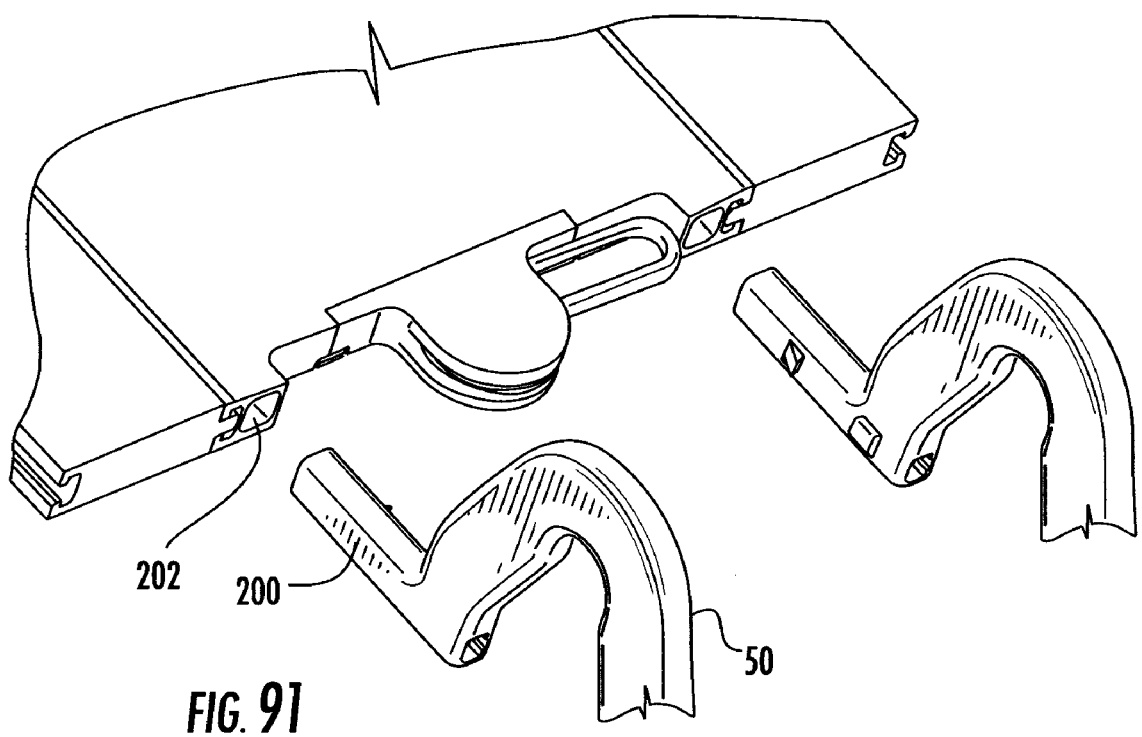
FIG. 91 is a perspective view of the PS3 single surface platform to frame interface hooks provided with the same basic self-catch mechanism as the auxiliary block and wings

FIG. 91 is an isometric view of the PS3 single surface to frame interface hooks 50 adapted for inclusion of the same basic self-lock catch mechanism as the auxiliary block and wings (see FIGS. 92 and 93) by the addition of extensions 200. They are released from the PS3 single surface platform with a push button as shown attached to the extension. The push buttons are preferably positioned on the inside of the single surface to frame interface extensions to help prevent accidental release. They could also be placed on both inside and outside or just outside.

Figure 92:
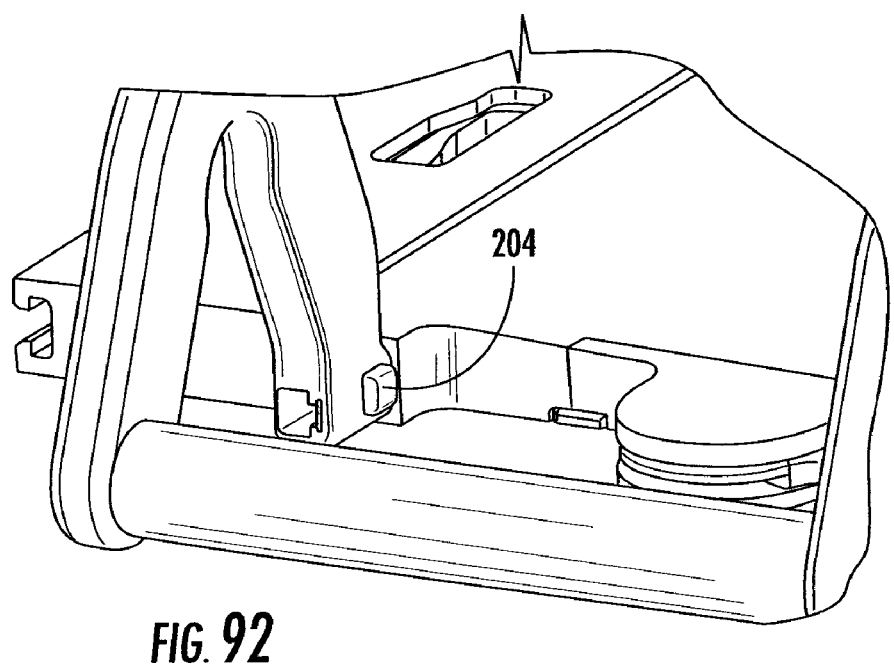
FIG. 92 is a perspective view of the single surface platform to frame interface hooks installed on the PS3 Single surface platform.

FIG. 92 is a zoomed isometric view of the single surface to frame interface hooks provided with the self-catch mechanism release pushbutton 204 and inserted into the PS3 single surface platform.

Figure 93:
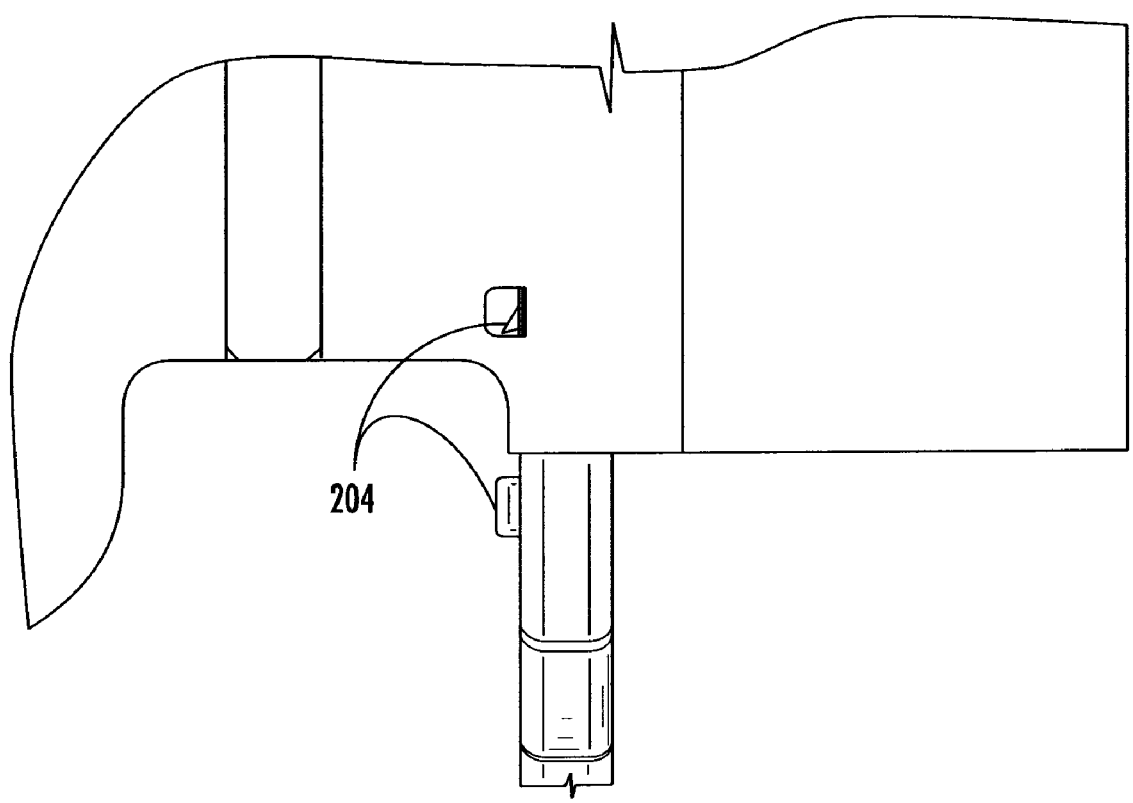
FIG. 93 is a bottom view of the PS3 single surface platform with a recess for the single surface platform to frame interface hooks self-catch mechanism to provide a secure mating of the single surface platform to frame interface hooks to the single surface platform.

FIG. 93 is a bottom view of the PS3 single surface platform with a recess for the single surface to frame interface hook self-catch mechanism 204 to provide a secure mate of the single surface to frame interface hooks to the single surface platform.

Figure 94:
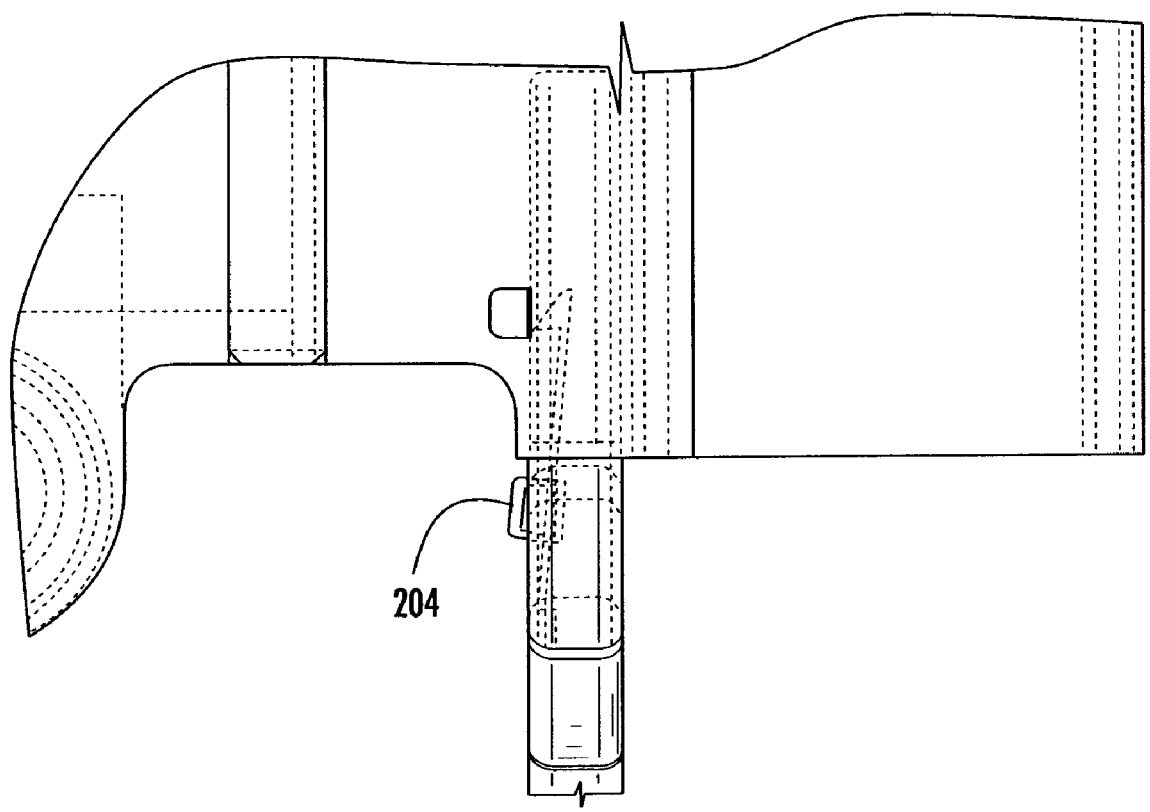
FIG. 94 is a bottom view showing the retraction of the single surface platform to frame interface hooks self-catch mechanism to allow removal of the single surface platform to frame interface hooks.

FIG. 94 is a bottom view similar to FIG. 93 showing the retraction of the single surface to frame interface hooks self-catch mechanism 204 to allow removal of the single surface to frame interface hooks when the buttons are pushed in this manner.

Figure 95:
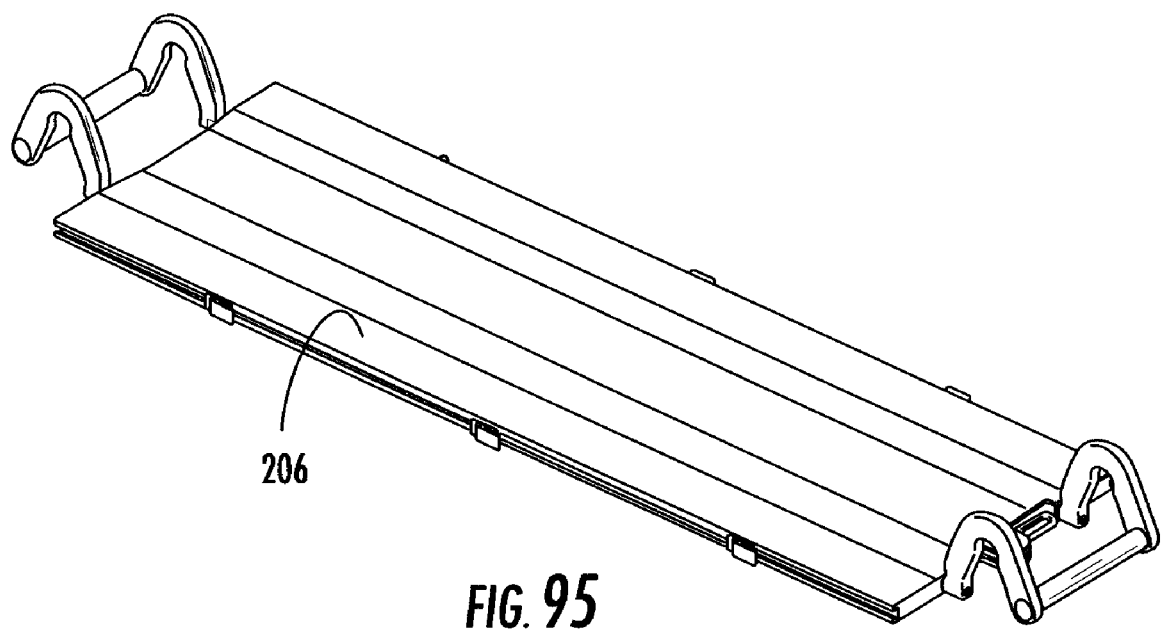
FIG. 95 is a perspective view of the PS3 single surface platform with a deflated air mattress on top covering the entire single surface platform surface.

FIG. 95 is an isometric view of the PS3 single surface platform illustrating an air mattress 206 in a deflated condition on top, and covering the entire surface.

Figure 96:
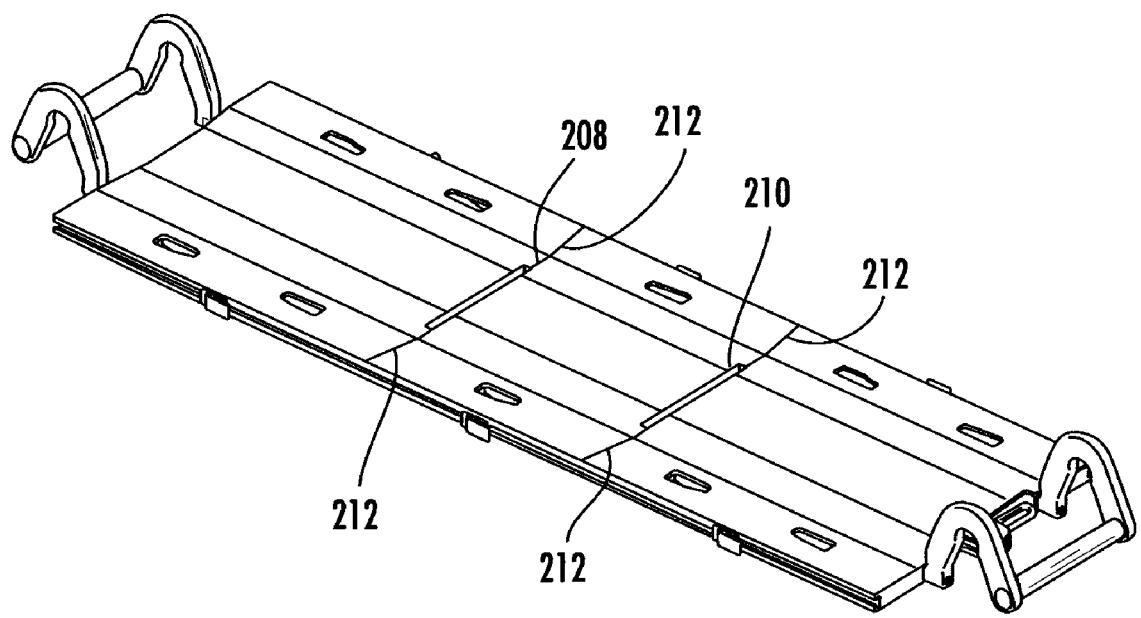
FIG. 96 is a perspective view of the PS3 Single surface platform with wings attached and without the deflated air mattress.

FIG. 96 illustrates an isometric view of the PS3 single surface platform with wings and without the deflated air mattress on top. Hinge 208 is provides between the backrest portion and the mid portion of the PS3 single surface. Hinges 212 are provided between the corresponding wings attached to these surfaces. Hinge 210 is provided between the mid portion and the knee gatch of the single surface. Hinges 212 are provided between the corresponding wings attached to these surfaces. Note, there could be an innumerable number of wing width options depending on the specific application.

Figure 97:
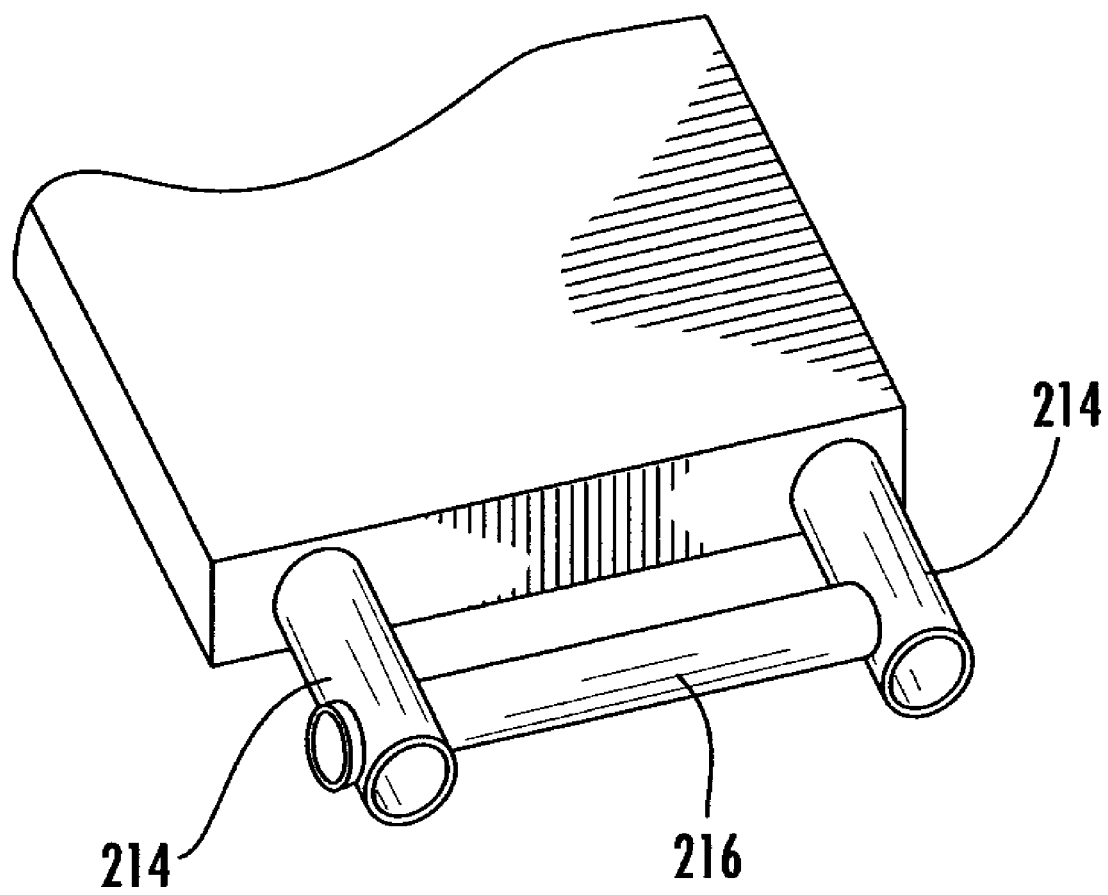
FIG. 97 is a perspective view of another embodiment of the single surface platform to frame interface hooks wherein the hooks are straight and a crossbar connects the interface hooks.

FIG. 97 is a perspective view of another embodiment of the single surface platform to frame interface wherein the interface members 214 are straight and project outwardly from the single surface platform. A crossbar 216 connects these interface members (these could not be used to interface with the frame, but would function strictly as handles) and permits the interface member to be utilized as a handle or attachment member to the frame.

Figure 98:
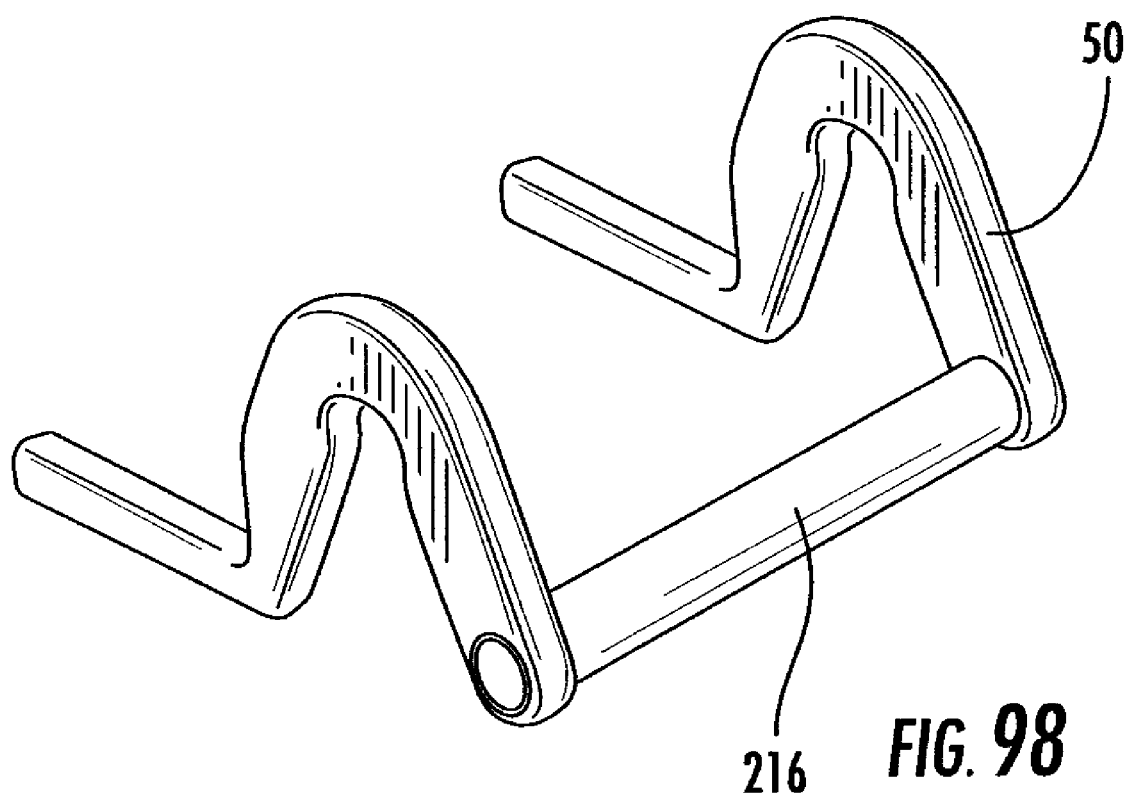
FIG. 98 is a perspective view of the hooked shaped single surface platform to frame interface hooks provided with a crossbar.

FIG. 98 is a perspective view of the hook shaped single surface platform to frame interface hooks 50 provided with a crossbar 216.

Figure 99:
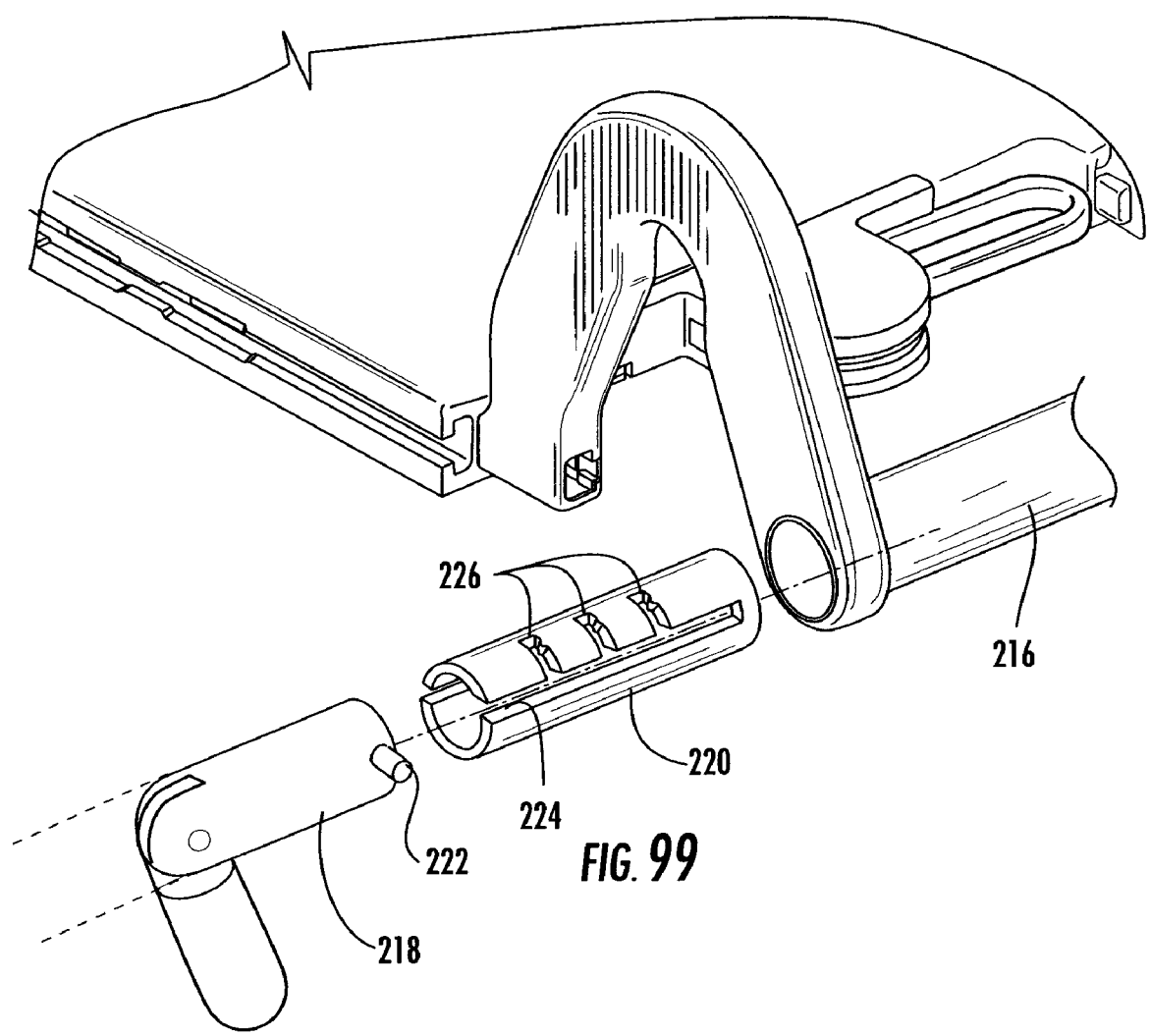
FIG. 99 is an exploded view of a handle assembly and sleeve which are insertable into the crossbar to provide carrying handles.

FIG. 99 is an exploded view of a handle assembly 218 and sleeve 220 which are insertable into the crossbar 216 to provide carrying handles. The sleeve 220 is provided with a longitudinal slot 224 and vertical slots 226 for the reception of pins 222 of handle assembly 218. This permits the distance that the handle assembly protrudes from the crossbar 216 to be adjusted. The hinge joint in the handle allows for angular orientation adjustment for the user's comfort as well as the ability to straighten and store away in the crossbar 216. Note optional detent features (not shown herein) may be positioned near the top of the slots 226 to "snap/lock" the pin 222 into when rotated into position.

Figures 100, 101:
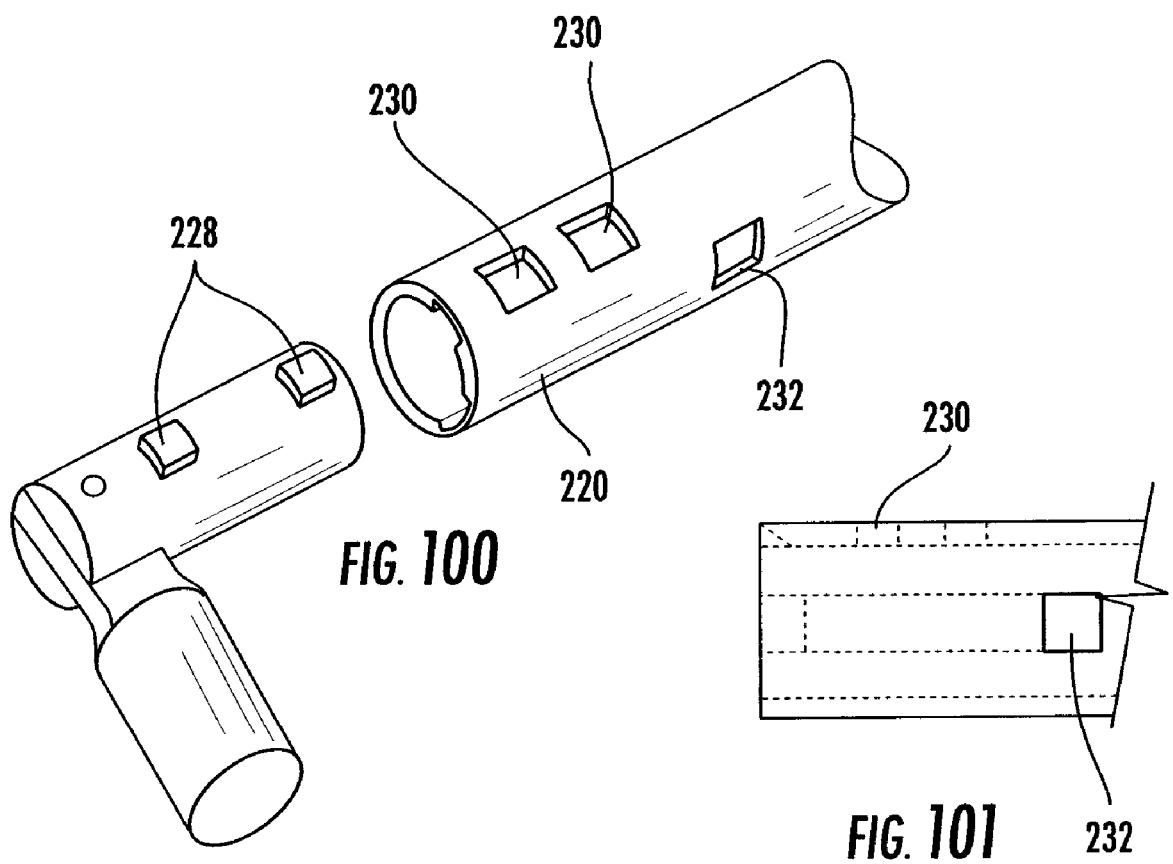
FIG. 100 is an alternative mechanism for attaching the handle assembly to the sleeve.
FIG. 101 is a side view of the sleeve illustrated in FIG. 100.

FIG. 100 is an alternative mechanism for attaching the handle assembly to the sleeve. Self catch mechanism 228 is mounted in the handle assembly. Apertures 230 and 232 are provided in sleeve 220. The tabs of the self catch mechanism 228 are engageable with the apertures 230 and 232 thereby enabling the distance that the handle assembly extends from the sleeve to be adjusted.

FIG. 101 is a side view of the sleeve 220 illustrated in FIG. 100.

Figure 102:
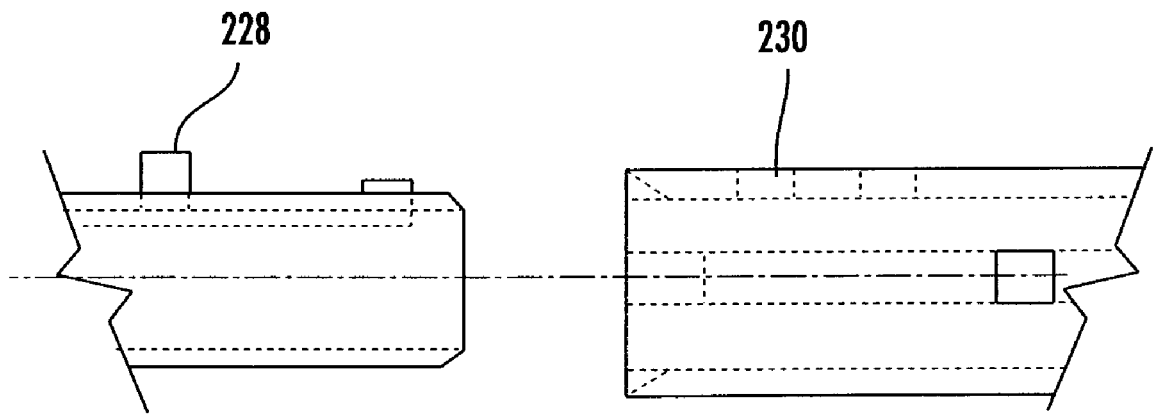
FIG. 102 is a side view of the handle assembly and sleeve illustrating the relationship of the latch and receiving holes.

FIG. 102 is a side view of the handle assembly 218 and sleeve 220 illustrating the relationship of the self catch mechanism 28 and apertures 230 in the sleeve.

Figure 103:
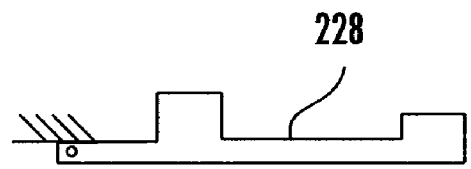
FIG. 103 is a side view of the latch assembly of FIG. 102.

FIG. 103 is a side view of the self catch mechanism of FIG. 102 either rigidly fixed and required to flex or a pivot and spring-loaded.

Figures 104, 105:
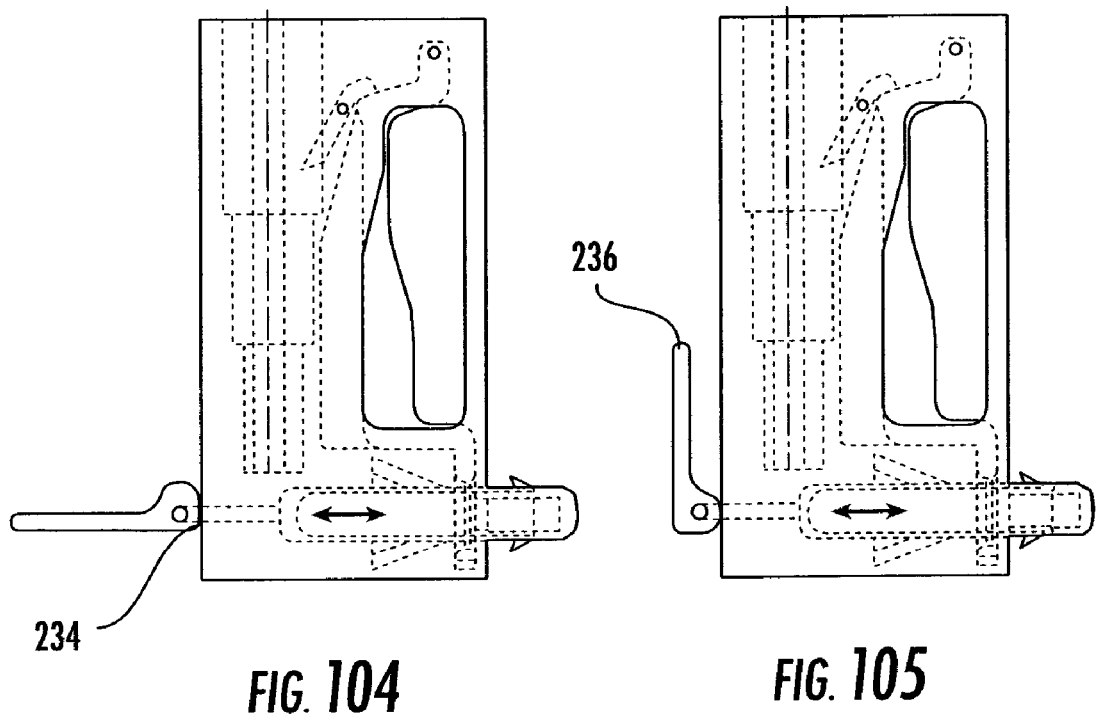
FIG. 104 is a side view of an alternative embodiment of the auxiliary block provided with a tension lock.
FIG. 105 is a view similar to FIG. 104 with the tension lock in its locked position.

FIG. 104 is a side view of an alternative embodiment of an auxiliary block provided with a tension lock 234 in the unlocked position.

FIG. 105 is a view similar to FIG. 104 with the eccentric tension lock in its locked position. The tension lock lever is moved upwardly to its vertical position. This action moves the tension lock to the left whereby the self-locking catch is also moved to the left. This provides an additional force to secure the auxiliary block to the T-slot of the wing or single surface platform and does not allow one to release the auxiliary block from the wing or single surface via the release handle when tension lock lever 236 is locked.

Figure 106:
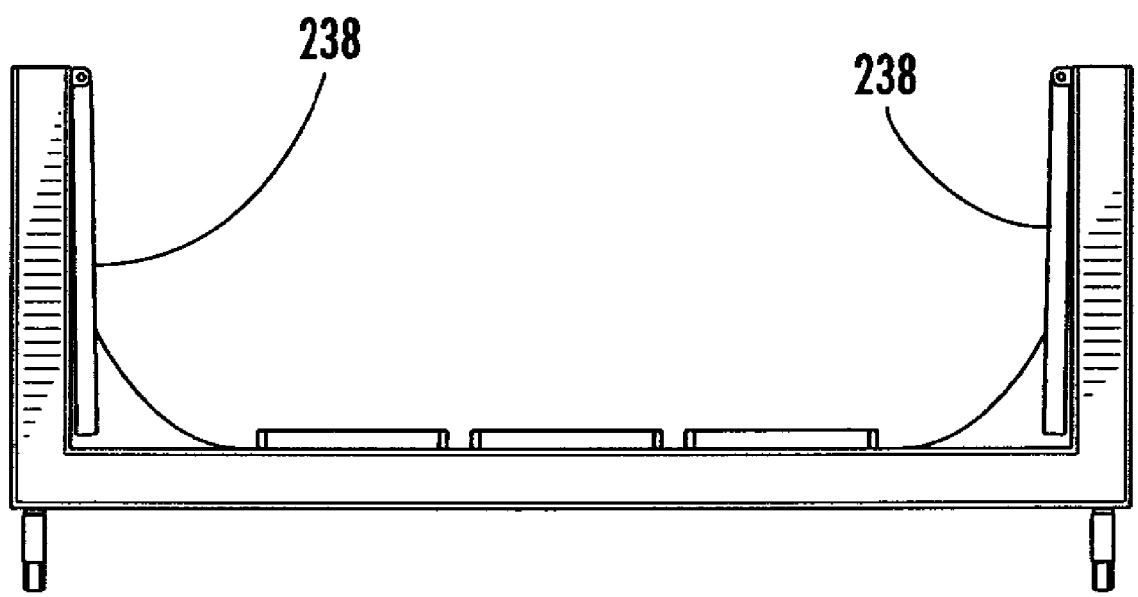
FIG. 106 is a side view of the PS3 assembly provided with push/pull folding handles, which are used to move and position the PS3 assembly, in their inoperative position.

FIG. 106 is a side view of the PS3 assembly provided with push/pull folding handles 238, which are used to move and position the PS3 assembly, in their inoperative position.

Figure 107:
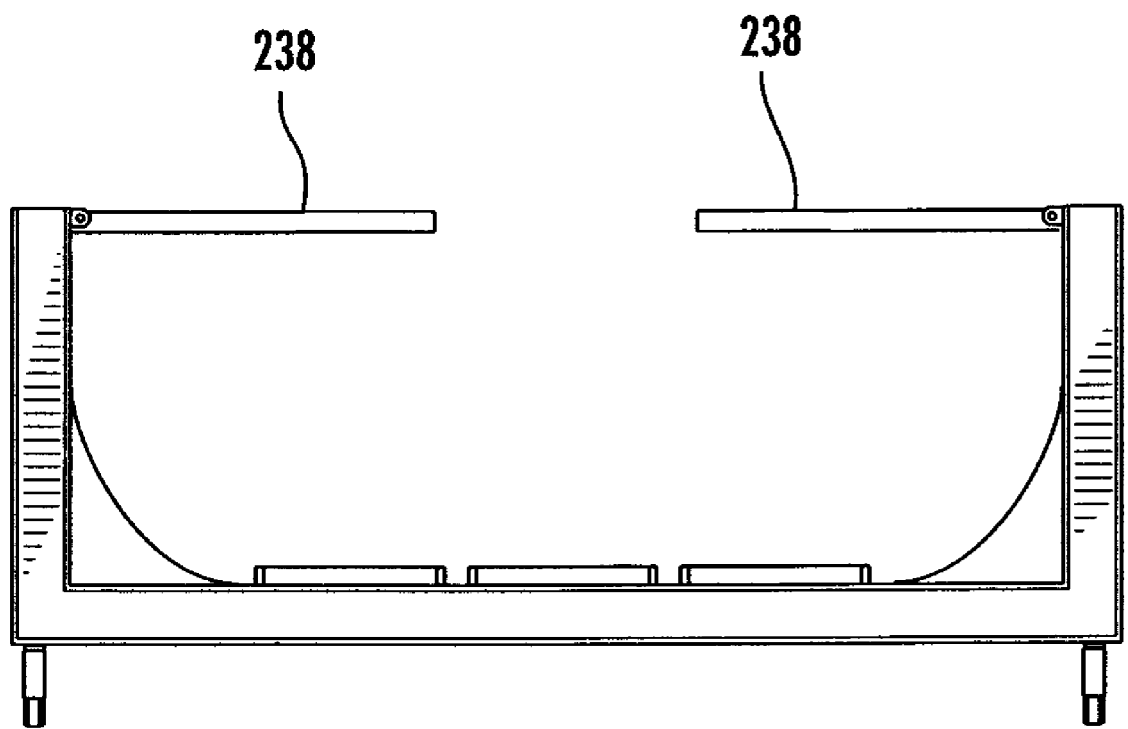
FIG. 107 is a side view of the PS3 system of FIG. 106 with the push/pull handles in their operative position.

FIG. 107 is a side view of the PS3 system of FIG. 106 with the push/pull handles 238 in their operative position.

Figure 108:
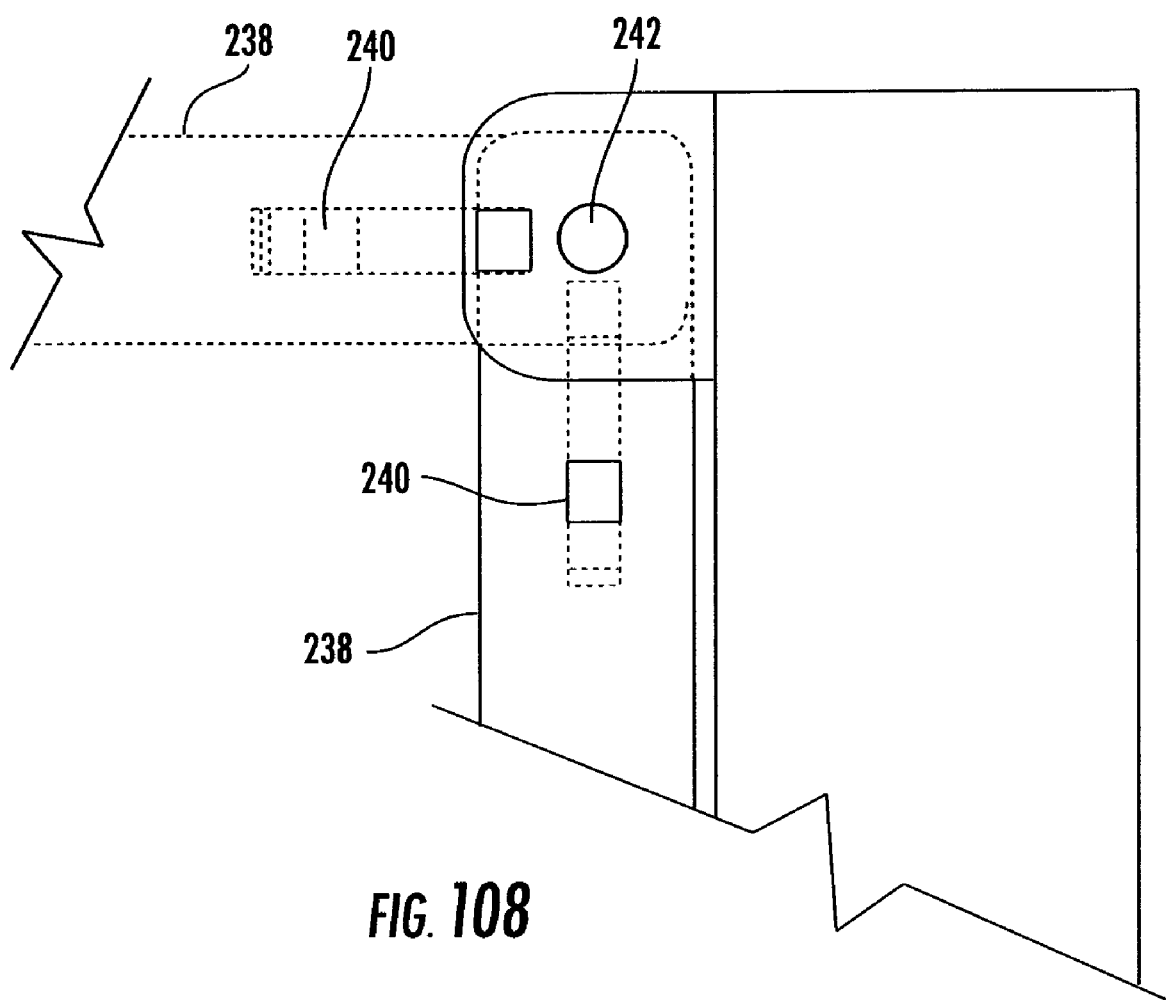
FIG. 108 is a partial view of the push/pull handles and PS3 frame illustrating the self-locking latch which holds the handles in their operative position.

FIG. 108 is a partial view of the push/pull handles and PS3 frame illustrating the hinge pin 242 about which the handles pivot. Also shown is the self-locking latch 240 which holds the handles in their operative or inoperative positions.

Figure 109:
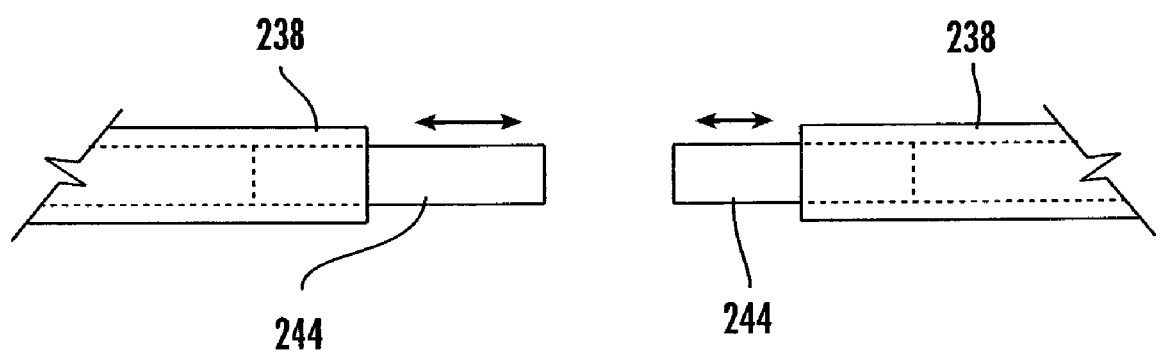
FIG. 109 is a partial side view of the ends of the push/pull handles provided with telescoping extensions.

FIG. 109 is a partial side view of the ends of the push/pull handles provided with telescoping extensions 244.

FIG. 110 is a top plane view of the PS3 single surface platform incorporating an upper body portion hinged to a mid portion which is hinged to a knee gatch portion. Separate wing sections 24, 30 and 28 are attached to the respective portions of the single surface platform. Hinges are illustrated on the single surface platform and the lower wing sections.

Figure 111:
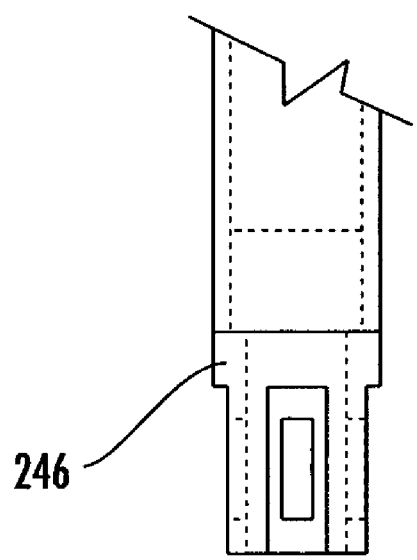
FIG. 111 illustrates an internally mounted adaptor plug for an auxiliary pole.

FIG. 111 illustrates an internally mounted adaptor plug 246 for an auxiliary pole.

Figure 112:
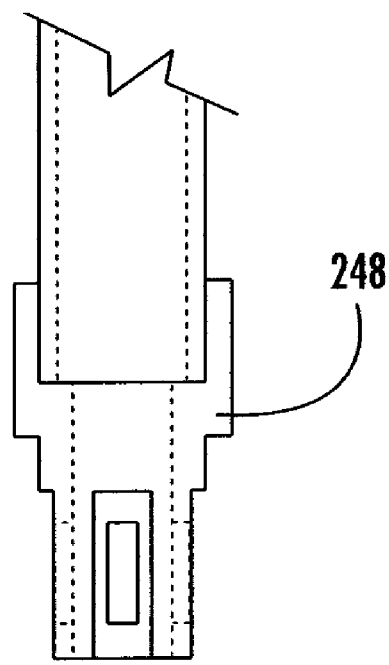
FIG. 112 illustrates an externally mounted adaptor plug for an auxiliary pole.

FIG. 112 illustrates an externally mounted adaptor plug 248 for an auxiliary pole.

Figure 113:
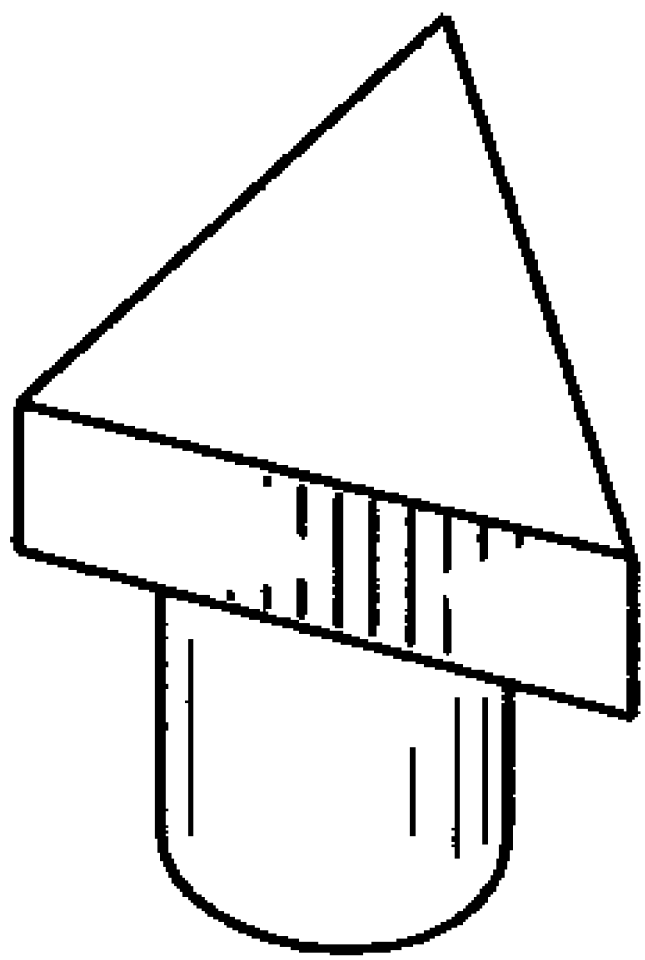
FIG. 113 illustrates an alternative, triangular shaped T-pin.

FIG. 113 illustrates an alternative, triangular shaped T-pin.

Figure 114:
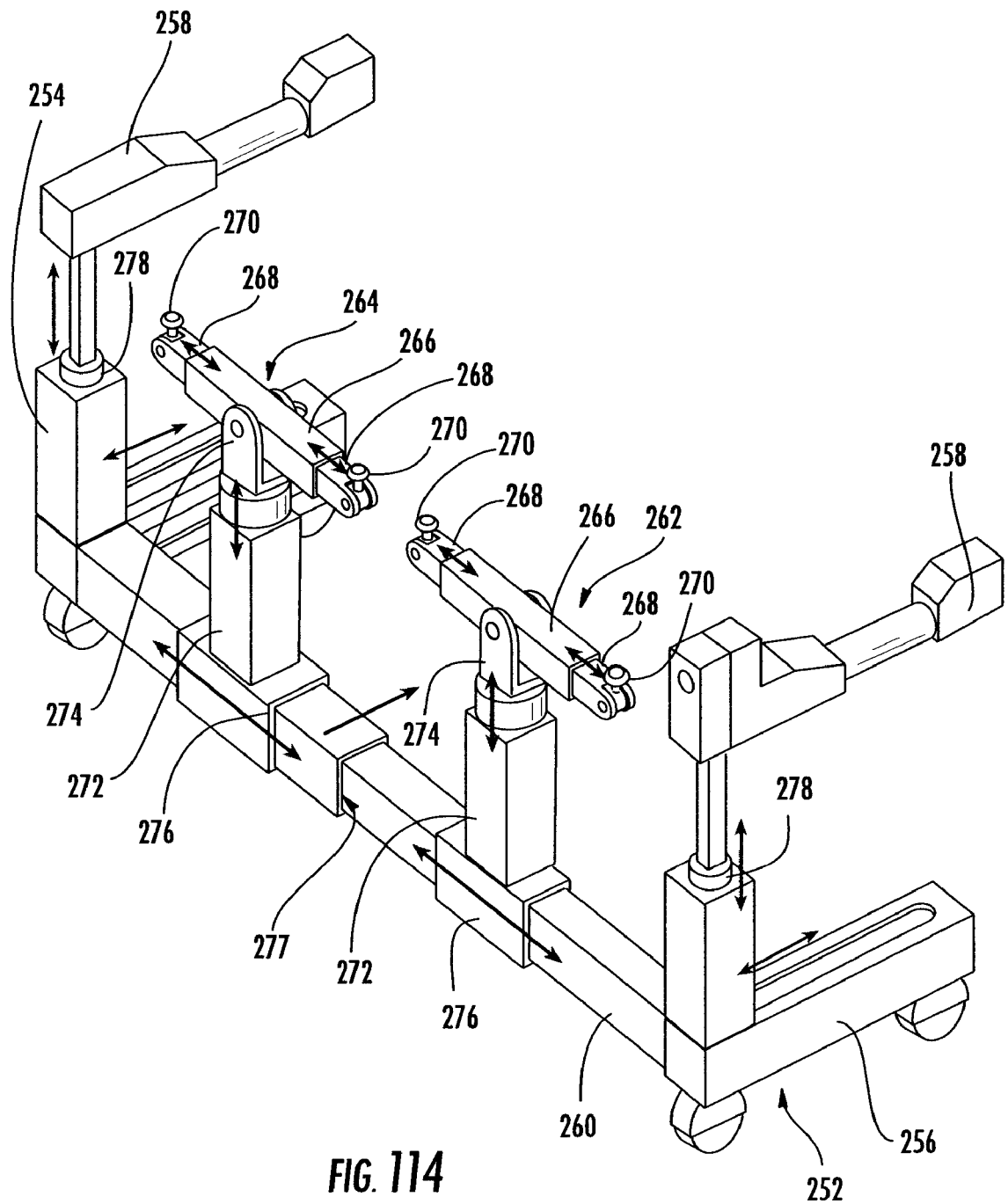
FIG. 114 illustrates and alternative frame useful with a single surface platform in an unlocked, articulated state.
Figure 115:
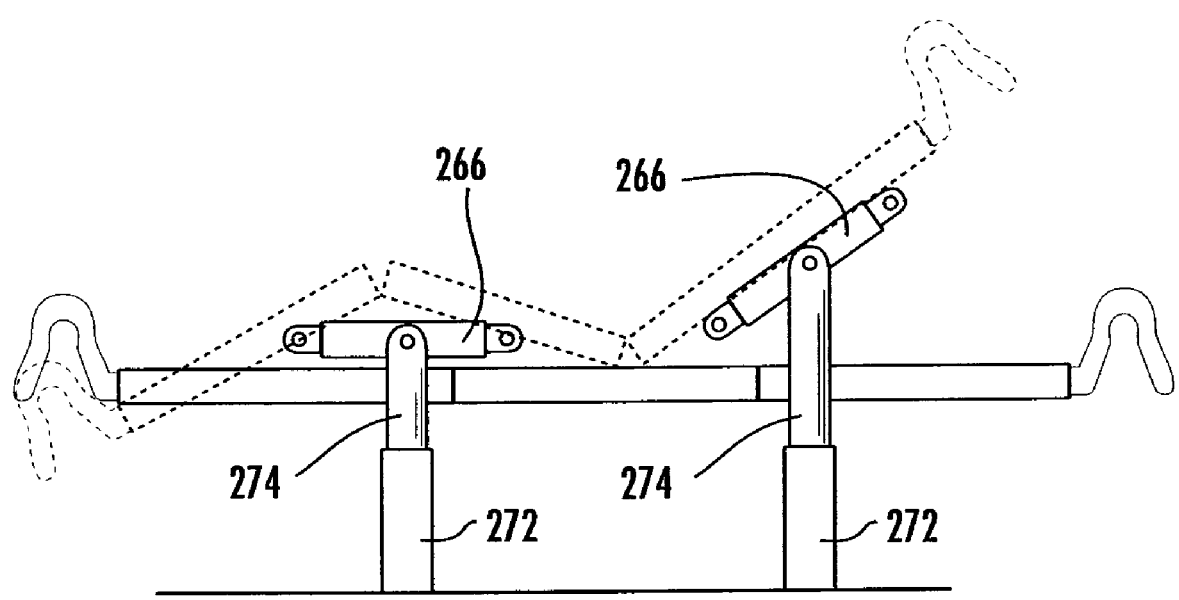
FIG. 115 illustrates the single surface platform supported by the alternative frame of FIG. 114

FIG. 114 illustrates transfer/transport frame 252 which is an alternative embodiment of transfer/transport frame 32. The new additional frame elements shown in FIG. 114, which are described in the following, enable the following additional functions: in PS3 frame articulation of the frameless single surface backrest and kneegatch joints, complete reversal of the cantilever with or without the PS3 single surface in place, equal access to either transverse side of the frame during all situations except surface transfer and additional single surface support to minimize binding/friction during docking of the articulation inter-lock module 152 while the frameless single surface is supported in the PS3 frame. Articulation of the backrest incline and knee gatch within the PS3 frame as well as the ability to provide equal access to both sides of the single surface while in the PS3 frame, except during surface transfer, eliminates the need for a separate supporting surface and elimination of the need for storage of the PS3 frame during patient convalescence or otherwise. Frame 252 includes frame lower legs 256 positioned at each end of frame 252. A collapsible/extendable lower cross member 260, extends between and connects the frame lower legs 256. Cross member 260 is collabsible/extendable to compensate for large horizontal distance changes required between support columns 254 during in frame articulation of the backrest and knee gatch joints as shown in FIG. 115, while maintaining interface between arms 258 and single surface to frame interface member 50. Maintaining the arm 258 to single surface to frame interface member 50 during articulation of these joints adds support/stability and reduces the function required from the inner support assemblies 262 and 264. For example, member 266 in FIG. 115 would not require engagement/actuation of the backrest section for backrest articulation and/or Trendelenburg if the main single surface to frame interface members 258 are engaged as described. One of the frame interface members 258 still utilize the pivot 40 to accommodate small horizontal distance changes for pure Trendelenburg and reverse Trendelenburg. The lower cross member 260 is in telescoping engagement with said legs 256, as well as traversing said legs in a lateral direction, wherein said cross member 260 is movable from one side of said frame 256 to another in which the wheels' 46 rotation are locked to facilitate this traverse of the cross member 260. Simply the lateral movement of the cross member 260 to a mid position lengthwise of legs 256 allows equal access to either side of the single surface while in the PS3 frame in all situations other than those transfers requiring the cantilever function. The cantilever columns 254 are each telescopingly engaged with said legs 256, as well as being rotatable and translatable in a manner effective to rotate the support members 258 180° in response to translation of said columns from a first side of said frame 252 to the other side thereof. Rotation of said support members 258 permits the single surface platform to remain aligned with the lower legs 256, thereby preventing the frame from becoming unstable and reversing the cantilever in concert with the traverse of cross member 260. This allows correct orientation of the patient to transfer surface within the PS3 frame dependent on which side of a surface for transfer has clear access without having to disengage and engage the single surface and patient on another surface to re-orient. The bottom large square column 254 which interfaces 256 remain fixed in orientation about its vertical axis and cylinder 278 allows a rotational degree of freedom and is mated to pinion 279 which repeatability automates rotation during translation and proper final orientation of arms 258 depending on the end positioned on the leg 256. Reversing the cantilever with the single surface and patient in place requires the usage of the inner support column assemblies 262 and 264 in which the single surface platform is raised to a position above the tops of assemblies 262 and 264. Further included are telescoping, rotatable and longitudinally adjustable supports 262, 264 which are engageable with, and support said single surface support platform. Each of said adjustable supports 262, 264 are provided with a mating means assembly for selectively enabling reversible engagement with and adjustment of the single surface support platform, the mating means assembly being comprised of pivoting support member 266, adjustable extension 268 and mating means 270. A pivoting support member 266 is mounted above each adjustable support 262, 264, each said supporting member 266 being vertically adjustable and rotatable. Each said supporting member 266 further including adjustable extensions 268 which are provided with mating means, e.g. T-pins, 270 for enabling reversible engagement with the single surface support platform, in a variety of configurations. For example, when rotated 90 degrees, the T-pins 270 will provide mating engagement with coupling elements 285,286, as illustrated in FIG. 69. Support columns 274 enable vertical adjustment and rotation of said support members 266 with respect to support columns 272. Columns 272 slidably engage lower cross member 260 via column mounting elements 276. The next step in cantilever reversal involves the cross member 260 and assemblies 262 and 264 which are positioned in a mid leg 256 position so the assemblies 262 and 264 are positioned below the lateral center of the single surface. Subsequently, the inner support assemblies 262 and 264, which are slidably engaged on cross member 260, are positioned longitudinally below the self-aligning keyhole recesses 285 and 286 in FIG. 69. In the process of this longitudinal positioning of inner support assemblies 262 and 264, they automatically rotate 90 degrees via the same basic method as described for translation and rotation of arms 258 except modified for 90 degree rotation instead of 180 degrees. Next, the arms 268 are retracted or extended to allow T-pins 270 to align with the large end of the keyholes 285 and 286. Then, the single surface is lowered onto the current vertically oriented and locked T-Pins 270, via the frame top single surface interface arms 258, which mate in the large end of the keyholes 285 and 286. Next, the arms 268 retract to securely mount and support the single surface by the assemblies 262 and 264. At this point, the articulation interlock module 152 could be easily removed or installed in the frameless single surface as described earlier. Finally, the assemblies 262 and 264 raise the single surface off of the single surface to frame interface arms 258 and allow the cantilever reversal of arms 258. Then the arm 258 and assemblies 262 and 264 engagement is reversed to return the single surface loading to arms 258 and allow the cantilever reversal completion via movement of the cross member 260 and its corresponding assemblies 262 and 264 to the end of the legs 256 in which the columns 254 now reside. Description of the PS3 frame 252 backrest and knee gatch articulation of the frameless single surface follows. Like the cantilever reversal process the first step for backrest and knee gatch articulation involves the single surface platform positioning above the tops of assemblies 262 and 264 via the arms 258. Once again cross member 260 and assemblies 262 and 264 are moved to a mid leg 256 position so the assemblies 262 and 264 are positioned below the lateral center of the single surface as well as the proper longitudinal position to mate one of the T-pins 270 sets on assembly 262 or 264 to the articulation interlock module keyholes 85 large end. The resultant assembly 262 or 264 to be engaged to the single surface is raised above the non-engaging assembly 262 or 264. The single surface is lowered onto the intended T-pins 270 via the frame to single surface arms 258 and the single surface articulation handle 76 is rotated accordingly to lock into T-pins 270 as described earlier and release the backrest and knee gatch joint articulation. This locking into the T-pins releases a separate inter-lock to allow the rotation of the crossbar 266 about its pivot on 274 as well as the T-Pins about their pivot on the telescoping arms 268. The telescoping arms 268 can now retract to cause knee gatch articulation as shown in FIG. 115 in which T-Pins 270 only can rotate about the pictured pivot away from their telescopic arms 268 to force proper articulation of the knee gatch due to a mechanical stop between the T-pin 270 mount and the telescopic arms 268. The frame to single surface arms 258 can remain engaged in the single surface to frame interface hooks 50 via proper automated and actuated vertical adjustment of the arms 258 and horizontal retraction of the telescopic cross member 260. Backrest incline and combinations of Trendelenburg and Reverse Trendelenburg are also feasible through coordinated vertical movement of arms 258 and engaged assembly 262 or 264.

FIG. 115 illustrates articulation of the single surface platform about the articulating joints, permitting movement of the backrest incline and knee gatch with respect to the midsection. Single surface to frame interface hooks remain attached to either end of said single surface platform whereby engagement with said frame supporting arm may be effected.

Figure 116:
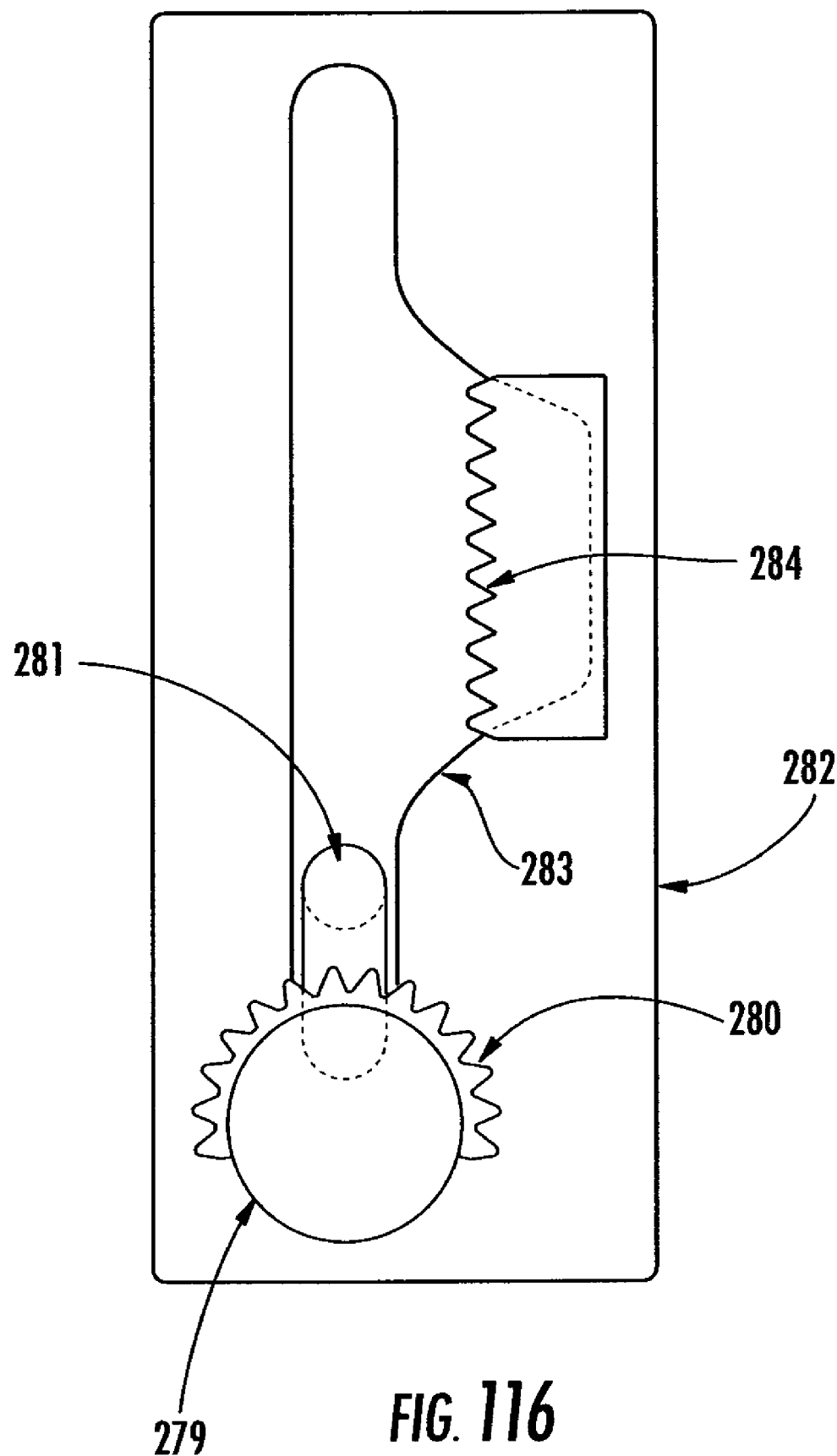
FIG. 116 illustrates a rack and pinion mechanism designed to insure coordinated movement of the frame supporting arm and frame cantilever column.

FIG. 116 is illustrative of a rack and pinion mechanism 282 designed to insure coordinated movement of the frame supporting arm 258 and frame cantilever column 254. As illustrated, upon initiation of lateral movement of the frame cantilever column 254, follower cam 281 begins to traverse across the width of frame lower leg 256, wherein gear 280 engages rack 284, providing rotation of frame supporting arm 258 in a coordinated fashion so as to effect a rotation of 180° upon completion of the traversal of said frame lower leg 256 by said frame cantilever column 254. Follower cam 281 engagement with cam profile 283 post rotation insures and maintains proper orientation of pinion 279 and resultant orientation of frame supporting arms 258. Pinion 279 is attached directly on the rotational center of the cylinder 278 or offset and connected via gears, belts and pulleys, etc. In an alternative embodiment pinion 279 could be connected to column 254 and eliminate the separate cylinder 278. This cooperation of elements provides reversibility of the orientation of the frame and cantilever arms while in place.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification. One skilled in the art will readily appreciate that the present invention is well adapted to carry out the objects and obtain the ends and advantages mentioned, as well as those inherent therein. Any devices, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A single surface system useful for continuous support, transfer and treatment of an individual throughout a plurality of medical environments and procedures comprising:
    a primary single surface having a longitudinal axis and a lateral axis;
    wherein said primary single surface includes an uppermost section and an adjacent section flexibly joined to at least one articulation means positioned therebetween and at least one locking means for reversibly enabling articulation about said articulation means;
    whereby articulation of said uppermost and adjacent sections of said primary single surface is permitted by positioning of said locking means from a first locked position to a second articulation enabling position;
    a single surface transport and transfer frame constructed and arranged for reversible engagement with said primary single surface; and
    at least one single surface-to-frame interface means for effecting reversible engagement of said primary single surface and said frame; each said single surface to frame interface means including (1) a single surface supporting member in adjustable engagement with said frame, and (2) supporting member engagement means constructed and arranged for self-aligning reversible engagement with said supporting member;
    whereby engagement of said single surface-to-frame interface means results in reproducible positioning of said primary single surface upon said frame with respect to both the longitudinal and lateral axes of said primary single surface.

2. The system of claim 1 wherein said primary single surface includes an uppermost section, a middle section, and a lowermost section, positioned adjacent to one another, each said section being flexibly joined to an articulation means positioned therebetween; and
    at least one locking means for reversibly enabling articulation about each said articulation means;
    whereby articulation of each said sections of said primary single surface is permitted by positioning of each said locking means from a first locked position to a second articulation enabling position.

3. The system of claim 1 wherein each said single surface supporting member is constructed and arranged for vertical adjustment with respedt to said frame;
    whereby horizontal positioning, vertical positioning and angular positioning of said single surface is enabled.

4. The system of claim 1 wherein each said single surface supporting member is constructed and arranged for rotational and translational adjustment with respect to said frame;
    whereby the position of each said single surface supporting member is reversible.

5. The system of claim 1 further including at least one removably attached extension element effective for incremental width adjustment of said primary single surface.

6. The system of claim 5, further including at least one inter-lock assembly constructed and arranged to preclude release of said extension element from said matable receiving surface.

7. The system of claim 1, wherein said primary single surface is constructed and arranged to include at least one matable receiving surface coextensive with a lateral edge thereof, which surface is adapted to receive at least one auxiliary component therein,
    whereby adjustable engagement of a plurality of auxiliary components is enabled.

8. The system of claim 7 wherein each said extension element is matable with said primary single surface or with another of said extension elements by way of said at least one matable receiving surface.

9. The system of claim 8, wherein each said extension element includes at least one matable receiving surface coextensive with a lateral edge thereof, which surface is adapted to receive at least one auxiliary component therein.

10. The system of claim 1 further including at least one auxiliary block assembly effective for reversible attachment of auxiliary components to said system, including a first means for releasable engagement with a matable receiving surface and a second means for releasable engagement with an auxiliary pole or an auxiliary locking ring.

11. The auxiliary block of claim 10 wherein said first means for releasable engagement includes at least one release mechanism coupled to a selflock catch; said self-lock catch having at least one locking tab which provide positive locking engagement when inserted within said matable receiving surface, and is deflected by operation of said release mechanism to enable retraction from said matable receiving surface.

12. The auxiliary block of claim 10 wherein said second means for releasable engagement include a stepped holed design to accommodate multiple pole/interface sizes.

13. The auxiliary block of claim 10 wherein said second means for releasable engagement includes an auxiliary pole lock.

14. The auxiliary block assembly of claim 13, wherein said first means for releasable engagement with a matable receiving surface and said second means for releasable engagement with an auxiliary pole further include a locking element incorporating a twostage quick release feature;
    wherein said twostage quick release feature is constructed and arranged to releasably engage said auxiliary pole lock when moved to a first release position, and is constructed and arranged to releasably engage said matable receiving surface when further moved to a second release position.

15. The auxiliary block assembly of claim 10, further including at least one inter-lock assembly constructed and arranged to preclude release of said auxiliary block assembly from said statable receiving surface.

16. The auxiliary block assembly of claim 14, further including at least one interlock assembly constructed and arranged to preclude operation of said twostage quick release feature, whereby inadvertent release of said auxiliary block assembly from said auxiliary pole or said matable.

17. The single surface system of claim 1, further including an articulation inter-lock module adapted for reversible engagement with said single surface;
   said articulation module including articulation inter-lock blocks incorporating therein coupling means adapted for reversible engagement with corresponding mating means affixed to a mating surface;
   said articulation inter-lock blocks being in mechanical engagement with an articulation inter-lock module securement means, said interlock module securement means being operable to convey each of said articulation interlock blocks from a coupling orientation to a locking orientation subsequent to positive coupling with each said mating means;
   whereby conveyance of said articulation inter-lock blocks to a locking orientation is effective to provide release of said locking means, thereby enabling articulation of each single surface section about said articulation means.

18. The articulation inter-lock module of claim 17, wherein said coupling means are self-aligning about said mating means.

19. The system of claim 1 wherein said primary single surface further includes framing.

20. The system of claim 1 wherein said primary single surface further includes an air mattress.

21. The system of claim 10 wherein each said means for releasable engagement is selfaligning.

22. The system of claim 7 wherein said matable receiving surface includes selfaligning features.

23. The system of claim 1, wherein said single surface transport and transfer frame includes:
   a pair of frame lower legs positioned at opposite ends of said frame;
   a collapsible/extendable lower cross member, extending between and connecting said frame lower legs, thereby effecting telescoping engagement of said frame lower legs; said collapsible/extendable lower cross member further engaging said frame lower legs in a manner effective to enable traversal of said lower cross member laterally across said legs;
   a cantilever column in telescopic engagement with each said frame lower legs, said cantilever column further effecting both rotatable and translatable engagemenL of each said single surface supporting member with each said frame lower legs;
   at least one telescoping, rotatable and longitudinally adjustable support, which is constructed and arranged for engagement with said single surface support platform, wherein each said adjustable support is provided with a pivoting support member mounted thereabove, each said pivoting support member being constructed and arranged for selective vertical and rotatable adjustability;
   each said supporting member further including adjustable extensions which are provided with a mating means assembly for selectively enabling reversible engagement with and adjustment of the single surface support platform;
   wherein said cross member is movable laterally across said frame from one side of said lower frame legs to another, and rotation of said single surface supporting member is enabled.

24. The system of claim 23, further including:
   a mechanism constructed and arranged to provide coordinated movement of the single surface supporting member and frame cantilever column;
   wherein lateral traversing movement of the frame cantilever column across the width of the frame lower leg causes rotation of the single surface supporting member in a coordinated fashion so as to effect a rotation of 180° upon completion of traversal of said frame lower leg by said frame cantilever column.

25. The system of claim 23, further including:
   a mechanism constructed and arranged to provide coordinated movement of the inner support column assembly and sliciably engaged cross member;
   wherein longitudinal positioning of the inner support column assembly along the length of said slidably engaged cross member causes rotation of the inner support column in a coordinated fashion so as to effect a rotation of 90° by said inner support column.

26. A single surface system useful for continuous support, transfer and treatment of an individual throughout a plurality of medical environments and procedures comprising:
   a primary single surface having a longitudinal axis and a lateral axis; said primary single surface including at least one matable receiving surface coextensive with a lateral edge thereof, which surface is adapted to receive at least one auxiliary component therein;
   said primary single surface further including an uppermost section and at least one adjacent section flexibly joined to at least one articulation means positioned therebetween, and at least one locking means for reversibly enabling articulation about said articulation means;
   said primary single surface further including an articulation interlock module adapted for reversible engagement with said single surface and including articulation inter-lock blocks incorporating therein coupling means adapted for reversible engagement with corresponding mating means affixed to a mating surface, said articulation inter-lock blocks being in mechanical engagement with an articulation inter-lock module securement means, which interlock modulb securement means is operable to convey each of said articulation inter-lock blocks from a coupling orientation to a locking orientation subsequent to positive coupling with each said mating means;
   a single surface transport and transfer frame constructed and arranged for reversible engagement with said primary single surface;
   at least one single surface-to-frame interface means for effecting reversible engagement of said primary single surface and said frame; each said single surface to frame interface means including (1) a single surface supporting member in adjustable engagement with said frame, and (2) supporting member engagement means constructed and arranged for self-aligning reversible engagement with said supporting member; wherein each said single surface supporting member is constructed and arranged for vertical adjustment with respect to said frame to enable horizontal positioning, vertical positioning and angular positioning of said single surface; and whereby engagement of said single surface-to-frame interface means results in reproducible positioning of said primary single surface upon said transport and transfer frame with respect to both the longitudinal and lateral axes of said primary single surface; and conveyance of said articulation inter-lock blocks to a locking orientation is effective to provide release of said locking means, thereby enabling articulation of each single surface section about said articulation means.

* * * * *